(12) United States Patent
Short et al.

(10) Patent No.: US 8,694,306 B1
(45) Date of Patent: Apr. 8, 2014

(54) SYSTEMS AND METHODS FOR SOURCE SIGNAL SEPARATION

(71) Applicant: Kaonyx Labs LLC, Durham, NH (US)

(72) Inventors: Kevin M. Short, Durham, NH (US); Brian T. Hone, Ipswich, MA (US)

(73) Assignee: Kaonyx Labs LLC, Durham, NH (US)

( * ) Notice: Subject to any disclaimer, the term of this patent is extended or adjusted under 35 U.S.C. 154(b) by 0 days.

(21) Appl. No.: 13/886,902

(22) Filed: May 3, 2013

Related U.S. Application Data

(60) Provisional application No. 61/749,606, filed on Jan. 7, 2013, provisional application No. 61/785,029, filed on Mar. 14, 2013, provisional application No. 61/642,805, filed on May 4, 2012.

(51) Int. Cl.
*G10L 21/00* (2013.01)

(52) U.S. Cl.
USPC .............................. 704/200; 704/206; 381/10

(58) Field of Classification Search
USPC ..................................... 704/200, 206; 381/10
See application file for complete search history.

(56) References Cited

U.S. PATENT DOCUMENTS

| | | | |
|---|---|---|---|
| 6,535,666 B1 * | 3/2003 | Dogan et al. ..................... | 385/31 |
| 7,454,333 B2 * | 11/2008 | Ramakrishnan et al. ..... | 704/228 |
| 2006/0053002 A1 * | 3/2006 | Visser et al. .................. | 704/200 |
| 2006/0153059 A1 * | 7/2006 | Spence et al. ................ | 370/203 |

* cited by examiner

*Primary Examiner* — Daniel D Abebe
(74) *Attorney, Agent, or Firm* — GTC Law Group LLP & Affiliates

(57) ABSTRACT

A method of processing a signal, including taking a signal formed from a plurality of source signal emitters and expressed in an original domain, decomposing the signal into a mathematical representation of a plurality of constituent elements in an alternate domain, analyzing the plurality of constituent elements to associate at least a subset of the constituent elements with at least one of the plurality of source signal emitters, separating at least a subset of the constituent elements based on the association and reconstituting at least a subset of constituent elements to produce an output signal in at least one of the original domain, the alternate domain and another domain.

20 Claims, 18 Drawing Sheets

SYSTEMS AND METHODS FOR SOURCE SIGNAL SEPARATION

CROSS-REFERENCE TO RELATED APPLICATIONS

This application claims the benefit of U.S. provisional patent application Ser. No. 61/749,606 filed Jan. 7, 2013, U.S. provisional patent application Ser. No. 61/785,029 filed Mar. 14, 2013, and U.S. provisional patent application Ser. No. 61/642,805 filed May 4, 2012 all of which are hereby incorporated by reference in their entirety.

BACKGROUND

1. Field of the Invention

The present invention relates to methods and systems for signal processing and, more specifically, to methods and systems for separating a signal into different components.

2. Description of the Related Art

Signal separation (SS) is a separation of any digital signal originating from a source into its individual constituent elements, such that those elements may be deconstructed, isolated, extracted, enhanced, or reconstituted in isolation, in part, or in whole. SS may be performed on any form of data including auditory data and/or visual data or images. SS may be performed using a plurality of source dependent methodologies including principal components analysis, singular value decomposition, spatial pattern analysis, independent component analysis (ICA), computational auditory scene analysis (CASA) or any other such technique.

Conventional SS techniques typically require prohibitive amounts of processing to achieve real or near real time performance and are thus far quite often incapable of effectively identifying and isolating signal sources within a given signal. There is therefore a need for a system and algorithms for operating such a system that provides for real or near real time signal separation.

SUMMARY OF THE INVENTION

The methods and systems for SS in accordance with various embodiments disclosed herein are source-agnostic. The nature of the original signal is generally irrelevant with respect to generation methodology or apparatus. Signal sources to which SS systems and methods may be applied include but are not limited to sound, audio, video, photographic, imaging (including medical), communications, optical/light, radio, RADAR, sonar, sensor and seismic sources. The methods and systems described herein may include a set of source agnostic systems and methods for signal separation. These include methods of high-resolution signal processing to mathematically describe a signal's constituent parts, methods of tracking and partitioning to identify portions of a signal that are "coherent"—i.e., emanating from the same source— and methods to re-combine selected portions, optionally in the original signal format, and/or sending them directly to other applications, such as a speech recognition system.

In accordance with an exemplary and non-limiting embodiment, a method of processing a signal comprises taking a signal formed from a plurality of source signal emitters and expressed in an original domain, decomposing the signal into a mathematical representation of a plurality of constituent elements in an alternate domain, analyzing the plurality of constituent elements to associate at least a subset of the constituent elements with at least one of the plurality of source signal emitters, separating at least a subset of the constituent elements based on the association and reconstituting at least a subset of constituent elements to produce an output signal in at least one of the original domain, the alternate domain and another domain.

In accordance with another exemplary and non-limiting embodiment, a method of processing a time domain signal comprises receiving an input signal comprising a time domain signal stream and creating a first windowed data set and a second windowed data set from the signal stream, wherein an initiation of the second windowed data set time lags an initiation of the first windowed data set, converting the first windowed data set and the second windowed data set to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency-domain high resolution windows to select a frequency-domain high resolution window that fits at least one of the amplitude, phase, amplitude modulation and frequency modulation of a component of an underlying signal wherein the component comprises at least one oscillator peak, using a tracking algorithm to identify at least one tracklet comprised of one or more oscillator peaks that emanate from a single oscillator source within the underlying signal, grouping tracklets that emanate from single sources and providing an output signal.

In accordance with another exemplary and non-limiting embodiment, a method of processing a time domain signal comprises receiving a time domain signal stream and creating a first windowed data set and a second windowed data set from the signal stream, wherein an initiation of the second windowed data set time lags an initiation of the first windowed data set, converting the first windowed data set and the second windowed data set to a frequency domain and storing the resulting data as frequency domain data having a fundamental transform resolution, performing complex spectral phase evolution (CSPE) on the frequency domain data to estimate component frequencies of first and second window at a resolution greater than the fundamental transform resolution, using the component frequencies estimated in the CSPE, sampling a set of stored high resolution frequency-domain windows in a singlet transformation process to select a high resolution frequency-domain window that fits at least one of the amplitude, phase, amplitude modulation and frequency modulation of the underlying signal oscillator, storing the parameters required for at least one of FM creation and AM creation in the frequency domain, wherein the parameters for FM creation include amplitude, phase, reference frequency, and modulation rate and the parameters for AM creation include amplitude, phase, frequency, and amplitude envelope information and recreating the frequency spectrum for at least one of an FM-modulating oscillator peak and an AM-modulating oscillator peak, such frequency spectrum including any transient effects where the oscillator may turn on or off at some point within the data sample window.

In accordance with another exemplary and non-limiting embodiment, a method of processing a signal comprises receiving a plurality of signal streams that may interfere with each other to some extent and creating first and second sets of input sample windows wherein an initiation of the second set time lags an initiation of the first set, converting both of the input sample windows from a time domain to a frequency domain, the resulting frequency domain data having a fundamental transform resolution, performing complex spectral phase evolution (CSPE) on the frequency-domain data to estimate component frequencies of the first and second data sets at a resolution greater than the fundamental transform resolution, using the component frequencies estimated in the CSPE, sampling a set of high resolution windows to select a high resolution window that, when properly multiplied by appropriate factors, fits at least one of the amplitude, phase, amplitude modulation and frequency modulation of an underlying signal component, using a tracking algorithm to identify at least one tracklet of oscillator peaks that emanate from a single oscillator source within the underlying signal, grouping tracklets that emanate from a single source, rejecting tracklets that are likely to be associated with noise or interfering signals, selecting at least one grouping of tracklets, reconstructing a signal from the selected groupings of tracklets and providing an output in a desired format using the selected grouping.

In accordance with another exemplary and non-limiting embodiment, a method of processing a signal comprises taking an original signal formed from a plurality of source signal emitters, the original signal expressed in an original domain, decomposing the signal into a mathematical representation of a plurality of constituent elements in an alternate domain, analyzing the plurality of constituent elements to associate at least a subset of the constituent elements with at least one of the plurality of source signal emitters, separating the constituent elements based on the association and preserving the constituent elements of the original input signal that correspond to at least one desired signal source for use as an output signal in the format of the original input signal.

In accordance with another exemplary and non-limiting embodiment, a method of processing a signal comprises taking a signal formed from a plurality of source signal emitters and expressed in an original transform domain, transforming the signal into a mathematical representation of a plurality of constituent elements in an alternate domain, performing complex spectral phase evolution (CSPE) on the combined alternate-domain data to estimate constituent element characteristics at a resolution greater than the resolution of the original transform domain, analyzing the plurality of constituent elements to associate at least a subset of the constituent elements with at least one of the plurality of source signal emitters, separating at least a subset of the constituent elements based on the association and reconstituting at least a subset of constituent elements to produce an output signal including output from at least one desired source signal emitter in at least one of the original domain, the alternate domain and another domain.

In accordance with another exemplary and non-limiting embodiment, a method of separating components of an input signal comprises taking a signal formed from a plurality of source signal emitters that interfere with each other to some extent, the input signal expressed in an original domain, decomposing the signal into a representation of a plurality of constituent elements in an alternate domain, representing the decomposed signal in a unified domain data structure that allows representation of phase, frequency, amplitude, and directional information, analyzing the plurality of constituent elements to associate at least a subset of the constituent elements with at least one of the plurality of source signal emitters, the analysis including use of a unified domain directional estimate to assist in the association, separating at least a subset of the constituent elements based on the association and reconstituting at least a subset of constituent elements to produce an output signal including output from at least one desired source signal emitter in a desired format.

In accordance with another exemplary and non-limiting embodiment, a method of processing a time domain signal comprises receiving a time domain signal stream and creating a first window and a second window from the signal stream, wherein an initiation of the second window time lags an initiation of the first window, converting at least one of the windows to a frequency domain and storing the resulting data as frequency domain data having a fundamental transform resolution, performing complex spectral phase evolution (CSPE) on the frequency domain data to estimate component frequencies of first and second window at a resolution greater than the fundamental transform resolution, using the component frequencies estimated in the CSPE, sampling a set of stored high resolution frequency-domain windows in a singlet transformation process to select a high resolution frequency-domain window that fits at least one of the amplitude, phase, amplitude modulation and frequency modulation of the underlying signal oscillator, storing the parameters required for at least one of FM creation and AM creation in the frequency domain, wherein the parameters for FM creation include amplitude, phase, reference frequency, and modulation rate and the parameters for AM creation include amplitude, phase, frequency, and amplitude envelope information and recreating the frequency spectrum for at least one of an FM-modulating oscillator peak and an AM-modulating oscillator peak, such frequency spectrum including any transient effects where the oscillator may turn on or off at some point within the data sample window.

In accordance with another exemplary and non-limiting embodiment, a method for detecting signal modulation comprises providing a set of modulating complex operators having real and imaginary parts that can be applied to a stable oscillator to produce a modulated oscillator, providing a further set of operators known as pullback operators that can counteract the modulating effects on an oscillator, applying a pull-back operator to a modulated signal so that when the signal is transformed from a time domain to a frequency domain at least a portion of a modulation effect is counteracted, applying a pull-back operator to a time-lagged sample window data set so that the modulation effect is counteracted in the time-lagged sample window so as to revert it to a state that can be compared to the transform of the initial sample window and comparing the transformed initial and pulled-back time-lagged sample window data to derive a super-resolution transform representation that reveals the underlying reference frequency for the frequency modulation of the modulated signal.

In accordance with another exemplary and non-limiting embodiment, a method of processing a signal comprises receiving a plurality of signal streams that interfere with each other to some extent and creating first and second sets of input sample windows wherein an initiation of the second set time lags an initiation of the first set, converting the first and second sets of input sample windows from a time domain to a frequency domain, the resulting frequency domain data having a fundamental transform resolution, performing complex spectral phase evolution (CSPE) on the frequency-domain data to estimate component frequencies of the first and second data sets at a resolution greater than the fundamental transform resolution wherein the CSPE uses window sizes of varying length, using the component frequencies estimated in the CSPE, sampling a set of stored high resolution windows to select a high resolution window of a first window length that fits at least one of the amplitude, phase, amplitude modulation and frequency modulation of an underlying signal component comprising a plurality of oscillator peaks, using a tracking algorithm to identify at least one tracklet of oscillator peaks that emanate from a single oscillator source within the underlying signal, grouping tracklets that emanate from a single source, rejecting tracklets that are likely to be associated with noise or interfering signals, selecting at least one grouping of tracklets, reconstructing a signal from the selected groupings of tracklets wherein the reconstruction uses windows of a desired length that is optionally different from the first window length analyzed in the CSPE and providing an output in a desired format using the selected grouping.

In accordance with another exemplary and non-limiting embodiment, a method of processing a signal comprises receiving a time domain signal stream and creating a first window and a second window from the signal stream, wherein an initiation of the second window time lags an initiation of the first window, converting the first window and second window to a frequency domain and storing the resulting frequency domain data having a fundamental transform resolution, performing complex spectral phase evolution (CSPE) on the frequency domain data to estimate component frequencies of the windowed data at a resolution greater than the fundamental transform resolution, using the component frequencies, sampling a set of stored frequency-domain high resolution windows to select frequency-domain high resolution windows that may fit the modulation of a component of the underlying signal wherein the component comprises a plurality of oscillator peaks, using a tracking algorithm to identify at least one tracklet of oscillator peaks that emanate from a single oscillator source within the underlying signal and using information from a behavior of the tracklet with which an oscillator peak is associated to assist in providing an estimate of the modulation of the oscillator.

In accordance with another exemplary and non-limiting embodiment, a method of processing a signal comprises analyzing the super-resolution frequency information in a sequence of windows of data, combining the super-resolution frequency information with the corresponding phase information for the windows of data, modeling the evolution of the signal over the windows of data to predict the frequency or phase of the signal for windows that are advanced in time or backward in time, using any combination of signal frequencies or phases to predict the expected values for any set of frequencies and phases that are not included in the model prediction.

In accordance with another exemplary and non-limiting embodiment, a method of processing a signal to produce a mathematical decomposition of the signal in such a way that the decomposed elements of the signal can be recombined to produce a lossless representation of the original signal comprises creating a model of the signal in data windows using a sum of oscillator peaks created using short-time stable oscillators, frequency modulating oscillators, and amplitude modulating oscillators, removing each modeled signal element from the original signal until a desired degree of accuracy is achieved and so that all that remains is a sufficiently small residual signal, encoding the residual signal so that it can be reproduced exactly and storing the parameters of the oscillator peaks used in the modeling of the data along with the encoded residual signal so that they can be recombined into an exact lossless reconstruction of the original signal.

In accordance with another exemplary and non-limiting embodiment, a method of processing a time domain signal comprises receiving a time domain signal stream and creating a first window and a second window from the signal stream, wherein an initiation of the second window time lags an initiation of the first window, converting the first window and the second window to a frequency domain and storing the resulting data as frequency domain data having a fundamental transform resolution, performing complex spectral phase evolution (CSPE) on the frequency domain data to estimate component frequencies of the windowed data at a resolution greater than the fundamental transform resolution, using the component frequencies, sampling a set of stored frequency-domain high resolution windows to select a frequency-domain high resolution window that fits at least one of the amplitude, phase, amplitude modulation and frequency modulation of a component of an underlying signal wherein the component comprises at least one oscillator peak, using a tracking algorithm to identify at least one tracklet comprised of one or more oscillator peaks that emanate from a single oscillator source within the underlying signal grouping tracklets that emanate from a single source and providing an output signal.

In accordance with another exemplary and non-limiting embodiment, a method of processing a time domain signal comprises receiving a plurality of signal streams and creating first and second sets of input sample windows each corresponding to one of the plurality of signal streams, wherein an initiation of the second set of input samples time lags an initiation of the first set of input samples, converting the first and second input sample windows to a frequency domain and storing the resulting data as frequency domain data having a fundamental transform resolution, performing complex spectral phase evolution (CSPE) on the frequency domain data set to estimate component frequencies of the input sample windows at a resolution greater than the fundamental transform resolution, using the component frequencies estimated in the CSPE, sampling a set of stored high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet comprised of one or more oscillator peaks that emanate from a single oscillator source within the underlying signal, grouping tracklets that emanate from a single source and providing an output signal.

In accordance with another exemplary and non-limiting embodiment, a method of processing a time domain signal comprises receiving a time domain signal stream and creating a first window and a second window from the signal stream, wherein an initiation of the second window time lags an initiation of the first window, converting the first and second windows to a frequency domain and storing the resulting data as frequency domain data having a fundamental transform resolution, performing complex spectral phase evolution (CSPE) on the frequency domain data to estimate component frequencies of the first and second windows at a resolution greater than the fundamental transform resolution, using the component frequencies estimated in the CSPE, sampling a set of stored high resolution frequency-domain windows to select a high resolution frequency-domain window that fits at least one of the amplitude, phase, amplitude modulation and frequency modulation of an underlying signal component comprising at least one oscillator peak and removing the effects of the estimated component from at least one of the stored windowed data sets, using a tracking algorithm to identify at least one tracklet of oscillator peaks that emanate from a single oscillator source within the underlying signal, grouping tracklets that emanate from a single source and providing an output signal.

In accordance with another exemplary and non-limiting embodiment, a method of processing a time domain signal, comprises receiving a plurality of signal streams and creating first and second windows each comprising a set of input samples corresponding to one of the plurality of signal streams, wherein an initiation of the second window lags an initiation of the first window, converting the first and second windows to a frequency domain and storing the resulting frequency domain data having a fundamental transform resolution, representing a plurality of channels each comprising a first set and a second set of frequency domain data in a unified domain representation and performing complex spectral phase evolution (CSPE) on the frequency domain data to estimate component frequencies of the frequency domain data at a resolution greater than the fundamental transform resolution of the frequency domain data, including using the phase rotation measured between two time-separated sample windows to detect an actual underlying frequency at said greater resolution, using the component frequencies estimated in the CSPE, sampling a set of stored high resolution windows to select a high resolution window that fits at least one of the amplitude, phase, amplitude modulation and frequency modulation of the underlying signal component comprising at least one oscillator peak, using a tracking algorithm to identify at least one tracklet of oscillator peaks that emanate from a single oscillator source within the underlying signal, grouping tracklets that emanate from a single source and providing an output signal.

In accordance with another exemplary and non-limiting embodiment, a method of processing a time domain signal comprises receiving a time domain signal stream comprising an original signal and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and reproducing a selected portion of the original signal as an output signal.

In accordance with another exemplary and non-limiting embodiment, a method of processing a time domain signal comprises receiving a time domain signal stream and creating a first window comprising a first set of input samples (multiplied by an analysis window) in the time domain and a second window comprising a second set of input samples (multiplied by an analysis window) in the time domain from the signal stream, wherein an initiation of the second set of input samples time lags an initiation of the first set of input samples, converting the first and second input sample windows to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and providing an output signal in the form of a mathematical representation stored in a computer-accessible form.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and providing an output signal in the form of a feature vector adapted for use in a speech processing system.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and reproducing a selected portion of the original signal as an output signal.

In accordance with another exemplary and non-limiting embodiment, a method of processing a time domain signal comprises receiving a time domain signal stream and creating a first windowed data set and a second windowed data set comprising data from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and providing an output signal in the form of a mathematical representation stored in a computer-accessible form.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and providing an output signal in the form of a feature vector adapted for use in a speech processing system.

In accordance with another exemplary and non-limiting embodiment, a method of processing a time domain signal comprises receiving a time domain signal stream and creating a first window data set and a second window data set comprising samples from the signal stream multiplied by an analysis window, wherein an initiation of the second window lags an initiation of the first window converting the first and second windowed data sets to a frequency domain and storing the resulting data as frequency domain data having a fundamental transform resolution performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and grouping tracklets that emanate from a single source within the underlying signal and reproducing a selected portion of the original signal as an output signal.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak; and grouping tracklets that emanate from a single source within the underlying signal and providing an output signal in the form of a mathematical representation stored in a computer-accessible form.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and grouping tracklets that emanate from a single source within the underlying signal and providing an output signal in the form of a feature vector adapted for use in a speech processing system.

In accordance with another exemplary and non-limiting embodiment, a method of processing a time domain signal comprises representing a plurality of channels each comprising a first window comprising a first set and a second window comprising a second set of frequency domain data in a unified domain representation and performing complex spectral phase evolution (CSPE) on the frequency domain data to estimate component frequencies of the frequency domain data at a resolution greater than the fundamental transform resolution of the frequency domain data, including using the phase rotation measured between the frequency domain representation of two time-separated sample windows to detect an actual underlying frequency at said greater resolution.

In accordance with another exemplary and non-limiting embodiment, a method of processing a time domain audio signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution and using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak.

In accordance with another exemplary and non-limiting embodiment, a method of processing a time domain video signal comprises receiving a time domain signal stream such as can be created by scanning rows or columns of a digital image or video frame and creating a first windowed data set, and a second windowed data set comprising samples from the signal stream and optionally multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution and using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and using a tracking algorithm to identify at least one tracklet of oscillator peaks that emanate from a single oscillator source within the underlying signal.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and using a tracking algorithm to identify at least one tracklet of oscillator peaks that emanate from a single oscillator source within the underlying signal, wherein the tracking algorithm uses information from the CSPE to predict the behavior of an oscillator component of a signal.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet of oscillator peaks that emanate from a single oscillator source within the underlying signal and grouping tracklets that emanate from a single source.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second window data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet of oscillator peaks that emanate from a single oscillator source within the underlying signal, grouping tracklets that emanate from a single source and receiving a plurality of signal streams and creating first and second sets of input sample windows each corresponding to one of the plurality of signal streams, wherein an initiation of the second set of input samples time lags an initiation of the first set of input samples.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet of oscillator peaks that emanates from a single oscillator source within the underlying signal, grouping tracklets that emanate from a single source and providing an output signal.

In accordance with another exemplary and non-limiting embodiment, a method of processing a time domain signal comprises performing complex spectral phase evolution (CSPE) on frequency domain data to estimate component frequencies of the frequency domain data at a resolution greater than a fundamental transform resolution of the frequency domain data and using the component frequencies estimated in the CSPE, sampling a set of stored high resolution windows to select a high resolution window that fits at least one of the amplitude, phase, amplitude modulation and frequency modulation of the underlying signal component.

In accordance with another exemplary and non-limiting embodiment, a method of processing a time domain signal comprises performing complex spectral phase evolution (CSPE) on frequency domain data to estimate component frequencies of the frequency domain data at a resolution greater than a fundamental transform resolution of the frequency domain data and determining an estimated frequency modulation in one or more oscillator peaks in a windowed data set, applying a plurality of frequency modulation pullback operators (FMPO) to the sample data, applying at least one of a non-linear interpolation, a linear interpolation, and an extrapolation to the resulting data to provide an improved estimate of the frequency modulation of the underlying signal component, and storing the improved estimate in a further modified high resolution window data set.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak and separating the underlying signal into a plurality of signal components each corresponding to one of a plurality of distinct sources, reconstructing a single merged signal that best represents the plurality of signal components, and providing the merged signal as an output.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet of oscillator peaks that emanate from a single oscillator source within the underlying signal and separating the underlying signal into a plurality of signal components each corresponding to one of a plurality of distinct sources, reconstructing a single merged signal that best represents the plurality of signal components, and providing the merged signal as an output.

In accordance with another exemplary and non-limiting embodiment, a method of processing a time domain signal comprises receiving a time domain signal stream and creating a first windowed data set and a second windowed data set comprising samples from the signal stream, wherein an initiation of the second window lags an initiation of the first window, converting the first and second windowed data sets to a frequency domain and storing the resulting data as frequency domain data having a fundamental transform resolution, performing complex spectral phase evolution (CSPE) on the frequency domain data to estimate component frequencies of the first and second windowed data sets at a resolution greater than the fundamental transform resolution, using the component frequencies estimated in the CSPE, sampling a set of frequency domain high resolution windows to select a high resolution window that fits at least one of the amplitude, phase, amplitude modulation and frequency modulation of a component of an underlying signal wherein the component comprises at least one oscillator peak, using a tracking algorithm to identify at least one tracklet of oscillator peaks that emanate from a single oscillator source within the underlying signal, grouping tracklets that emanate from a single source and separating the underlying signal into a plurality of signal components each corresponding to one of a plurality of distinct sources, reconstructing a single merged signal that best preserves desired features, and providing the merged signal as an output.

In accordance with another exemplary and non-limiting embodiment, a method of processing a time domain signal comprises receiving a time domain signal stream and creating a first windowed data set and a second windowed data set comprising samples from the signal stream multiplied by an analysis window, wherein an initiation of the second window lags an initiation of the first window, converting the first and second windows to a frequency domain and storing the resulting data as frequency domain data having a fundamental transform resolution, performing complex spectral phase evolution (CSPE) on the frequency domain data to estimate component frequencies of the frequency domain data at a resolution greater than the fundamental transform resolution of the frequency domain data, using the component frequencies estimated in the CSPE, sampling a set of stored high resolution windows in a singlet transformation process to select a high resolution window that fits the amplitude, phase, amplitude modulation and frequency modulation of the underlying signal component comprising at least one oscillator peak and removing the effects of the estimated component from at least one of the stored windowed data sets, using a tracking algorithm to identify at least one tracklet of oscillator peaks that emanate from a single oscillator source within the underlying signal, wherein the tracking algorithm uses information from the CSPE to predict the behavior of an oscillator component of a signal, grouping tracklets that emanate from a single source, wherein grouping is aided by a visual representation of a plurality of tracklets displayed in a graphical user interface that enables at least one of selection, deletion and association of a tracklet and providing an output signal wherein converting the first and second sets of input samples comprises converting the first and second sets of input samples to the frequency domain using at least one of a Discrete Fourier transform (DFT) and a Fast Fourier Transform (FFT), and any related transform.

In accordance with another exemplary and non-limiting embodiment, a method of processing a time domain signal comprises receiving a plurality of signal streams and creating first and second sets of input sample windows each corresponding to one of the plurality of signal streams, wherein an initiation of the second set of input samples time lags an initiation of the first set of input samples and wherein converting the first and second sets of input samples comprises converting the first and second sets of input samples to the frequency domain using at least one of a Discrete Fourier transform (DFT) and a Fast Fourier Transform (FFT), further comprising multiplying the first set of input samples and the second set of input samples with an analysis window, converting the first and second input sample windows to a frequency domain, modifying the converted window by adding at least one of an amplitude effect and a frequency effect, and storing the resulting modified window data set, representing a plurality of channels each comprising a first set and a second set of frequency domain data in a unified domain representation and performing complex spectral phase evolution (CSPE) on the frequency domain data to estimate component frequencies of the frequency domain data at a resolution greater than the fundamental transform resolution of the frequency domain data, including using the phase rotation measured between two time-separated sample windows to detect an actual underlying frequency at said greater resolution, using the component frequencies estimated in the CSPE, sampling a set of stored high resolution windows in a singlet transformation process to select a high resolution window that fits the amplitude, phase, amplitude modulation and frequency modulation of the underlying signal component and removing the effects of the estimated component from at least one of the stored windowed data sets, using a tracking algorithm to identify at least one tracklet of oscillator peaks that emanate from a single oscillator source within the underlying signal, wherein the tracking algorithm uses information from the CSPE to predict the behavior of an oscillator component of a signal, grouping tracklets that emanate from a single source, wherein grouping is aided by a visual representation of a plurality of tracklets displayed in a graphical user interface that enables at least one of selection, deletion and association of a tracklet and providing an output signal.

In accordance with another exemplary and non-limiting embodiment, a method of processing a time domain signal comprises receiving a time domain signal stream and creating a first set of input samples in the time domain and a second set of input samples in the time domain from the signal stream, wherein an initiation of the second set of input samples time lags an initiation of the first set of input samples, multiplying the sets of input samples by an analysis window, converting the first and second input sample windows to a frequency domain and storing the resulting transformed windowed data set for analysis, performing complex spectral phase evolution (CSPE) on the frequency domain data to estimate component frequencies of the frequency domain data at a resolution greater than the fundamental transform resolution of the frequency domain data, using the component frequencies estimated in the CSPE, sampling a set of stored high resolution windows to select a high resolution window that fits at least one of the amplitude, phase, amplitude modulation and frequency modulation of the underlying signal component comprising at least one oscillator peak, determining an estimated frequency modulation in a stored high resolution window data set, applying a plurality of frequency modulation pullback operators (FMPO) to the sample data, applying at least one of a non-linear interpolation, a linear interpolation, and an extrapolation to the resulting data to provide an improved estimate of the frequency modulation of the underlying signal component, and storing the improved estimate in a further modified high resolution window data set, using a tracking algorithm to identify at least one tracklet of oscillator peaks that emanate from a single oscillator source within the underlying signal, grouping tracklets that emanate from a single source and providing an output signal.

In accordance with another exemplary and non-limiting embodiment, a method of processing a time domain signal comprises receiving a plurality of signal streams and creating first and second sets of input sample windows each corresponding to one of the plurality of signal streams, wherein an initiation of the second set of input samples time lags an initiation of the first set of input samples and wherein converting the first and second sets of input samples comprises converting the first and second sets of input samples to the frequency domain using at least one of a Discrete Fourier transform (DFT) and a Fast Fourier Transform (FFT) or a discrete cosine transform or another related transform, further comprising multiplying the first set of input samples and the second set of input samples with an analysis window, converting the first and second input sample windows to a frequency domain, modifying the converted window by adding at least one of an amplitude effect and a frequency effect, and storing the resulting modified windowed data set, representing a plurality of channels each comprising a first set and a second set of frequency domain data in a unified domain representation and performing complex spectral phase evolution (CSPE) on the frequency domain data to estimate component frequencies of the frequency domain data at a resolution greater than the fundamental transform resolution of the frequency domain data, including using the phase rotation measured between two time-separated sample windows to detect an actual underlying frequency at said greater resolution, using the component frequencies estimated in the CSPE, sampling a set of stored high resolution windows in a singlet transformation process to select a high resolution window that fits at least one of the amplitude, phase, amplitude modulation and frequency modulation of the underlying signal component and removing the effects of the estimated component from at least one of the stored windowed data sets, using a tracking algorithm to identify at least one tracklet of oscillator peaks that emanate from a single oscillator source within the underlying signal, wherein the tracking algorithm uses information from the CSPE to predict the behavior of an oscillator component of a signal, grouping tracklets that emanate from a single source, wherein grouping is aided by a visual representation of a plurality of tracklets displayed in a graphical user interface that enables at least one of selection, deletion and association of a tracklet and separating the underlying signal into a plurality of signal components each corresponding to one of a plurality of distinct sources, and optionally reconstructing a single merged signal that best represents the plurality of signal components, and providing the (optionally) merged signal as an output.

In accordance with another exemplary and non-limiting embodiment, a method of processing a signal comprises receiving a plurality of signal streams each comprising a substantial amount of ambient noise or interfering signals and creating first and second sets of input sample windows each corresponding to one of the plurality of signal streams, wherein an initiation of the second set of input samples time lags an initiation of the first set of input samples, multiplying the first and second sample windows by an analysis window, converting the first and second input sample windows to a frequency domain and storing the resulting data, performing complex spectral phase evolution (CSPE) on the frequency-domain data to estimate component frequencies of the data set at a resolution greater than the fundamental transform resolution, using the component frequencies estimated in the CSPE, sampling a set of stored high resolution windows to select a high resolution window that fits at least one of the amplitude, phase, amplitude modulation and frequency modulation of the underlying signal component, using a tracking algorithm to identify at least one tracklet of oscillator peaks that emanate from a single oscillator source within the underlying signal, grouping tracklets that emanate from a single source, rejecting tracklets that are likely to be associated with noise or interfering signals, selecting at least one grouping of tracklets, reconstructing a signal from the selected groupings of tracklets and providing the signal as an output.

BRIEF DESCRIPTION OF THE FIGURES

In the figures, which are not necessarily drawn to scale, like numerals may describe substantially similar components throughout the several views. Like numerals having different letter suffixes may represent different instances of substantially similar components. The figures illustrate generally, by way of example, but not by way of limitation, certain embodiments discussed in the present document.

DETAILED DESCRIPTION

Figure 1:
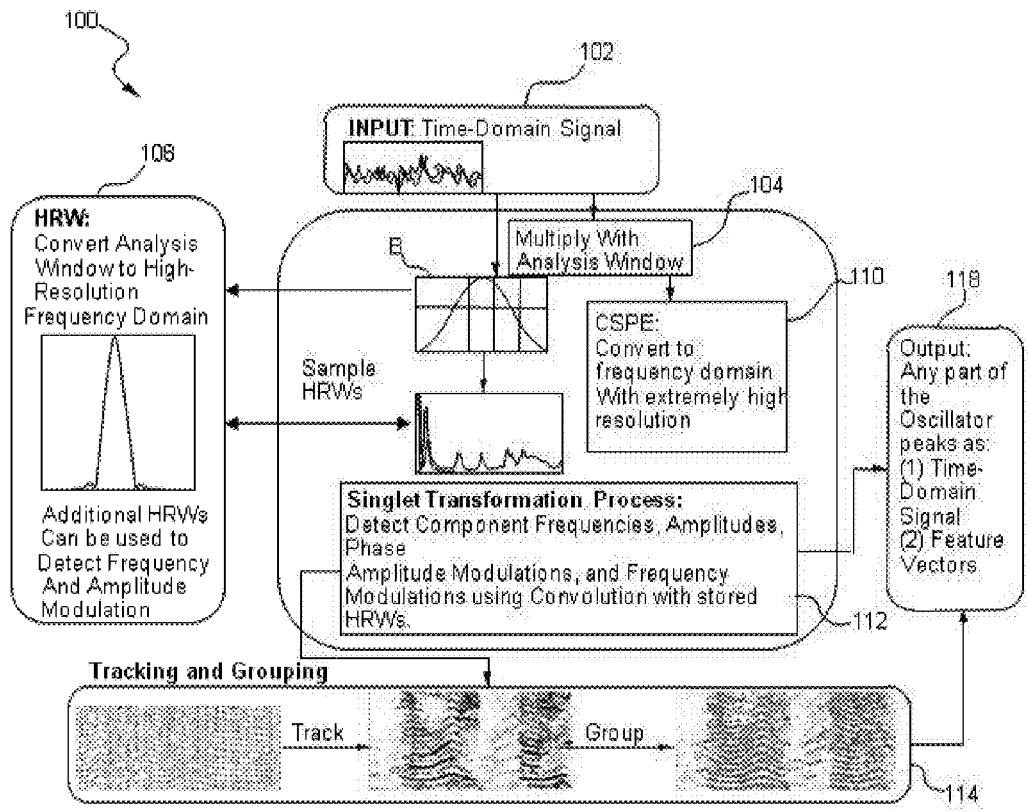
FIG. 1 is an illustration of a signal extraction process according to an exemplary and non-limiting embodiment.

FIG. 1 illustrates an exemplary and non-limiting embodiment of a method 100 for source signal separation. In an example, a representative input signal may be a source signal (SS) including an audio signal/sound as an input to the system such that the SS is a source agnostic and may be used with respect to any type of source signal. Other representative input signals may include but are not limited to ambient sound, audio, video, speech, image, communication, geo-physical, SONAR, RADAR, thermal, optical/light, medical, and musical signals. The method 100 may include one or more steps that may be used in combination or in part to analyze the SS, separate the SS into its constituent elements, and then reconstitute the SS signal in whole or in part.

As shown in FIG. 1, the method 100 may be configured to select a signal at step 102 so as to process the signal for the signal separation. In an example, contiguous samples (referred to herein as "windows" or "sample windows" that may represent windows of samples in time) may be selected for analysis. Typically, multiple windows may be selected with a small time-delay between them. Further, at step 104, the method 100 may be configured to multiply the SS (i.e., in the form of contiguous samples) with an analysis window such as a window B1 as illustrated in FIG. 1. The analysis window may also be referred to herein as a taper.

At step 108, a high resolution window (HRW) such as a HRW C1 may be created. Further, a copy of the analysis window used for signal preparation may be converted to a high-resolution frequency domain and stored for oscillator peak analysis. Optionally, sets of HRWs may be stored that have amplitude and frequency modulation effects added therein. At step 110, a conversion to Frequency Domain and Complex Spectral Phase Evolution (CSPE) high-resolution frequency estimate may be performed. In an example, time-domain windows are converted to the frequency domain via a transform, such as a Fast Fourier Transform (FFT), the Discrete Fourier Transform (DFT) the Discrete Cosine Transform (DCT) or other related transform. The accuracy of frequency estimates created by such transforms may be conventionally limited by the number of input samples. The CSPE transform overcomes these limitations and provides a set of highly accurate frequency estimates. In particular, the CSPE calculation uses the phase rotation measured between the transforms of two time-separated sample windows to detect the actual underlying frequency.

At step 112, the method 100 may be configured to identify oscillator peak parameters via a Singlet Transform Process. Specifically, high resolution windows (HRWs) are sampled to select the HRW with the most accurate fit to estimate the amplitude, phase, amplitude modulation and frequency modulation of the underlying signal component using high accuracy frequency estimates that are provided by the CSPE calculation. In some embodiments, one may remove the effects of this component so that estimates of nearby oscillators may become more accurate. The singlet transform process may be reversed to re-produce portions of or the entire original frequency domain signal. At step 114, the method 100 may be configured to perform tracking and grouping. In an example, the tracking may be performed to identify oscillator peaks that may emanate from a single oscillator using tracking algorithms, such as a single harmonic produced by a musical instrument or a person's voice. A set of oscillator peaks that has been determined to be emanating from a single source is called a tracklet. In an example, the grouping may be performed to identify tracklets that emanate from a single source. For example, such a grouping can include multiple harmonics of a single musical instrument or person's voice. A set of tracklets that has been determined to be emanating from a single source is called a coherent group.

At step 118, the oscillator peaks may be output at any stage after the singlet transform process. Further, the information gathered in the tracking and grouping stages may be used to select a set of desired oscillator peaks. In an example, some or all oscillator peaks may be converted accurately into some or all of the original signal formats using the singlet transform process. In another example, some or all oscillator peaks may be converted into another format, such as a feature vector that may be used as an input to a speech recognition system or may be further transformed through a mathematical function directly into a different output format. The above steps may be used to analyze, separate and reconstitute any type of signal. The output of this system may be in the same form as the original signal or may be in the form of a mathematical representation of the original signal for subsequent analysis.

As used herein in the detailed description, a "frequency-phase prediction" is a method for predicting the frequency and phase evolution of a tracklet composed of oscillator peaks. As used herein, a "feature vector" is a set of data that has been measured from a signal. In addition, commonly feature vectors are used as the input to speech recognition systems. As used herein, "Windowed transform" refers to pre-multiplying an original sample window by a "taper" or windowing function (e.g., Hanning, Hamming, boxcar, triangle, Bartlett, Blackman, Chebyshev, Gaussian and the like) to shape spectral peaks differently. As used herein, "Short" refers, generally, to a finite number of samples that is appropriate to a given context and may include several thousand or several hundreds of samples, depending on the sample rate, such as in a Short Time Fourier Transform (STFT). For example, an audio CD includes 44100 samples per second, so a short window of 2048 samples is still only about ½₀th of a second. As used herein a "tracklet" refers to a set of oscillator peaks from different frames that a tracker has determined to be from the same oscillator. As used herein, a "Mahalanobis Distance" refers to a well-known algorithm in the art for measuring the distance between two multi-dimensional points that takes uncertainty measures into account. This algorithm is commonly used in tracking applications to determine the likelihood that a tracklet and a measurement should be combined or assigned to the same source or same tracklet. As used herein, "tracklet association" refers to a method for determining which new measurements should be combined with which existing tracklets. As used herein, "greedy association" refers to an algorithm known in the art for performing tracklet association. As used herein, "partitioning" refers to a method for dividing tracklets into distinct groups. Generally these groups will correspond to distinct sound emitters, such as a person speaking. As used herein, a "union find" is an algorithm known in the art for partitioning. As used herein, a "coherent group" refers to a set of tracklets that have been determined to be from the same signal emitter, such as a person speaking. As used herein, a "Mel Frequency Complex Coefficient" is a well-known type of feature commonly used as the input to speech recognition systems.

In accordance with one or more embodiments, the methods and systems for SS disclosed herein may facilitate separation of a source signal into a plurality of signal elements. The methods and systems described herein may be used in whole or in part to isolate and enhance individual elements in the source signal. The systems and methods may be applied to generally any signal source to achieve signal separation.

In accordance with one or more embodiments, the methods and systems for SS may facilitate execution of a series of algorithms that may be used in part or in combination to perform signal separation and enhancement. The series of algorithms may be implemented in hardware, software, or a combination of hardware and software.

In accordance with one or more embodiments, the methods and systems for SS may be configured to a pre-processor that may be a single-channel or a multi-channel, and a super-resolution module that may be a single-channel or a multi-channel. In accordance with one or more embodiments, the methods for SS may include a family of methods that may be based on Complex Spectral Phase Evolution, including methods for short-time stable sinusoidal oscillations, short-time linear frequency modulation methods, time-varying amplitude modulation methods, joint amplitude and frequency modulation methods, and a Singlet Representation method. As used herein, FM-CSPE refers to the specific methods within the family of CSPE methods that apply to frequency modulating signals. Similarly, AM-CSPE refers to the specific methods within the family of CSPE methods that apply to amplitude modulating signals.

The methods and systems for SS described herein can provide one or more of the following advantages. For example, the methods and systems may facilitate extraction of interfering elements from the source signal separately and unwanted elements may be removed from the source signal. In an example, targeted elements of the source signal may be extracted or isolated without corrupting the targeted element using the methods and systems for SS. In another example, overlapping signal elements within the same frequency range may be independently extracted and enhanced despite the convolution effects of the measurement process (also known as "smearing" or the "uncertainty principle"). The methods and systems for SS as described herein may facilitate provisioning of a detailed analysis of the source signal due to an increase in an accuracy of the processing techniques of the methods and systems for SS disclosed herein with respect to current processing techniques.

In accordance with one or more embodiments, the methods and systems for SS may be configured to include a signal component tracker that may be configured to implement a method for grouping signal components in time, and/or by harmonics, and/or by other similarity characteristics to identify coherent sources. In accordance with one or more embodiments, the methods and systems for SS may be configured to include a coherent structure aggregator and a coherent structure selector/separator such that the coherent structure selector/separator may be configured to implement a method for identifying coherent structures for extraction, isolation, enhancement, and/or re-synthesis. In accordance with one or more embodiments, the methods and systems may be configured to include a unified domain transformation and unified domain complex spectral phase evolution (CSPE)

such as to combine multiple signal channels into a single mathematical structure and to utilize a version of the CSPE methods designed to work in the unified domain. The methods and systems for SS may be configured to include a re-synthesis module that may facilitate generation of a frequency domain signal from a set of oscillator peaks. The re-synthesis module may be implemented using a single-channel or a multi-channel module.

In accordance with one or more embodiments, the SS system may be configured to include a multi-channel preprocessor, a multi-channel super-resolution module, a tracker/aggregator/selector/separator, and a multi-channel re-synthesis module. In accordance with one or more embodiments, the methods for SS may be configured to include one or more of the operations such as a complex spectral phase evolution (CSPE), a singlet representation method, a unified domain transformation, a unified domain complex spectral phase evolution, a signal component tracking, a coherent structure aggregation, a coherent structure separation, a coherent structure reconstruction in the time domain, an ambient signal remixing or reconstitution and other operations.

The CSPE operation may refer to a method for overcoming the accuracy limitations of the Fast Fourier Transform (FFT) or Discrete Fourier Transform (DFT). The CSPE operation may improve an accuracy of FFT-based spectral processing, in some embodiments from 21.5 Hz to the order of 0.1 Hz. In some embodiments, the accuracy may be better than 0.1 Hz. In accordance with one or more embodiments, the CSPE operations may be configured to include short-time stable sinusoidal oscillation methods, short-time linear frequency modulation methods, time-varying amplitude modulation methods, and joint amplitude and frequency modulation methods.

The singlet representation method refers to a method by which a short-time stable or quasi-stable oscillator may be projected into a frequency domain signal or extracted from a frequency domain signal. In an example, the oscillator may refer to any source of oscillation, including but not limited to a sinusoidal oscillation, a short-time stable oscillation of any duration, a quasi-stable oscillation, or a signal that may be created to a desired degree of accuracy by a finite sum of such oscillators. The singlet transformation or singlet representation may include information on an amplitude, phase and (super-resolution) frequency of the oscillator, along with information about the smearing characteristics of the oscillator that may indicate the degree of interference with other signal elements. Further, the singlet representation can include information about the smearing and interference characteristics as a function of the number of decibels of interference in a given frequency bin of the original FFT or DFT. In some embodiments, the singlet representation may include information about the (super-resolution) frequency modulation, amplitude modulation and joint frequency-amplitude modulation characteristics.

The unified domain transformation may refer to a method for combining multiple signal channels into a single mathematical structure and the unified domain complex spectral phase evolution may refer to a version of the CSPE methods designed to work in the Unified Domain. The signal component tracking may refer to a method for grouping signal components in time, and/or by harmonics, and/or by other similarity characteristics to identify coherent sources. The coherent Structure Separation may refer to a method for identifying coherent structures for extraction, isolation, enhancement, and/or re-synthesis and the coherent structure reconstruction may refer to a method for creating a frequency domain or time domain signal that is composed of selected oscillator peaks. The ambient signal remixing or reconstitution may refer to a method for adding the original signal (or an amplified or attenuated version of the original signal) to the signal created by coherent structure reconstruction in the time domain to generate a signal having certain desirable characteristics. In an example, an output may include coherent structure reconstruction in the time domain, an ambient signal remixing or reconstitution, feature vector creation and automatic translation from mathematical representation to other output formats.

Figure 2:
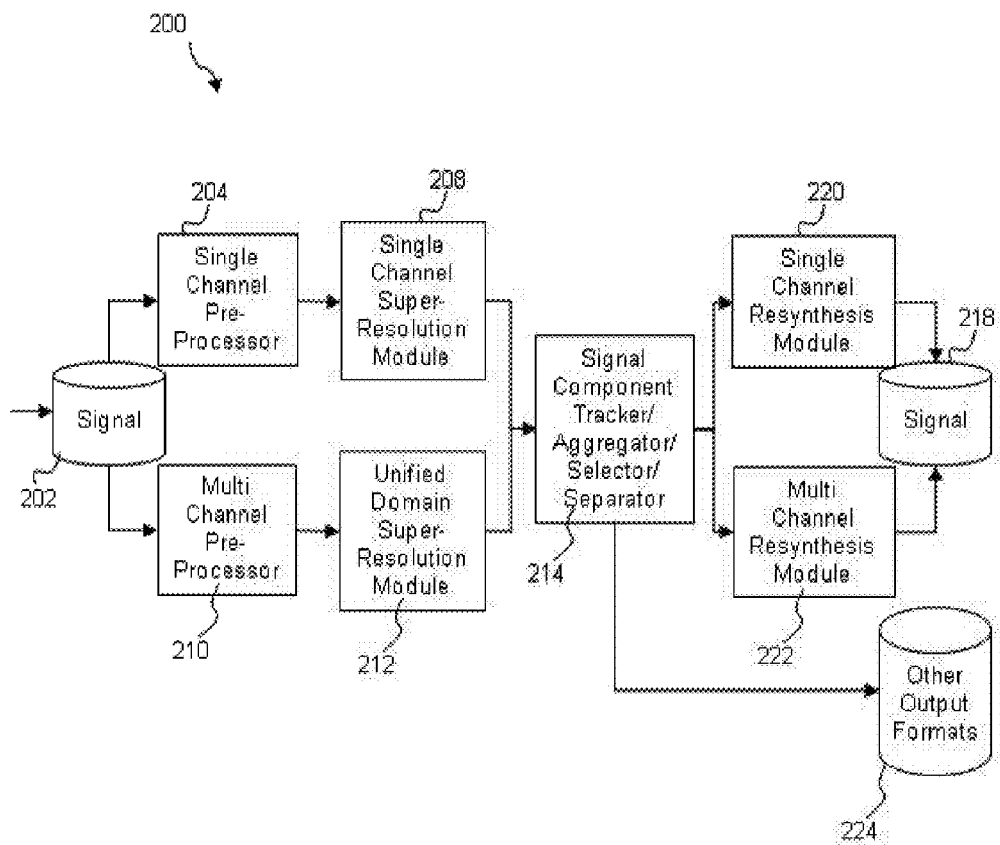
FIG. 2 illustrates signal extraction processing steps according to an exemplary and non-limiting embodiment.

FIG. 2 illustrates an embodiment of a SS system 200 that may be configured to separate the source signal 202 into the plurality of elements. In accordance with one or more embodiments, the SS system 200 may be configured to include one or more components such as a single channel pre-processor 204, a single channel super-resolution module 208, a multi-channel pre-processor 210, multi-channel super-resolution module 212, tracker/aggregator/selector/separator 214, single channel re-synthesis module 220, and a multi-channel re-synthesis module 222. These components may be implemented in hardware, software, or programmable hardware such as a Field Programmable Gate Array (FPGA).

The single channel pre-processor 204 may facilitate in pre-processing (e.g., preparation) of a single-channel time domain signal that may be processed by the single channel super-resolution module. The single channel super-resolution module 208 may facilitate in detection of a set of oscillator peaks in a signal that has been prepared by the single channel pre-processor. The multi-channel pre-processor 210 may facilitate in pre-processing (e.g., preparation) of a multi-channel time domain signal that may be processed by the multi-channel super-resolution module 212. The multi-channel super-resolution module 212 may facilitate in detection of a set of oscillator peaks in signal that has been prepared by the multi-channel pre-processor. In one or more embodiments, the single channel or the multi-channel pre-processors may be combined such as to operate as a single component of the system.

The tracker/aggregator/selector/separator ("TASS") 214 may be configured to group, separate, and/or select the subset of oscillator peaks. The single channel re-synthesis module 220 may be configured to produce a frequency domain signal from the set of oscillator peaks. The multi-channel re-synthesis module 222 may be configured to produce a multi-channel frequency domain signal from the set of oscillator peaks, including any number of channels. In one or more embodiments, the re-synthesis may be described as being produced by the single channel module or the multi-channel module, but these may be combined such as to operate as a single component of the system.

In accordance with one or more embodiments, the system 200 may be configured to utilize or include varying forms of algorithms, implemented in hardware, software or a combination thereof, customized for specific applications including but not limited to audio, video, photographic, medical imaging, cellular, communications, radar, sonar, and seismic signal processing systems. As illustrated in FIG. 2, a signal 202 may be received. The signal 202 may include data associated with a live-feed such as ambient sound, or prerecorded data, such as a recording of a noisy environment. The received signal 202 may be categorized as a single channel signal or a multi-channel signal. If the signal 202 has a single channel of data, such as a mono audio signal, the data associated with the signal 202 may be converted to the frequency domain with the single channel pre-processor 204. Further, one or more oscillator peaks may be identified in the frequency domain signal using the single channel super resolution module 208.

Conversely, the signal 202 may be converted to the frequency domain using the multi-channel processor 210 if the signal has multiple channels of data, such as a stereo audio signal. Further, the frequency domain signal may be communicated to the unified domain super resolution module 212 where a unified domain transformation of the frequency data may be performed and (super-resolution) oscillator peaks in the unified domain frequency data may be identified.

In accordance with one or more embodiments, TASS module 214 may be utilized to identify discrete signal sources by grouping peaks and to aggregate oscillator peaks to isolate desired discrete sources. The TASS module 214 may be configured to select one or more coherent groups from the aggregated oscillator peaks. Accordingly, the one or more coherent groups of peaks may be separated and delivered as an output in one or more formats to one or more channels.

In accordance with one or more embodiments, an output signal may be re-synthesized using the components as illustrated in FIG. 2. As an example and not as a limitation, the oscillator peaks may be converted to a re-synthesized signal 218 using the single channel re-synthesis module 220 if the source signal 202 is an originally single-channel signal. The re-synthesized signal 218 may also be referred herein to as a single channel signal generated using the single channel re-synthesis module 220. Similarly, the oscillator peaks may be converted to generate the re-synthesized signal 218 using the multi-channel re-synthesis module 222 if the source signal 202 is an originally multi-channel signal. The re-synthesized signal 218 may also be referred herein to as a multi-channel signal when generated using the multi-channel re-synthesis module 222. As illustrated, signal information may be outputted in the compact form of the analysis parameters; and/or the signal may be outputted directly into another format, such as one that can be achieved by a mathematical transformation from, or reinterpretation of, the analysis parameters. In other embodiments, the signal information may be outputted as feature vectors that may be passed directly to another application, such as a speech recognizer or a speaker identification system.

In accordance with one or more embodiments, the single channel pre-processor 204 may be configured to facilitate preparation of single channel time domain signal data for processing by the Single Channel CSPE super resolution techniques using the single channel super resolution module 208. The input to the single channel pre-processor 204 is a single-channel time-domain signal that may be a live feed or a recorded file. In an example, a multi-channel data streams are processed by the multi-channel pre-processor 210 that may be configured to process at least more than one channels of the multi-channel data stream.

Conventional signal analysis systems generally use the DFT or FFT or the Discrete Cosine Transform (DCT) or related transform to convert time-domain signal data to the frequency-domain for signal analysis and enhancement. The techniques employed in the methods and systems for SS as disclosed herein may be configured to facilitate pre-processing of the signal 202 using two (or more) FFTs as building blocks, where the time-domain input to the second (or more) FFT is a set of samples that are time delayed with respect to the input to the first FFT.

Figure 3:
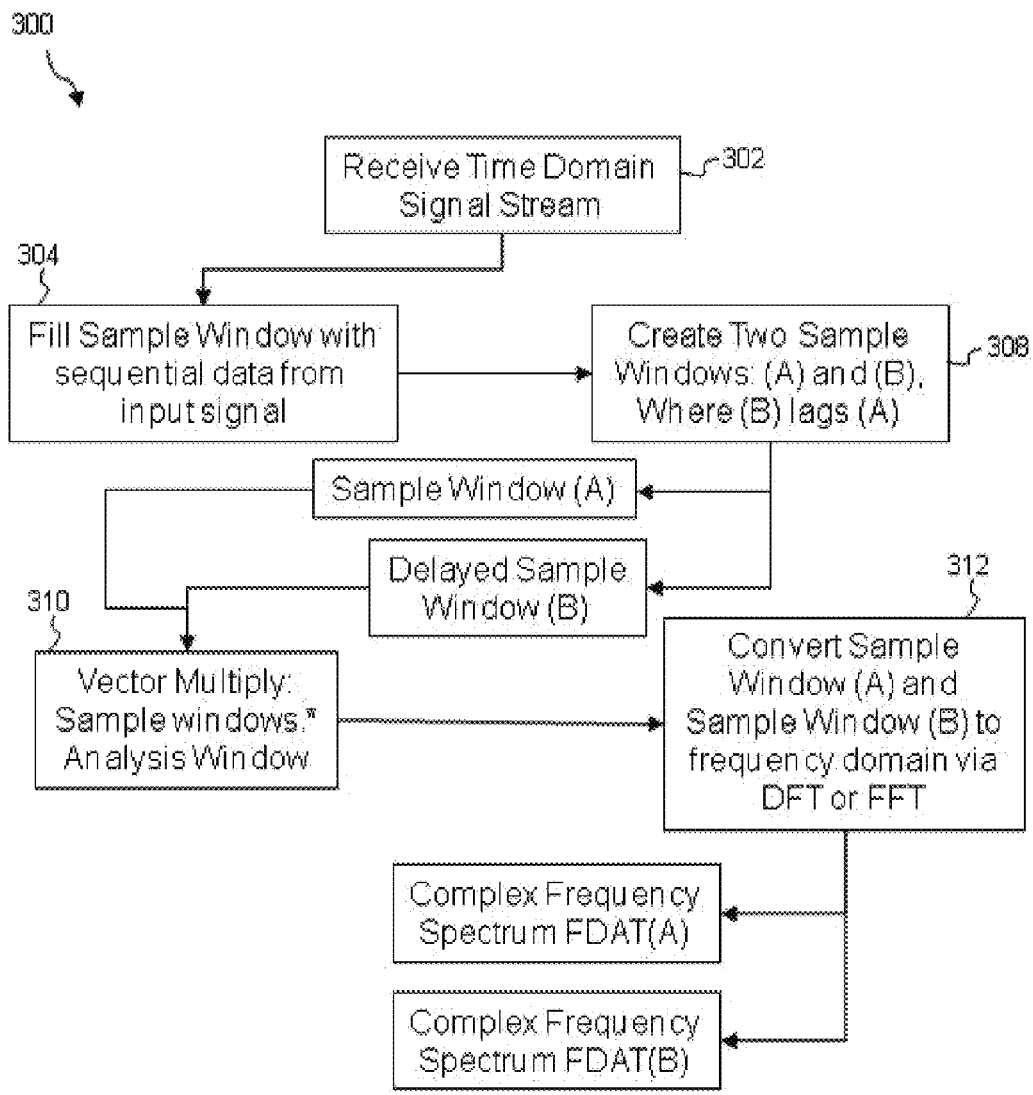
FIG. 3 illustrates a method for pre-processing the source signal using a single channel pre-processor according to an exemplary and non-limiting embodiment.

FIG. 3 illustrates an example embodiment of a method 300 for pre-processing the signal 202 using the single channel pre-processor 204. As illustrated, at step 302, the time domain signal stream may be received by the single channel pre-processor 204. At step 304, a sample window may be filled with n sequential samples of an input signal such as the signal 202. At step 308, two sampled windows such as a sample window A and a sample window B may be created. In an example, a size of the sample window A and a number of samples in the sample window A may overlap with subsequent and previous sample windows that may be specified by the user in a parameter file, or may be set as part of the software or hardware implementation. In an example, the sample window B may be referred herein to as a time-delayed sample window such that the sample windows A and B may offset in time and the sample window B may lag with sample window A.

At step 310, an analysis window (referred to herein as a taper) may be applied to the sample window A and sample window B such as to create a tapered sample window A and a tapered sample window B respectively. In an example, the analysis window may be applied using a Hadamard product, whereby two vectors are multiplied together pair wise in a term-by-term fashion. The Hadamard/Schur product is a mathematical operation that may be defined on vectors, matrices, or generally, arrays. When two such objects may have the same shape (and hence the same number of elements in the same positions), then the Hadamard/Schur product is defined as the element-by-element product of corresponding entries in the vectors, matrices, or arrays, respectively. This operation is defined, for instance, in a Matlab programming language to be the operator designated by ".*", and in the text below it will be represented either as ".*" or as the operator "⊙" in equations below. As an example, if two vectors are defined as $v_1=[a,b,c,d]$ and $v_2=[e,f,g,h]$, then the Hadamard/Schur product would be the vector $v_1 \odot v_2=[ae,bf,cg,dh]$. In another example, the analysis window may be chosen to be a standard windowing function such as the Hanning window, the Hamming window, Welch window, Blackman window, Bartlett window, Rectangular/Boxcar window, or other standard windowing functions, or other similar analysis window of unique design. At step 312, the tapered sample windows A and B may be converted to a frequency domain using a DFT or FFT or the Discrete Cosine Transform (DCT) or related transform. As a result, FDAT (A) and FDAT (B) may be generated on conversion such that the FDAT (A) and FDAT (B) are in a complex form.

Figure 4:
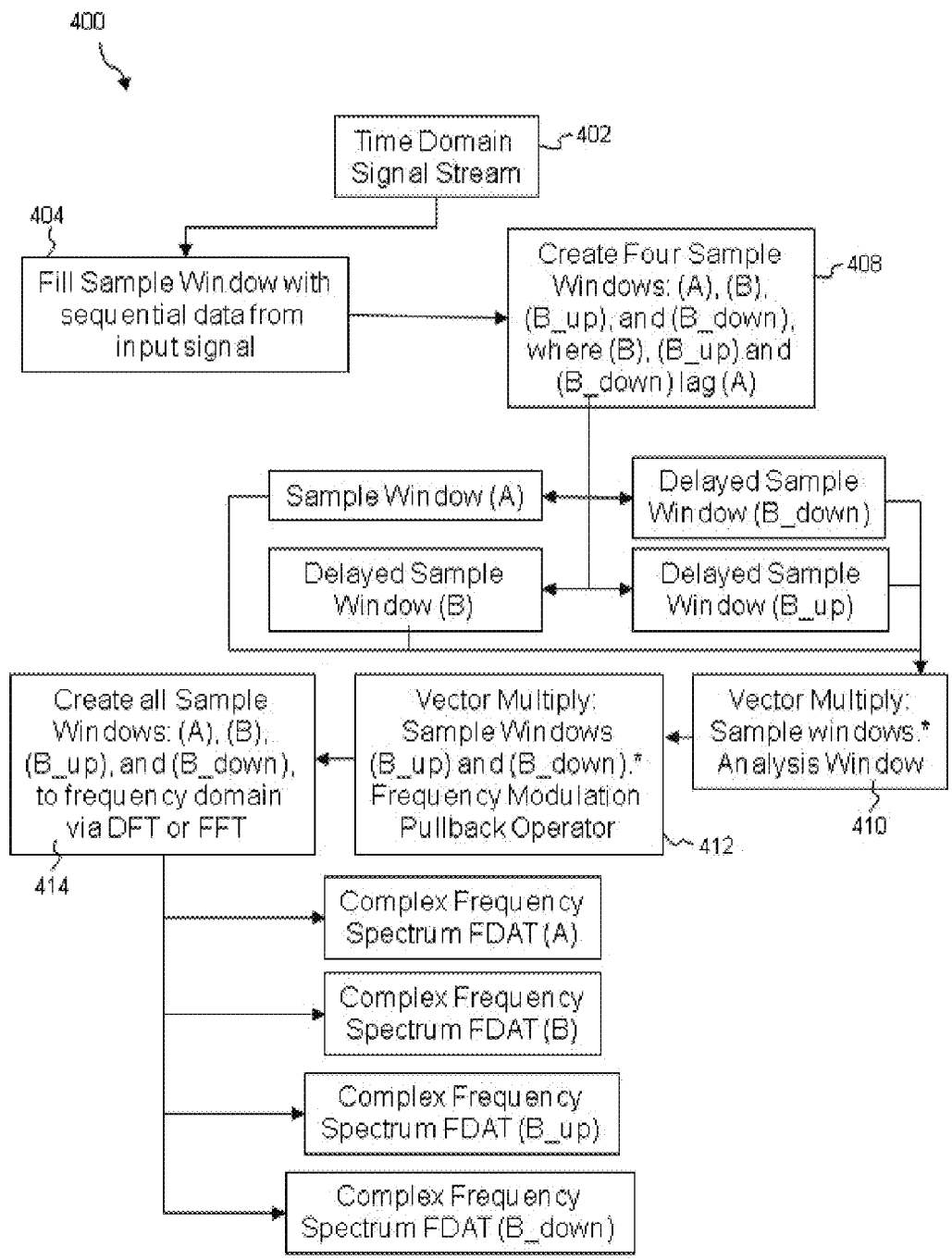
FIG. 4 illustrates a method for pre-processing the source signal using the single channel pre-processor to detect frequency modulation within the signal according to an exemplary and non-limiting embodiment.

FIG. 4 illustrates an example embodiment of a method 400 for pre-processing the signal 202 using the single channel pre-processor 204 when frequency modulation detection is required. As illustrated, at step 402, the time domain signal stream may be received by the single channel pre-processor 204. At step 404, a sample window may be filled with n sequential samples of an input signal such as the signal 202. At step 408, four sampled windows such as a sample window A, a sample window B, a sample window (B_up) and a sample window (B_down) may be created. In an example, the sample window (B_up) and the sample window (B_down) may include the same samples as the (B) window, but may be processed differently. In an example, a size of the sample window A and a number of samples in the sample window A may overlap with subsequent and previous sample windows that may be specified by the user in a parameter file, or may be set as part of the software or hardware implementation. In an example, the sample window B may be referred herein to as a time-delayed sample window such that the sample windows A and B may offset in time and the sample window B may lag with sample window A.

At step 410, an analysis window (referred to herein as a taper) may be applied to the sample window A and sample window B such as to create a tapered sample window A and a tapered sample window B respectively. At step 412, a modulation pullback operator may be applied to the sample window (B_up) and sample window (B_down) such as to create the tapered windows that can accomplish frequency modulation detection in the signal 202. In an example, the frequency modulation detection in the signal 202 may be accomplished via the Hadamard product between the sampled modulation pullback operator and the other samples such as the sample window (B_up) and sample window (B_down). For example, a sample window (B_up) may be used with the modulation pullback operator for detection of positive frequency modulation and a sample window (B_down) may be used with the modulation pullback operator for detection of negative frequency modulation. At step 414, all four tapered sample windows may be converted to a frequency domain using a DFT or FFT. As a result, FDAT (A), FDAT(B), FDAT(B_up) and FDAT(B_down) are created in a form of complex spectrum.

The aforementioned methods (e.g., methods 300 and 400) may further include analyzing an evolution of the complex spectrum from FDAT (A) to FDAT (B) and determining a local phase evolution of the complex spectrum near each peak in the complex spectrum. The resulting phase change may be used to determine, on a super-resolved scale that is finer than that of the FFT or DFT, an underlying frequency that produced the observed complex spectral phase evolution. The underlying frequency calculation is an example of super-resolution available through the CSPE method. Further, the method 400 can include analyzing the evolution of the complex spectrum from FDAT(A) to FDAT(B_down) and from FDAT(A) to FDAT(B_up) to detect the properties of down modulation and up modulation such as to detect presence of the frequency modulation in the signal 202.

The methods can further include testing the complex spectral phase evolution behavior of nearby points in the complex spectrum for each of the detected underlying frequencies. The testing may facilitate in determining whether the behavior of nearby points in the complex spectrum is consistent with the observed behavior near the peaks in the complex spectrum. Such approach may be applied to retain well-behaved peaks and reject inconsistent peaks. Similarly, for each individual modulating underlying frequency, the methods can include testing the complex spectral phase evolution behavior of nearby points in the complex spectrum to determine if they evolve in a manner that is consistent with the observed modulation behavior near the peaks.

The methods can further include conducting a deconvolution analysis to determine the amplitude and phase of the underlying signal component that produced the measured FFT or DFT complex spectrum for each consistent peak. Further, a reference frequency, amplitude, phase, and modulation rate for each consistent modulating peak of the underlying signal component that produced the measured FFT or DFT complex spectrum may be determined. The reference frequency is generally set to be at the beginning or at the center of a frame of time domain samples.

The aforementioned methods as implemented by the single channel pre-processor 204 creates at least two frequency domain data sets that can then be processed by single channel CSPE super resolution methods. As discussed, the time domain input to the second set lags the time domain input to the first set by a small number of samples, corresponding to a slight time delay. Each input is multiplied by the analysis window and is then transformed to the frequency domain by the DFT or FFT. The frequency domain output of the pre-processor will henceforth be referred to as FDAT (A) and FDAT (B). In addition, two additional frequency domain data sets such as FDAT (B_up) and FDAT (B_down) may be created if frequency modulation detection is required. FDAT (B_up) and FDAT (B_down) are frequency domain representations of the time delayed samples contained in the sample window (B) on which the modulation pullback operator is applied before conversion to the frequency domain. FDAT (B_up) has had a positive frequency modulation pullback operator applied, and FDAT (B_down) has had a negative frequency modulation pullback operator applied.

Thus, via the inputs, methods and outputs noted above, in accordance with an exemplary and non-limiting embodiment, a preprocessor receives a signal stream to create a set of data in the frequency domain, then creates a first set of input samples in the time domain and at least a second set of input samples in the time domain. The initiation of the second set of input samples time lags the initiation of the first set of input samples, thus creating two windows, the commencement of one of which is time-delayed relative to the other. The first and second sets of input samples are then converted to a frequency domain, and frequency domain data comprising a complex frequency spectrum are outputted for each of the first and second sets of input samples. In some embodiments, the first and second sets of inputs samples are converted to the frequency spectrum using at least one of a DFT and a FFT or other transform. In yet other embodiments, optional transforms to detect frequency modulation may be applied to the time-delayed windows. In some embodiments a taper or windowing function may be applied to the windows in the time domain In some embodiments, the applied transforms may not output complex domain data. For example, application of a discrete cosine transform (DCT) tends to result in the output of real data not in the complex domain.

As is evident, the described pre-processing methods: (i) introduce the concept of a time lag between windows that allows one to perform CSPE and (ii) may utilize various transforms of the type that are typically applied to perform frequency modulation detection. By "time lag" it is meant that a second window starts and ends later than the start and end of the first window in an overlapping way. This time lag mimics the human brain's ability to store information.

In accordance with one or more embodiments, the single channel super resolution module 208 may be configured to obtain higher frequency accuracy to permit and use singlet representation methods to extract components of the original signal such as the signal 202. The single channel super resolution module 208 may be configured to use the following inputs such as to facilitate the extraction of components from the signal 202. The single channel super resolution module 208 may require input information such as at least two sets of frequency domain data (FDAT (A) and FDAT (B)) as generated by the single channel pre-processor 204, one or more parameters that may have been used while applying a tapering function to the sample window A and the sample window B, super-resolved analysis of the transform of the windowing function at a resolution that is much finer than the DFT or FFT transformation and the like. This information can be pre-computed because the functional form of the windowing function is known a priori and can be analyzed to generally any desired degree of precision. In addition, the single channel super resolution module 208 may require two additional sets of frequency domain data FDAT (B_up) and FDAT(B_down), as generated by the single channel pre-processor 204 for detection of the frequency modulation in the signal 202. Optionally, the single channel super resolution module 208 may use additional super-resolved analysis windows for detection and characterization of amplitude modulation and joint frequency/amplitude modulation.

Figure 5:
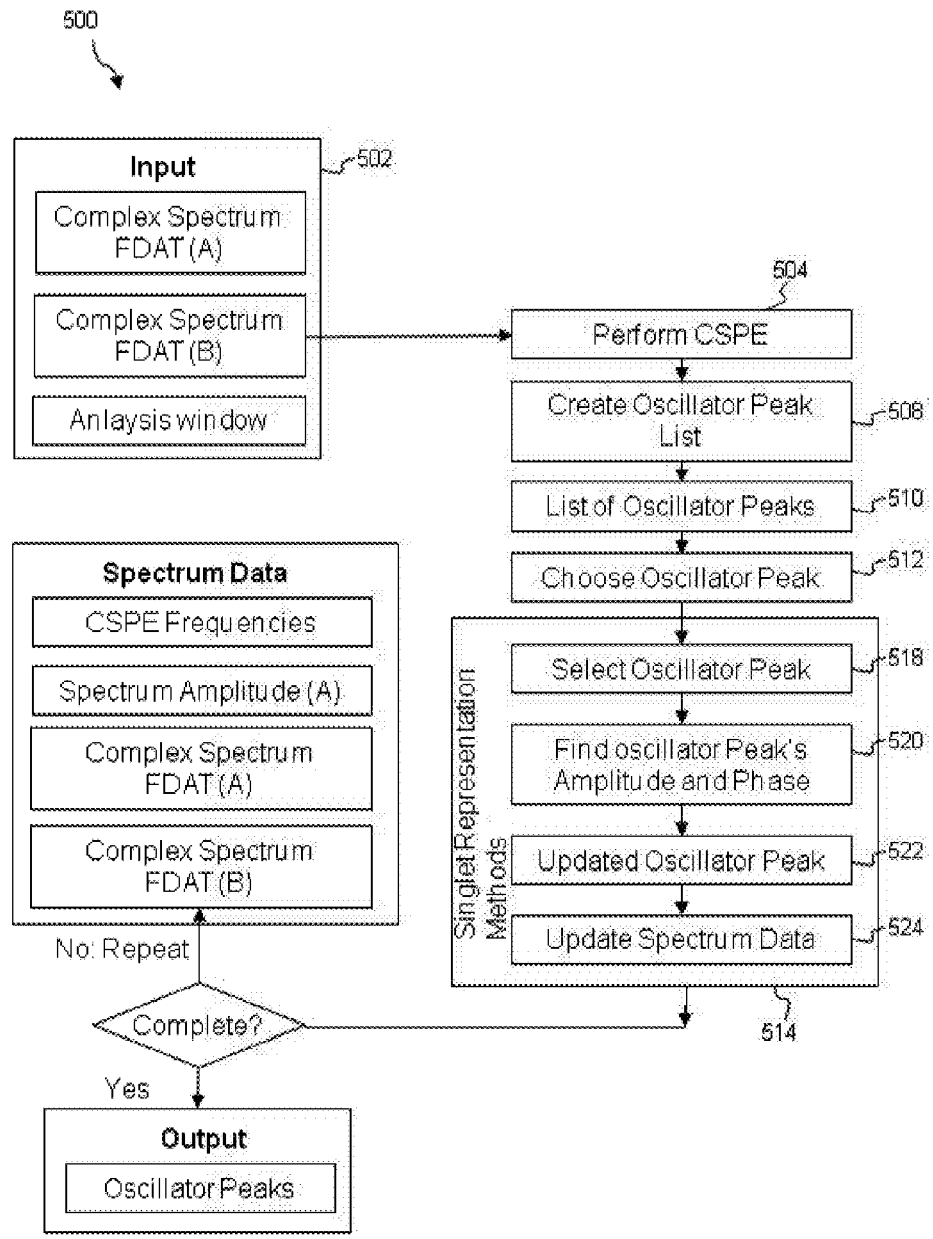
FIG. 5 illustrates a single channel super-resolution algorithm according to an exemplary and non-limiting embodiment.

FIG. 5 illustrates a method 500 for generating high accuracy frequency estimates such as to enable the extraction of a set of signal components. The single channel super resolution module 208 may be configured to utilize an input 502 that may include the two sets of frequency domain data (FDAT (A) and FDAT (B)) and the analysis window. At step 504, the single channel super resolution module 208 may be configured to calculate the complex spectral phase evolution to generate high resolution frequencies for subsequent signal extraction. At step 508, oscillator peaks in the complex Spectrum (FDAT(A) or FDAT(B)) are identified such as to generate a list of oscillator peaks 510. The oscillator peaks may be defined as the projection of an oscillator into the frequency domain and may be identified as local maxima at some stage in the processing process.

In an example, at step 512, the CSPE behavior of nearby points in the complex spectrum (FDAT(A) or FDAT(B)) may be tested for each of the identified local maxima such as to choose an oscillator peak. The testing may facilitate in determining whether the behavior of nearby points in the complex spectrum is consistent with the observed behavior near the peaks in the complex spectrum. Such approach may be applied to retain well-behaved peaks and reject inconsistent peaks. Similarly, for each individual modulating underlying frequency, the CSPE behavior of nearby points in the complex Spectrum may be tested such as to determine if they evolve in a manner that is consistent with the observed modulation behavior near the peaks. In an example, peak rejection criteria may be applied to discriminate targeted maxima generated by the main lobe of oscillators from non-targeted maxima generated by other phenomena such as unwanted noise or side lobes of oscillators. Further, extraction of targeted maxima by a variety of selection criteria may be prioritized. The variety of selection criteria may include but is not limited to, magnitude selection, frequency selection, psychoacoustic perceptual model based selection, or selection based on identification of frequency components that exhibit a harmonic or approximate harmonic relationship.

At step 514, one or more singlet representation methods may be used such as to generate an output. The one or more singlet representation methods may include determining the amplitude, phase, and optionally amplitude and frequency modulation of the oscillator peak 518 at step 520. In addition, the one or more singlet representation methods may include generation of the updated oscillator peak 522 and update of the spectrum data at step 524. The method may include removing the contribution of the oscillator peak from FDAT (A) and FDAT (B), and this may be done for any type of oscillator peak, including AM modulating and FM modulating oscillator peaks. The removal of the contribution may extend beyond the region of the maxima in FDAT(A) or FDAT(B) and separate out the smeared interference effect of the oscillator on other signal components that are present. Such type of removal process is a non-local calculation that may be enabled by the super-resolution analysis of the previous processing steps. Further, the singlet representation method may include consistent handling of the aliasing of signal components through the Nyquist frequency and through the DC (zero-mode) frequency.

At step 528, a determination is made as to whether the process is completed. That is to say, the determination of completion of the process may include whether an adequate number of targeted maxima are identified, signal components are prepared for tracking, and/or aggregation into coherent groups, and/or separation and selection, and/or re-synthesis. The single channel super resolution module 208 may be configured to repeat the processing steps using the spectrum data 530 if it is determined that the process is not completed. The method 500 proceeds to 532 if it is determined that the process is completed and at 532, oscillator peaks 534 are outputted for example, displayed to a user.

Figure 6:
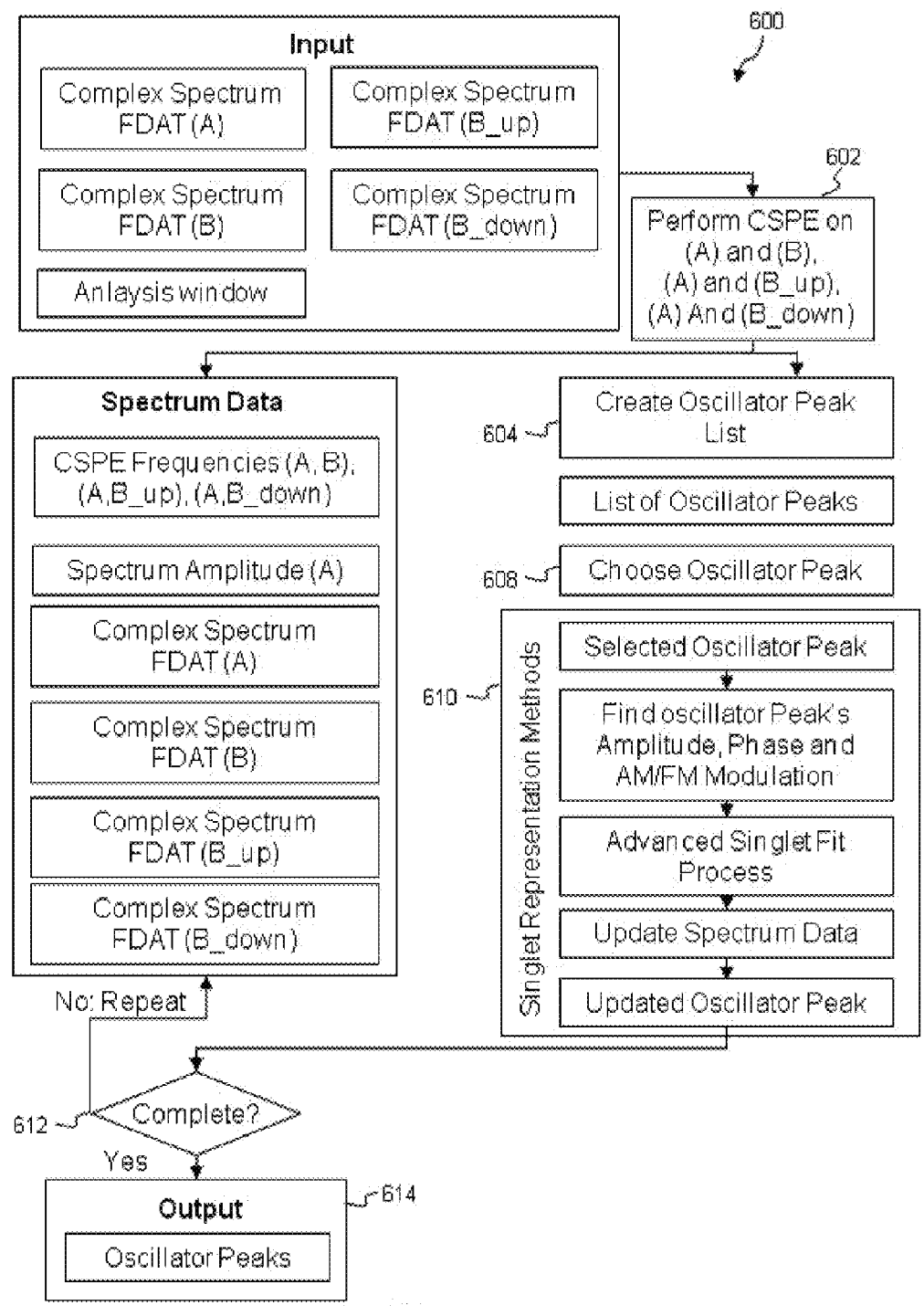
FIG. 6 illustrates a method for generating high accuracy frequency and AM and FM modulation estimates such as to enable the extraction of a set of signal components according to an exemplary and non-limiting embodiment.

FIG. 6 illustrates a method 600 for generating a high accuracy frequency and AM and FM modulation estimates such as to enable the extraction of a set of signal components. The method 600 may require two additional sets of frequency domain data FDAT (B_up) and FDAT(B_down) when compared to the data sets as required by the method 500. The additional sets of frequency domain data can enable the detection of AM and/or frequency modulation within the original signal 202. At step 602, the method 600 may perform CPSE on complex spectrum data such as FDAT(A), FDAT(B), FDAT (B_up) and FDAT (B_down). At step 604, an oscillator peak list may be created and at 608, oscillator peak is chosen using the techniques as disclosed in 508 and 512 of the method 500 respectively. At step 610, the method 600 may be configured to include one or more singlet representation techniques such to extract the components from the signal 202. These techniques are further disclosed in the description with reference to advanced singlet fit process. The method 600 may proceed to step 612 where a determination is made regarding completion of the process. On completion, at step 614, the method 600 may output the oscillator peaks.

Thus, in accordance with certain exemplary and non-limiting embodiments, taking the inputs and implementing the methods described herein, a processor receives a first set and a second set of frequency domain data, each having a given, or "fundamental," transform resolution, and the processor performs complex spectral phase evolution (CSPE), as further described herein, on the frequency domain data to estimate component frequencies at a resolution at very high accuracy, such accuracy being typically greater than the fundamental transform resolution. As used herein, "transform resolution" refers to the inherent resolution limit of a transformation method; for example, if a DFT or FFT is calculated on an N-point sample window taken from data that was sampled at Q samples per second, then the DFT or FFT would exhibit N frequency bins, of which half would correspond to positive (or positive-spinning) frequency bins and half would correspond to negative (or negative-spinning) frequency bins (as defined by a standard convention known to those familiar with the field); the highest properly sampled signal that can be detected in this method is a frequency of Q/2 and this is divided up into N/2 positive frequency bins, resulting in an inherent "transform resolution" of Q/N Hertz per bin. A similar calculation can be done for any of the other transformation techniques to determine the corresponding "transform resolution." In some embodiments there may further be performed peak selection comprising identifying one or more oscillator peaks in the frequency domain data, testing the CSPE behavior of at least one point near at least one of the identified oscillator peaks to determine well-behaved and/or short-term-stable oscillation peaks and performing an extraction of identified oscillator peaks. In yet other embodiments, one may further determine the amplitude and the phase of each identified oscillator peak and perform singlet transformation/singlet representation to map from a high resolution space to a low resolution space. In yet other embodiments, one may further perform singlet representation to remove a contribution of each identified oscillator peak from the frequency domain data.

As used above and herein, the "given," "original" or "fundamental" transform resolution is the resolution of the transform, such as the FFT, used to provide the input data set of frequency domain data—that is, the inherent resolution of the transform used as the fundamental building block of the CSPE. Additional details on the CSPE transformation itself follow.

The CSPE calculates higher accuracy estimates of frequencies than those produced by a conventional transformation, such as the standard DFT or FFT. Conventional FFT and DFT methods assume that the frequency estimate is located in the center of a frequency bin, whereas CSPE in accordance with one or more embodiments measures the rotation of complex phase of a signal over time to generate a high-resolution estimate of its location within a frequency bin. References to CSPE throughout this disclosure should be understood to encompass this capability to estimate characteristics of a signal, such as rotation of complex phase, at very high resolution within a frequency bin. In accordance with one or more embodiments, the CSPE method as disclosed herein may provide for a super-resolution frequency signal analysis. Generally, N samples are obtained from a signal for example, a digitally sampled signal from a music file in the .wav format, or an output of an analog-to-digital converter that may be attached to any sensor device, or a scan line of an image in black-and-white or RGB format and the like. A Fourier transform such as the Discrete Fourier Transform (DFT) or Fast Fourier Transform (FFT) is performed on the N samples of the signal (e.g., samples $1, \ldots, N$). Similarly, N samples are obtained from a time-delayed snapshot of the signal (e.g., samples $\tau+1, \ldots, \tau+N$ for a time delay t) and a Fourier transform is applied to these time delayed samples. The phase evolution of the complex Fourier transform between the original samples and the time-delayed samples is then analyzed. Particularly, the conjugate product of the transforms is obtained (with the multiply being a Schur or Hadamard product where the multiplication is done term-by-term on the elements of the first transformed vector and the complex conjugate of the second transformed vector) and then the angle of this conjugate product is obtained. Using this product and angle information, numerous advantageous applications may be realized. For example, the angle may be compared to the transforms to determine fractional multiples of a period such that the correct underlying frequency of the signal may be determined. Once the phase evolution is used to determine the correct signal frequency at much higher resolution than is possible with the original transform, it becomes possible to calculate a corrected signal power value. Further, the power in the frequency bins of the Fourier transforms may be re-assigned to, among other things, correct the frequency. In this case, the signal power that has smeared into nearby frequency bins is reassigned to the correct source signal frequency.

The CSPE algorithm may allow for the detection of oscillatory components in the frequency spectrum of the signal 202, and generally provide an improved resolution to the frequencies which may be in the transform. As stated above, the calculations can be done with the DFTs or the FFTs. Other transforms, however, can be used including continuous transforms and hardware-based transforms.

As shown in the following example, suppose a signal, s(t), is given and a digitally sampled version of the same signal, $\vec{s} = (s_0, s_1, s_2, s_3, \ldots)$ is defined. If N samples of the signal are taken, the DFT of the signal can be calculated by first defining the DFT matrix. For $W = e^{j2\pi/N}$ the matrix can be written as:

$$\mathbb{W} = \begin{bmatrix} 1 & 1 & 1 & 1 & \ldots & 1 \\ 1 & W & W^2 & W^3 & \ldots & W^{N-1} \\ 1 & W^2 & W^4 & W^6 & \ldots & W^{2(N-1)} \\ 1 & W^3 & W^6 & W^9 & \ldots & W^{3(N-1)} \\ \vdots & \vdots & \vdots & \vdots & \ddots & \vdots \\ 1 & W^{N-1} & W^{2(N-1)} & W^{3(N-1)} & \ldots & W^{(N-1)(N-1)} \end{bmatrix}$$

Each column of the matrix is a complex sinusoid that is oscillating an integer number of periods over the N point sample window. In accordance with one or more embodiments, the sign in the exponential can be changed, and in the definition of the CSPE, the complex conjugate can be placed on either the first or second term.

For a given block of N samples, define $$\vec{S}_0 = \begin{bmatrix} s_0 \\ s_1 \\ s_2 \\ s_3 \\ \vdots \\ s_{N-1} \end{bmatrix}, \vec{S}_1 = \begin{bmatrix} s_1 \\ s_2 \\ s_3 \\ s_4 \\ \vdots \\ s_N \end{bmatrix},$$

and in general, $$\vec{s}_i = \begin{bmatrix} s_i \\ s_{i+1} \\ s_{i+2} \\ s_{i+3} \\ \vdots \\ s_{i+N-1} \end{bmatrix},$$

the DFT of the signal can be computed as $$F(\vec{s}_i) = \begin{bmatrix} 1 & 1 & 1 & 1 & \ldots & 1 \\ 1 & W & W^2 & W^3 & \ldots & W^{N-1} \\ 1 & W^2 & W^4 & W^6 & \ldots & W^{2(N-1)} \\ 1 & W^3 & W^6 & W^9 & \ldots & W^{3(N-1)} \\ \vdots & \vdots & \vdots & \vdots & \ddots & \vdots \\ 1 & W^{N-1} & W^{2(N-1)} & W^{3(N-1)} & \ldots & W^{(N-1)(N-1)} \end{bmatrix} \begin{bmatrix} s_i \\ s_{i+1} \\ s_{i+2} \\ s_{i+3} \\ \vdots \\ s_{i+N-1} \end{bmatrix}$$

As described above, the CSPE may analyze the phase evolution of the components of the signal between an initial sample of N points and a time-delayed sample of N points. Allowing the time delay be designated by $\Delta$ and the product of $F(\vec{s}_i)$ and the complex conjugate of $F(\vec{s}_{i+\Delta})$, the CSPE may be defined as the angle of the product (taken on a bin by bin basis, equivalent to the ".*" operator in Matlab, also known as the Schur product or Hadamard product) CSPE=$\sphericalangle$(F($\vec{s}_i$)$\odot$F*($\vec{s}_i$)), where the $\odot$ operator indicates that the product is taken on an element-by-element basis as in the Schur or Hadamard product, and the $\sphericalangle$ operator indicates that the angle of the complex entry resulting from the product is taken.

To illustrate this exemplary process on sinusoidal data, take a signal of the form of a complex sinusoid that has period p=q+δ where q is an integer and δ is a fractional deviation of magnitude less than 1, i.e., $|\delta|\leq 1$. The samples of the complex sinusoid can be written as follows:

$$\vec{s}_0 = \begin{bmatrix} e^0 \\ e^{i2\pi \cdot \frac{q+\delta}{N}} \\ e^{i2\pi \cdot 2\frac{q+\delta}{N}} \\ e^{i2\pi \cdot 3\frac{q+\delta}{N}} \\ \vdots \\ e^{i2\pi \cdot (N-1)\frac{q+\delta}{N}} \end{bmatrix}$$

If one were to take a shift of one sample, then $\Delta=1$ in the CSPE, and:

$$\vec{s}_i = \begin{bmatrix} e^{i2\pi \cdot \frac{q+\delta}{N}} \\ e^{i2\pi \cdot 2\frac{q+\delta}{N}} \\ e^{i2\pi \cdot 3\frac{q+\delta}{N}} \\ e^{i2\pi \cdot 4\frac{q+\delta}{N}} \\ \vdots \\ e^{i2\pi \cdot N\frac{q+\delta}{N}} \end{bmatrix}$$

which can be rewritten to obtain:

$$\vec{s}_i = \begin{bmatrix} e^{i2\pi \cdot \frac{q+\delta}{N}} \\ e^{i2\pi \cdot 2\frac{q+\delta}{N}} \\ e^{i2\pi \cdot 3\frac{q+\delta}{N}} \\ e^{i2\pi \cdot 4\frac{q+\delta}{N}} \\ \vdots \\ e^{i2\pi \cdot N\frac{q+\delta}{N}} \end{bmatrix} = e^{i2\pi \cdot \frac{q+\delta}{N}} \begin{bmatrix} e^0 \\ e^{i2\pi \cdot \frac{q+\delta}{N}} \\ e^{i2\pi \cdot 2\frac{q+\delta}{N}} \\ e^{i2\pi \cdot 3\frac{q+\delta}{N}} \\ \vdots \\ e^{i2\pi \cdot (N-1)\frac{q+\delta}{N}} \end{bmatrix} = e^{i2\pi \cdot \frac{q+\delta}{N}} \vec{s}_0$$

One determines the conjugate product (again, taken on an element-by-element basis) of the transforms, the result is:

$$F(\vec{s}_i) \odot F*(\vec{s}_{i+1}) = e^{-i2\pi \cdot \frac{q+\delta}{N}} F(\vec{s}_i) \odot F*(\vec{s}_i) = e^{-i2\pi \cdot \frac{q+\delta}{N}} \|F(\vec{s}_i)\|^2$$

The CSPE is found by taking the angle of this product to find that:

$$\frac{2\pi}{N} CSPE = \sphericalangle(F(\vec{s}_i) \odot F*(\vec{s}_i)) = 2\pi \cdot \frac{q+\delta}{N}$$

If this is compared to the information in the standard DFT calculation, the frequency bins are in integer multiples of $$\frac{2\pi}{N},$$

and so the CSPE calculation provided information that determines that instead of the signal appearing at integer multiples of $$\frac{2\pi}{N},$$

the signal is actually at a fractional multiple given by $q+\delta$. This result is independent of the frequency bin under consideration, so the CSPE may allow an accurate determination of underlying frequency no matter what bin in the frequency domain is considered. In looking at the DFT of the same signal, the signal would have maximum power in frequency bin $q-1$, $q$, or $q+1$, and if $\delta \neq 0$, the signal power would leak to frequency bins well outside the range of bins. The CSPE, on the other hand, may allow the power in the frequency bins of the DFT to be re-assigned to the correct underlying frequencies that produced the signal power. In accordance with one or more embodiments, the definition of the W matrix, the columns on the right are often interpreted as "negative frequency" complex sinusoids, since $$\begin{bmatrix} 1 \\ W^{N-1} \\ W^{2(N-1)} \\ W^{3(N-1)} \\ \vdots \\ W^{(N-1)(N-1)} \end{bmatrix} = \begin{bmatrix} 1 \\ W^{-1} \\ W^{-2} \\ W^{-3} \\ \vdots \\ W^1 \end{bmatrix}$$

similarly the second-to-last column is equivalent to $$\begin{bmatrix} 1 \\ W^{-2} \\ W^{-4} \\ W^{-6} \\ \vdots \\ W^2 \end{bmatrix}$$

The phrase 'negative frequency components' as used herein the description may indicate the projection of a signal onto the columns that can be reinterpreted in this manner (and consistent with the standard convention used in the field).

In accordance with one or more embodiments, the oscillator peak selection process as used in the methods 400 and 500 of the description, may facilitate in identification of maxima in the frequency domain spectra that are main-lobe effects of oscillators, and determination of an optimal order in which to extract the oscillator peaks from the frequency domain data. In an example, the oscillator peak selection process may include converting the complex frequency data stored in FDAT (A) to an amplitude. The amplitude of an element of FDAT (A) is the absolute value of the complex value of that element. The amplitude of an element of the FDAT (A) may also be referred herein to as spectrum amplitude (A).

The oscillator peak selection process can include identifying local maxima in the spectrum amplitude (A). In an example, an element at location n is a local maximum if the amplitude at the location n is greater than the amplitude of the element at location n−1 and the amplitude of the element at location n+1. Further, the local maxima may be tested such as to identify main-lobe effects of the oscillators that are referred herein to as the oscillator peaks. For example, the amplitude of the local maxima may be tested against a minimum threshold value. In another example, proximity of the CSPE frequency corresponding to the location of the local maxima is determined with respect to the center of the FFT frequency bin corresponding to that location. If the CSPE frequency is not proximate enough, this may signify that the local maximum is a side-lobe effect of an oscillator or is a noise-induced peak. However, if the amplitude of the local maxima is greater than a certain threshold, the local maxima may be considered to be a significant peak regardless of earlier tests and may be constructed from a group of oscillators.

The oscillator peak selection process can include determining an order in which to extract oscillator peaks from the FDAT (A) and FDAT (B). Higher priority peaks are chosen using selection criteria appropriate for a given application; that is, for example, certain types of higher order peaks are typically more characteristic of desired signals, rather than noise, in given situation. Peaks may be chosen by, among other techniques, magnitude selection, a psycho-acoustic perceptual model (such as in the case of signal extraction for speech recognition or speech filtering), track duration, track onset times, harmonic associations, approximate harmonic associations or any other criteria appropriate for a given application.

In accordance with one or more embodiments, the CSPE high resolution analysis may be configured to convert tone-like signal components to structured (e.g., line) spectra with well-defined frequencies, while the noise-like signal bands do not generally take on structure. As such, the signal may be substantially segregated into the tone-like and the noise-like components. To select oscillator peaks, in embodiments a series of steps may be employed. For example, firstly, the CSPE analysis may test the complex spectral phase evolution behavior of nearby points in the complex spectrum for each individual underlying frequency detected such as to determine if they evolve in a manner that is consistent with the observed behavior near the peaks in the complex spectrum. Further criteria may be applied to retain well-behaved peaks and reject poorly behaved (e.g., inconsistent) peaks.

In an example, the CSPE analysis may be configured to conduct a deconvolution analysis for the each consistent, well-behaved peak such as to determine the amplitude and phase of the underlying signal component that produced the measured FFT or DFT complex Spectrum. The data obtained from the high resolution frequency analysis can be used to prioritize the components of the signal in order of importance; for example, priority in the case of recognition of speech signals in a noisy environment may be based on perceptual importance or impact on intelligibility. A psychoacoustic perceptual model (PPM) may be provided in the Unified Domain such that independent computations for each channel of data may not have to be computed separately, and the Unified Domain PPM may give information that may be used to give priority to specific components in the multi-channel data. In an example, the Unified Domain PPM may be used to give emphasis to signals coming from a specified direction or range of directions. Accordingly a Unified Psychoacoustic Perceptual Model (UPPM) is provided that incorporates the effects of spectral, spatial and temporal aspects of a signal into one algorithm. This algorithm may be embodied in hardware or performed in software.

In accordance with one or more embodiments, the UPPM computation may be separated into three steps. The first step may include a high resolution signal analysis that may distinguish between tone-like and noise-like signal components. The second step may include calculation of the coherency groups of signal components based on frequency, sound pressure level, and spatial location, with each coherency group providing a "unit of intelligibility" that may be enhanced. Further, the interference and separability of the coherency groups may be calculated and projected to create a Coherency Surface in the Unified Domain. In an example, the Coherency Surfaces may be utilized to create a surface that is defined over the entire spatial field. In addition, Coherency Curves can be obtained with a transformation from the Unified Domain for stereo audio signals, left and right channel. Thus, a traditional single-channel processing techniques can still be performed on a signal. At any time, a multi-channel signal can be transformed back into the Unified Domain or a signal in the Unified Domain can be transformed into a multi-channel signal (or a single-channel signal) for signal processing purposes.

In accordance with one or more embodiments, the singlet representation method may include a set of operations that can identify the parameters of an oscillator from frequency domain data, or can generate frequency domain data using the parameters of an oscillator. Various steps in the singlet transformation process in accordance with one or more embodiments may include calculating the normalized shape of the projection of an oscillator in the frequency domain. Further, the steps may include calculating the magnitude and phase of an oscillator by fitting the calculated spectrum to a set of frequency data and calculating the magnitude and phase of a low frequency oscillator, accounting for interference effects caused by aliasing through DC. In addition, the steps may include adding or subtracting an oscillator's frequency domain representation to or from frequency domain data, accounting for aliasing though Nyquist and DC. In accordance with one or more embodiments, complex analysis methods may be employed to further characterize an oscillator peak's frequency and amplitude modulation within a single FFT window. These complex algorithms are discussed further in detail in the description.

In accordance with one or more embodiments, a normalized shape of the oscillator's projection in the frequency domain may be calculated using an input including a high resolution frequency domain version of the analysis window used in the single channel pre-processor 204 and a high-accuracy frequency estimate of an oscillator peak, as created by CSPE. The high resolution frequency domain version of the analysis window used in the single channel pre-processor 204 may also be referred herein to as FWIN. The FWIN is the frequency domain representation of a high-resolution version of the analysis window used in the single channel pre-processor 204 such as to apply a taper to the sample window A and sample window B. The FWIN may be longer than the original analysis by a factor of 16 or 32. This factor is called the 'upsample' rate. In other embodiments, the high-resolution version of the analysis window may be known exactly through a mathematical functional representation.

If it is determined that the frequency of the oscillator is in the center of the FFT bin, the shape of the oscillator's projection matches a down-sampled version of FWIN, and can be created by first choosing a pointer from FWIN at its center, then choosing points at intervals of the upsample rate. If the frequency is not in the center of the FFT bin, the shape of the oscillator may correspond to a subset of FWIN slightly offset in frequency from those points. In accordance with one or more embodiments, the shape of an oscillator's projection into the frequency domain may be created using a method that may include calculating the distance in frequency between the center of the FFT bin corresponding to this location and the CSPE frequency. The method may further include choosing a first sample from FWIN at the FWIN's center plus the offset as calculated above. The method may include a calculation step choosing samples from FWIN at predetermined intervals based on upsample rate. For example, if the calculated offset corresponds to five bins in FWIN, the upsample rate is 16, and FWIN's center bin corresponds to 32769, then the FWIN bins chosen may be: [ . . . , 32741, 32757, 32773, 32789, 32805 . . . ]. In an example, the number of bins that may be chosen may depend on a user-defined parameter of the system. The output of this step is a set of complex samples chosen from FWIN and these complex samples may be referred herein to as the oscillator peak normalized spectrum. These samples may have inaccurate amplitude and phase.

In accordance with one or more embodiments, accurate amplitude and phase of the complex samples chosen from FWIN may be calculated on determination of the peak shape of the oscillator. In an example, the amplitude and phase calculation may be accomplished by fitting the oscillator's shape to a set of frequency domain data, typically stored in FDAT (A) and this phase may also be referred herein to as a Fit amplitude phase that may need an oscillator peak normalized spectrum, an oscillator peak's high accuracy frequency as calculated by CSPE, and a set of frequency domain data, typically FDAT (A). Further, the method may include solving for the magnitude and phase rotation that fits the spectrum data and multiplying sampled normalized spectrum by new magnitude and phase.

On estimation of the frequency of a signal component, an accurate approximation of the contribution of that signal component to the measured spectrum of a signal can be determined. In one or more embodiments, this follows from a property of the discrete Fourier Transform when applied to signals that are not centered in the middle of a frequency bin. This process follows from the properties of convolution and windowing. In other embodiments, where the high-resolution version of the analysis window may be known exactly as mathematical functional representation, the convolutional properties may be calculated in a continuous fashion.

In accordance with one or more embodiments, when a signal is analyzed, a finite number of samples may be selected, and a transform may be computed. As an example and not as a limitation, a DFT may be applied on the signal. However, other transforms having similar properties and are well known to researchers familiar with the art may be applied on the signal. The transform of the window of data is generally preceded by a windowing step, where a windowing function, $W(t)$, is multiplied by the data, $S(t)$. Suppose $W(t)$ is called the analysis window (and later the windows of data can be reassembled using the same or different synthesis windows). Since the data is multiplied by the window in the time domain, the convolution theorem states that the frequency domain representation of the product of $W(t)*S(t)$ exhibits the convolution of the transforms, $\hat{W}(f)$ and $\hat{S}(f)$, where the notation indicates that these are the transforms of $W(t)$ and $S(t)$, respectively. If the high resolution spectral analysis reveals that there is a signal component of magnitude $M_0$ at a frequency $f_0$, then the convolution theorem implies an existence of a contribution centered at $f_0$ that is shaped like the analysis window, giving a term essentially of the form $M_0 \hat{W}(f-f_0)$. In a discrete spectrum, such as the spectrum calculated by the discrete Fourier transform, there is a finite grid of points that result in a sampled version of the spectrum. Thus, the contribution centered at $f_0$ described above is sampled on the finite grid points that are integer multiples of the lowest nonzero frequency in the spectrum. Equivalently, if the discrete Fourier transform is calculated for N points of data that has been properly sampled with a sample rate of R samples/sec, then the highest frequency that is captured is the Nyquist frequency of R/2 Hz and there will be N/2 independent frequency bins. This provides a lowest sampled frequency of (R/2 Hz)/(N/2 bins)=R/N Hz/bin. In addition, all other frequencies in the discrete Fourier transform are integer multiples of R/N.

Because of the relationship between the analysis window transform, $\hat{W}(f)$ and the spectral values that have been sampled onto the frequency grid of the discrete transform, such as the discrete Fourier transform, it is possible to use knowledge of $\hat{W}(f)$, along with the measured sample values on the grid points nearest to $f_0$, to calculate a good estimate of the magnitude, $M_0$. To calculate this value, the nearest frequency grid point to $f_0(f_{grid})$ is identified, a difference $\Delta f=f_0-f_{grid}$ is calculated, and the magnitude value of the transform of the signal at that grid point $M_{grid}$ is calculated. The true magnitude can then be calculated from the following relation $$\frac{M_{grid}}{\|\hat{W}(-\Delta f)\|} = \frac{M_0}{\|\hat{W}_{max}\|}$$

In an example, $$\|\hat{W}_{max}\|$$

is taken to mean the maximum magnitude of the transform of the analysis window, and is generally normalized to 1. Also, the transform of the analysis window is generally symmetric, so the sign of $\Delta f$ generally does not matter. These relations can be adapted for more unusual windowing functions by those skilled in the art by manipulation of the basic convolution relation. Assuming a fixed resolution to the knowledge of $\hat{W}(f)$, $\hat{W}(f)$ can be sampled on a fine-scaled grid that is 2 times, 4 times, 8 times, 16 times, 32 times, or 64 times, or N times finer than the resolution of the frequency grid in the DFT. In this case, the difference value $\Delta f$ is calculated to the nearest fraction of a frequency bin that may correspond to the fine-scaled grid. For example, if the fine scaled grid is 16 times finer than the original frequency grid of the transform, then $\Delta f$ is calculated to $\frac{1}{16}$ of the original frequency grid. The desired fine-grained resolution is dependent on the particular application and can be chosen by one skilled in the art.

In accordance with one or more embodiments, the phase of the true signal may be adjusted on estimation of the true signal frequency and magnitude so that the signal may align with the phases that are exhibited by the discrete frequency spectrum. So, if $\phi_{grid}$ represents the phase angle associated with the magnitude $M_{grid}$, and $\phi_{win}$ represents the phase angle of $\hat{W}(-\Delta f)$, then the analysis window must be rotated by an amount that is equal to $\phi_{rot}=\phi_{grid}-\phi_{win}$. Once this is done, all of the information about the signal component is captured by the values of $f_0$, $M_0$, and $\phi_{rot}$. As a result, reconstruction of the signal component needs a representation of the analysis window, $\hat{W}(f)$, shifting of the representation to frequency $f_0$, rotating it by angle $\phi_{rot}$, and multiplying it by magnitude $M_0$ (assuming the analysis window has maximum magnitude equal to 1, otherwise multiply by a factor that scales the window to magnitude $M_0$). The output of fit amplitude and phase includes the oscillator peak's true amplitude and phase, and the oscillator peak's scaled spectrum.

In accordance with one or more embodiments, an accurate amplitude and phase may be calculated for a low frequency oscillator on determination of the peak shape of the oscillator. In such cases of the low frequency oscillator, the effect of aliasing through DC may interfere with the complex conjugate projection of that oscillator. Because of this interference, it is difficult to measure true amplitude and phase of the oscillator using conventional techniques. The methods presented here in accordance with one or more embodiments represent an innovation that solves the problem of calculating the true amplitude and phase of the low frequency oscillator. In an example, the method may include using an input that may include a low frequency oscillator peak's normalized spectrum, a low frequency oscillator peak's high accuracy frequency as calculated by CSPE, and a set of frequency domain data, typically FDAT (A) such as to determine the true amplitude and phase of the low frequency oscillator. In certain embodiments, the method may include an iterative step wherein CSPE frequency values are varied through a range of values to achieve an improved match to the oscillator's spectrum.

In signal processing applications, if data is sampled too slowly, then an aliasing problem at high frequencies may be present. Interference also exists at extremely low frequencies and will be referred to herein as the interference through DC problem. This problem occurs when finite sample windows are used to analyze signals. The windowing function used in the sampling is intimately involved, but the problem can occur in the presence of any realizable finite-time window function. To state the problem clearly, assume that a signal of frequency $f_0$ is present and is close to the DC or 0 Hz frequency state. If such a signal is sampled over a finite-time window W(t), then, as discussed above, the frequency spectrum of the signal is equal to the convolution in the frequency domain of a delta function at frequency $f_0$, with the Fourier transform of the windowing function, which is designated as $\hat{W}(f)$. In a discrete formulation, the result is then projected onto the grid of frequencies in the discrete transform, e.g., onto the frequency grid of the Fast Fourier Transform (FFT). Since the transform of the windowing function is not infinitely narrow, the spectrum has power spilling over into frequency bins other than the one that contains $f_0$. In fact, the transform of the windowing function extends through all frequencies, so some of the signal power is distributed throughout the spectrum causing a pollution of nearby frequency bins from the spillover of power. Depending on the windowing function, the rate at which $\hat{W}(f)$ falls to zero varies, but for most windows used in practice, e.g., Hanning windows, Hamming windows, Boxcar windows, Parzen windows and many others known to those skilled in the art, there is significant spillover beyond the bin that contains $f_0$. This spillover or smearing effect is important throughout the spectrum of a signal, and when two signal components are close in frequency, the interference from the spillover can be significant. However, the problem becomes acute near the DC bin, because any low frequency signal has a complex conjugate pair as its mirror image on the other side of DC. These complex conjugate signals are often considered as "negative frequency" components, but for a low frequency signal, the pairing guarantees a strong interference effect. However, the complex conjugate nature of the pairing allows for a solution of the interference problem to reveal the true underlying signal and correct for the interference, if a good estimate of the frequency can be achieved. The methods described herein address the problem of the conventional methods. The method may include considering the spectrum at $f_0$, and the measured spectral value at $f_0$ as a reflection of a contribution from the "positive frequency" component, which will be designated as $Ae^{i\sigma_1}$, and a contribution from the mirror image or "negative frequency" component, $Be^{i\sigma_2}$. Since the $Be^{i\sigma_2}$ contribution comes from the negative frequencies at $-f_0$, the contribution at $+f_0$ is taken from the conjugate of the analysis window $\hat{W}^*(f)$. If $\hat{W}^*(f)$ is assumed to be defined so that it is centered at f=0, then the contribution from the negative frequency component comes at a distance $2f_0$ from the center of $\hat{W}^*(f)$. Consequently, if a high resolution estimate of the frequency $f_0$, is obtained, then the contributions to the measured spectral value at $+f_0$ from positive and negative frequencies can be determined. The method can include setting the phase to be 0 at both the $+f_0$ and $-f_0$ positions. When set in this position, the values for $Ae^{i\sigma_1}$ and $Be^{i\sigma_2}$ are known completely, and so the difference $\sigma_1-\sigma_2$ is obtained. In addition, when the phase is 0, the signal components in the $+f_0$ and $-f_0$ positions are real, so the complex conjugate spectrum from the negative frequency is in the same relative phase position as the spectrum in the positive frequencies. However, when the phase becomes different from 0, the relative phase values must rotate in the opposite sense, so that if the phase at $+f_0$ is set to $\phi$, then the phase at $-f_0$ must be set to $-\phi$ to maintain the complex conjugate pairing. This means that in the zero phase orientation, the contributions $Ae^{i\sigma_1}$ and $Be^{i\sigma_2}$ have a relative phase difference of $\sigma_1-\sigma_2$, but as the phase orientation at $+f_0$ is set to $\phi$, the phase orientation at $-f_0$ counter-rotates and becomes set to $-\phi$, so the contribution $Be^{i\sigma_2}$ must counter-rotate by the same amount. Thus, in any phase orientation, the net contribution at a given frequency is a combination of rotated and counter-rotated versions of $Ae^{i\sigma_1}$ and $Be^{i\sigma_2}$, and these sums trace out an ellipse. Also, since the major axis of the ellipse will occur when $Ae^{i\sigma_1}$ and $Be^{\sigma_2}$ are rotated into alignment, this occurs when the rotation angle is $$\theta = \frac{1}{2}(\sigma_1 - \sigma_2)$$

and the sum of the rotated and counter-rotated versions becomes $$e^{\frac{-i}{2}(\sigma_1-\sigma_2)}(Ae^{i\sigma_1}) + e^{\frac{i}{2}(\sigma_1-\sigma_2)}(Be^{i\sigma_2}) = (A+B)e^{\frac{i}{2}(\sigma_1+\sigma_2)}.$$

As a result, the major angle occurs when the rotation and counter-rotation put the terms into alignment at an angle that is the average of the phase angles. The position of the minor axis can be similarly determined, since it occurs after a further rotation of $\pi/2$ radians. Thus, the sum of the rotated and counter-rotated versions for the minor axis becomes $$e^{i\frac{\pi}{2}}e^{\frac{-i}{2}(\sigma_1-\sigma_2)}(Ae^{i\sigma_1}) + e^{-i\frac{\pi}{2}}e^{\frac{i}{2}(\sigma_1-\sigma_2)}(Be^{i\sigma_2}) = (A-B)e^{\frac{i}{2}(\sigma_1+\sigma_2+\pi)}.$$

The method may further include facilitating parameterization of the ellipse so that the angular orientation can be determined in a straightforward manner. To start with, consider an ellipse with major axis on the x-axis and of magnitude M, and let S be the magnitude of the minor axis. The ellipse can then be parameterized by $\tau \rightarrow (M\cos\tau, S\sin\tau)$, and by specifying a value for $\tau$, any point on the ellipse can be chosen. If $\tau$ gives a point on the ellipse, and the angular position, $\rho$, of the point in polar coordinates (since this will correspond to the phase angle for the interference through DC problem), can be found from the relation $$\tan\rho = \frac{S\sin\tau}{M\cos\tau} = \frac{S}{M}\tan\tau.$$

When this form of parameterization is applied to the interference through DC problem, the ellipse formed by rotated and counter-rotated sums of $Ae^{i\sigma_1}$ and $Be^{i\sigma_2}$ is rotated so that the major and minor axes align with the x- and y-axes, and then the measured spectrum is examined to determine the actual angle exhibited by the resultant spectral components. The resultant angle from the measured spectrum is labeled $\Omega$. Since the major axis is at $$\Delta = \frac{1}{2}(\sigma_1 + \sigma_2),$$

a further rotation is needed to put the resultant at angle $\Omega$. Therefore, $\tau$ corresponding to $\Omega$-$\Delta$ needs to be determined, and in an example, is obtained using the following relation:

$$\tan(\Omega - \Delta) = \frac{A-B}{A+B}\tan\tau$$

provided as the result:

$$\tau = \tan^{-1}\left(\frac{A+B}{A-B}\tan(\Omega - \Delta)\right)$$

The method may further include recognizing that the relations above are determined solely from knowledge of the frequencies and complex conjugate relationship at the $+f_0$ and $-f_0$ positions in the spectrum. All of the analysis was determined from the relative magnitudes of the transform of the windowing function. The relative magnitudes will remain in the same proportion even when the signals are multiplied by an amplitude value. Therefore, the recreation of the true measured spectrum may require selecting the true amplitude value from the spectrum and then rescale the sum of the rotated and counter-rotated contributions so that they equal the amplitudes exhibited by the measured spectral values. The final result is a highly accurate measure of the true amplitude of the signal at $+f_0$, so that when the spectrum is reconstructed with the windowing function $\hat{W}(f)$ positioned at $+f_0$, and its mirror-image, complex conjugate pair, $\hat{W}^*(f)$, placed at $-f_0$, the resulting sum that includes the interference through the DC bin will be a highly accurate reconstruction of the true, measured signal spectrum.

The above analysis has focused on the interaction at the $+f_0$ and $-f_0$ positions in the spectrum and a similar analysis can be conducted at any of the affected frequencies to derive an equivalent result. The analysis at the $+f_0$ and $-f^0$ positions is for illustrative purpose since the signal is concentrated there, and in practice generally gives the highest signal to noise ratio and most accurate results. The output of fit amplitude and phase for low frequency oscillators is a low frequency oscillator peak's true amplitude and phase, and a low frequency oscillator peak's scaled spectrum.

In one or more examples, it may be determined that the estimate of $+f_0$ may not be sufficiently accurate. In these cases, it is possible to vary the value of $+f_0$ over a range of frequencies and continue to iterate the process until a desired accuracy is reached and is discussed further in detail in the description in a section [00150] below.

In accordance with one or more embodiments, some or all oscillator peaks that are fit using the low-frequency method are tested and corrected for error. The method of testing and correcting the low frequency oscillator peak error may include subtracting an oscillator peak from spectrum to which it was fit and calculating the residual spectrum. If the residual spectrum near the center of that oscillator peak is above a threshold, the method may include modifying the CSPE frequency at intervals on either side of the original spectrum, and repeating low frequency amplitude and phase calculations. Accordingly, the method may include using the oscillator peak with the lowest residual error. The method described in this section may be used in the process of frequency and amplitude modulation detection.

In accordance with one or more embodiments, interference by an oscillator aliasing across DC or Nyquist should be accounted for when removing or adding an oscillator peak to or from frequency data such as to prevent the incorrect identification of peaks or re-synthesis of peaks. In an example, this can be accomplished by implementing a method for adding or subtracting the complex conjugate of the portion that wraps through DC or Nyquist in addition to the primary addition or subtraction. In an example, the method may include using an input that may include an oscillator peak's high resolution frequency as calculated by CSPE, an oscillator peaks' scaled spectrum, and a set of frequency domain data such as to perform oscillator peak addition and subtraction. The method can include identifying the location of the oscillator peak in the frequency domain data and dividing the oscillator peak into a primary region and a tail region if the oscillator peak is situated such that it is bisected by either the DC frequency or the Nyquist frequency. The tail region is the portion that lies in the negative frequencies between DC and −Nyquist (negative Nyquist) (where we adopt the convention that half of the frequencies in the complex FFT are designated positive (or positive-spinning) frequencies and half of the frequencies are designated negative (or negative-spinning) frequencies.

In an example, the method can include adding the primary region to the input frequency domain data and adding the complex conjugate of the tail region to the input frequency domain data when an additive operation is performed to prevent the incorrect identification of peaks or re-synthesis of peaks. Otherwise, the method can include subtracting the primary region from the input frequency domain data and subtracting the complex conjugate of the tail region from the input frequency domain data to prevent incorrect identification of peaks or re-synthesis of peaks. The method may output a modified set of the frequency domain data received as input to this step.

In accordance with one or more embodiments, the output of the single-channel super-resolution methods may include a set of parameters describing individual oscillator components. Each set may include the information used to accurately reconstruct that oscillator in the single channel re-synthesis methods. In a preferred embodiment, the information may include frequency, amplitude, and phase related information corresponding to the oscillator component.

In an example, the multi-channel pre-processor 210 may be configured, in accordance with one or more embodiments, to prepare multi-channel time domain signal data that may be processed by the multi-Channel CSPE super resolution techniques. In an example, as an input, a multi-channel time-domain signal may be fed to the multi-channel pre-processor 210. The input may be a live feed or a recorded file. In another example, single-channel data streams may be processed by the single-channel pre-processor.

The multi-channel pre-processor 210 may be configured to follow the same methods described as discussed previously for the single-channel preprocessor in 204, but the methods may be repeated for multiple channels of data. In an example, the multi-channel pre-processor 210 may perform a method for each channel of input signal in accordance with one or more embodiments. The method may include filling a sample window with n sequential samples of input signal for that channel. In an example, the sequential sample windows may be configured to overlap with each other such that the size of the sample window and number of samples that the sample window overlaps with subsequent and previous sample windows may be specified by the user in a parameter file. The size and number of overlapping sample window may also be set as part of a software or hardware implementation. For exemplary purposes a sample window may be defined, hereinafter referred to as Sample Window (A).

The method may further include creating a second, time-delayed sample window. For exemplary purpose, the second sample window may hereinafter be referred as Sample Window (B). The sample window A and the sample window B may be offset in time such that the sample window B lags the sample window A. Sample Window (B) lags Sample Window (A). The method may further include creating two more time-delayed sample windows if frequency modulation detection is desired. The additional sample windows may contain the same samples as the sample window B, but the additional windows may be processed differently. The additional windows may hereinafter be referred to as (B_up) and (B_down) for exemplary purpose. The detection of frequency modulation may include applying a 'Modulation Pullback Operator' to the (B_up) and (B_down) sample windows. This may be accomplished via a Hadamard product. For example, for the (B_up) sample window, a Modulation Pullback Operator for positive frequency modulation may be used. Further, for the (B_down) sample window, a Modulation Pullback Operator for negative frequency modulation may be used. The method may further include applying an analysis window, or taper, to both, the sample window A and the sample window B separately. This may be accomplished via the Hadamard product, as discussed previously. In an example, the frequency modulation detection may include applying the analysis window to the (B_up) and (B_down) sample windows. The method may further include converting both the tapered sample window A and the tapered sample window B to the frequency domain using a DFT or FFT. For exemplary purposes, the frequency domain output may hereinafter be referred to as FDAT_channel_X (A) and FDAT_channel_X (B), where X is the identifier of the channel. Further, if frequency modulation detection may be desired, the FDAT_channel_X (B_up) and FDAT_channel_X (B_down) windows may be created using the same process as discussed previously for the (B_up) and (B_down) sample windows.

In an example, an output of the multi-channel pre-processor 210 may include two sets of data per frame, such that each data set may have been converted to the frequency domain via the Fast Fourier Transform (FFT) technique or any other related frequency transform technique. For each channel, the second set may lag the first set by a small number of samples, corresponding to a slight time delay. For the exemplary purpose of description, these data sets may be referred as FDAT_channel_0 (A), FDAT_channel_0 (B) . . . FDAT_channel_N (A), and FDAT_channel_N (B). In an example, if frequency modulation detection is desired, two additional frequency domain data sets may be created for each channel. These may be hereinafter exemplarily referred to as the FDAT_channel_X (B_up) and FDAT_channel_X (B_down). FDAT_channel_X (B_up) and FDAT_channel_X (B_down) may be the frequency domain representations of the time delayed samples that may be contained in the sample window B and that may have had a Modulation Pullback Operator applied to them before conversion to the frequency domain. The FDAT_channel_X (B_up) may have a positive frequency Modulation Pullback Operator applied, and the FDAT_channel X (B_down) may have a negative frequency Modulation Pullback Operator applied.

In accordance with an exemplary and non-limiting embodiment, a preprocessor may receive a plurality of signal streams to create a set of data in the frequency domain. The frequency domain data may comprise a plurality of sample windows, or "data sets". For the purpose of description, the "Sample window" may refer to a window of n samples that may be taken from an original time series data. Each of the plurality of frequency domain data sets may then be used to create a first data set and a second data set wherein the initiation of the second data set time may lag the initiation of the first data set, and each of the plurality of sample data sets may be converted to a frequency domain and outputted as a complex frequency spectrum for each of the first and second data sets. In some examples, each corresponding first data set/window and second data set/window may be converted to the frequency spectrum, such as by using a conventional transform, such as a FFT, DCT, or any other such transform.

In an example, a multi-channel super resolution module may be defined. The multi-channel super resolution module may be configured to obtain a higher frequency accuracy to permit the use of singlet transforms to extract components of an original signal. In an example, the input of the multi-channel super-resolution module may include two sets for frequency domain data for each channel from the multi-channel pre-processor 210. The data set may be hereinafter referred to as an FDAT_channel_0 (A) and an FDAT_channel_0 (B). FDAT_channel_N (A), and FDAT_channel_N (B), where the channel is specified as channel_0 up to channel_N, and the frequency data is specified as (A) for non-time-delayed data and (B) for time-delayed data.

The input may further include parameters describing the analysis window used when applying a taper to the sample window A and the sample window B. In an example, if frequency modulation is desired, the input may further include two additional sets of frequency domain data, a data FDAT (B_up) and a data FDAT (B_down), as generated by the single channel pre-processor. In an example, the input may further include optional additional super-resolved analysis windows for detection and characterization of frequency and amplitude modulation.

Figure 7:
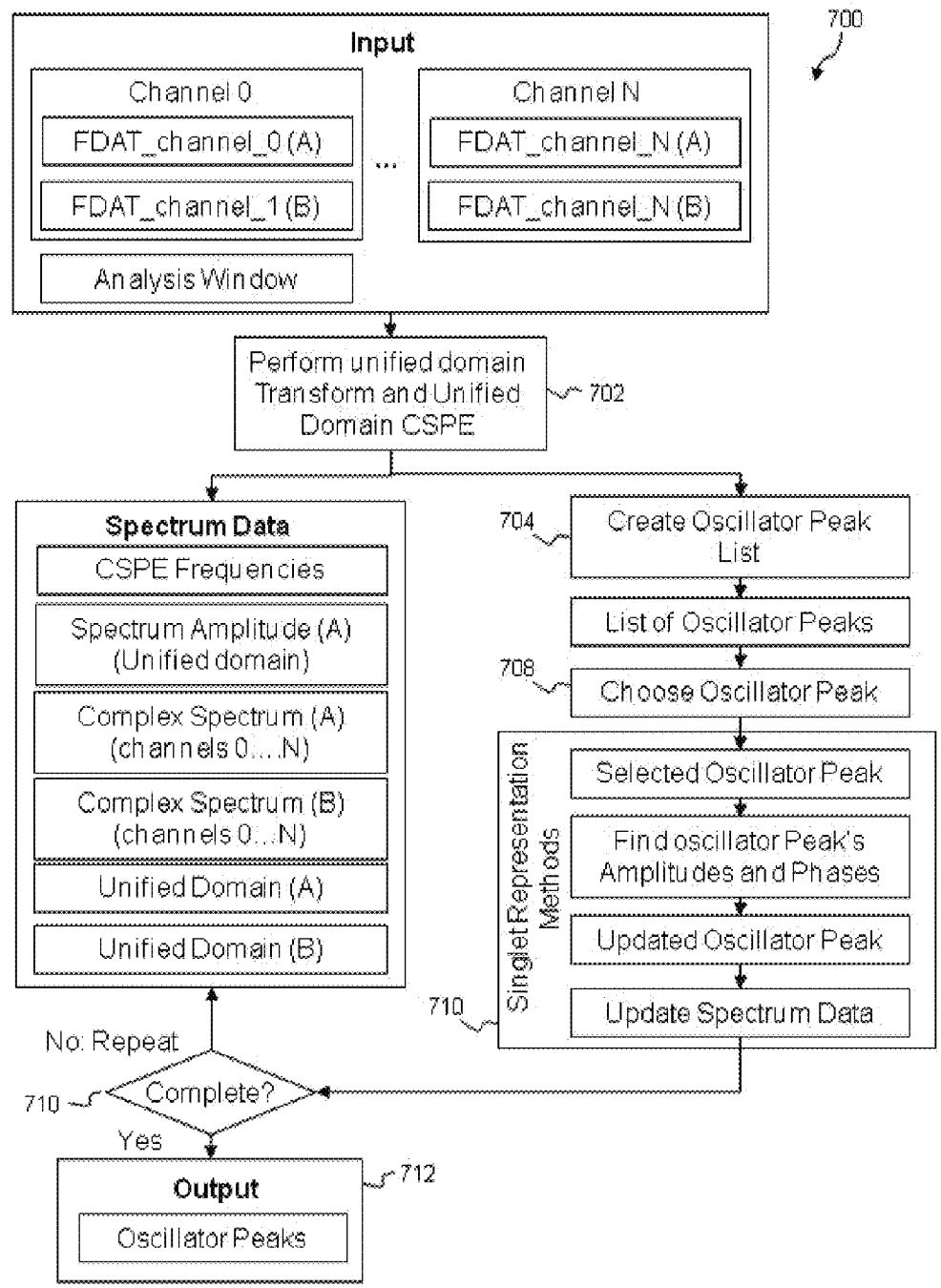
FIG. 7 illustrates an example of a method for unified domain super resolution according to an exemplary and non-limiting embodiment.

FIG. 7 illustrates a method 700 for unified domain super resolution. The method illustrates by way of example, performing signal decomposition in the Unified Domain by decomposing into discrete objects such as steady tones, noise-like elements, transient events, and modulating frequencies. The method 700 in accordance with one or more embodiments may be an extension of the single-channel super-resolution methods.

The method may include, at 702, performing unified domain transform and unified domain complex spectral phase evolution (CSPE) on complex spectral phase evolution frequencies obtained from the plurality of input channels. The input channels may include the channels input to the multi-channel super resolution module, such as the channels FDAT_channel_0 (A), FDAT_channel_0 (B) . . . FDAT_channel_N (A), and FDAT_channel_N (B) as discussed previously. The method 700 may further include using the singlet transform methods to remove the contribution of the oscillator peak from FDAT_channel_0 (A), FDAT_channel_0 (B) . . . FDAT_channel_N (A), FDAT_channel_N(B). This may be done at 704, by creating a list of oscillator peaks from the transformed channel data. Further, from the list of oscillator peaks, at 708, an oscillator peak may be chosen using a peak selection process. The peak selection process may include identifying oscillator peaks. The peak selection process may further include applying peak rejection criteria to discriminate targeted maxima generated by the main lobe of oscillators from non-targeted maxima generated by other phenomena such as unwanted noise or side lobes of oscillators. The targeted maxima may then be prioritized based on a plurality of factors including a magnitude and frequency of separation, an application of a psychoacoustic model, or tracker state information that may be used to prioritize peak selection. The method 700 may further include, at 710, using singlet transform methods to identify the amplitude and phase of the oscillator peak in each channel. The oscillator peak's information may be saved for an output from the process. The method 700 may further include, at 710, making a determination if the process may be complete. If the process is complete, at 712, the oscillator peak information saved previously may be provided as an output of performing the method 700. Alternatively, if at 712 it is determined that the process of identifying oscillator peaks is not complete, the method 700 may be repeated.

Figure 8:
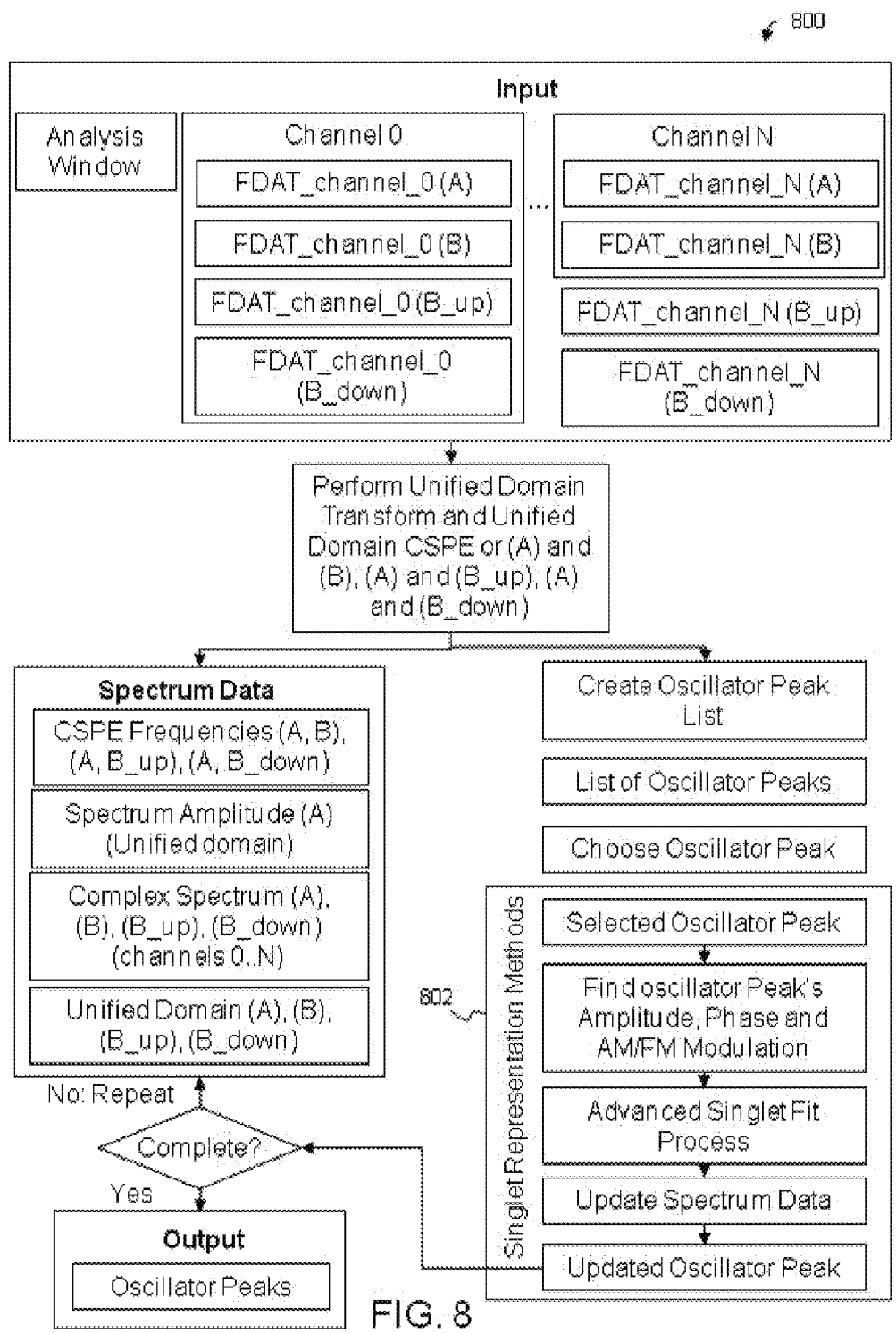
FIG. 8 illustrates an example of a method for unified domain super resolution with amplitude and frequency modulation detection according to an exemplary and non-limiting embodiment.

In an example, the method 700 may further include preparing signal components for tracking and/or filtering and/or re-synthesis. In an alternate embodiment, the method for unified domain super resolution may be used in conjunction with amplitude and frequency modulation detection. FIG. 8 illustrates such a method 800, which incorporates additional amplitude and frequency modulation detection at 802, apart from the steps included in the method 700. At 802, if amplitude and/or frequency modulation detection is desired, a technique involving the Advanced Fit Process is used.

s may be used to identify the frequency and/or amplitude modulation of the oscillator peaks that may have been chosen as previously discussed for method 700.

The unified domain representation of the spectrum data in accordance with one or more embodiments may be calculated using the techniques of which will be discussed in the following description.

Unified Domain may be a representation of multi-channel signals as a single channel of data. There may be lossless transformation that converts a multi-channel signal into a Unified Domain. As a result, a signal in the Unified Domain may be processed as a whole, rather than separately processing the individual channels. In an example, even when a signal is transformed into the Unified Domain, all of the signal's information about the magnitudes, frequencies, and spatial component related to a signals location may be retained. The transformation of the signal may be an invertible technique such that a signal in the Unified Domain may be reverted back to a multi-channel signal, such as a surround-sound signal, or a stereo signal of an RGB signal. In an example, the Unified Domain transformation may include a feature such that the original, multi-channel signal may be converted to a representation where a single magnitude component is multiplied by a matrix from the special unitary group, SU(N), where N represents the number of channels in the original data signal.

In an example, the process of converting to the Unified Domain (UD) may begin when a multi-channel signal stream may be converted to a single channel signal stream in the Unified Domain. A transformation may be utilized to perform the conversion. The transformation may include retaining information about the magnitudes, frequencies, internal phases, and spatial locations of the signal components of each channel while placing the information in a single "signal". Further, the transformation may include using a stream of matrices rather than a single, 1-dimensional stream of data samples. The UD transformation may be an invertible technique as the UD representation involves a single magnitude component multiplied by an element of the complex Special Unitary group for N-channels (SU(N)). In some examples, the UD matrix may be taken from the Unitary Group U(n). The SU(N) group may be represented in many ways. For the purposes of transforming a multi-channel signal, the structures of complex matrices may be employed. In an example, stereo input may be represented in UD. Since stereo input includes two channels, such that N=2, accordingly, the representation in the Unified Domain may be provided as a single magnitude component multiplied by a 2×2 complex matrix. More particularly, the transformation of a multi-channel audio stream may be represented as:

$$T: C^N \leftrightarrow mag * SU(N) \equiv U^N$$

$$[audio_{ch0} audio_{ch1} \ldots audio_{chN-1}] \leftrightarrow U^N$$

where the magnitude may be a function of frequency, N may represent the number of input channels, and U represents the Unified Domain.

For a conventional two channel audio stream (such as Left/Right) the representation may become:

$$[LR] \leftrightarrow U^2$$

This representation may include a one-to-one mapping between the two channel audio stream and the representation as a stream of matrices in the UD and the transformation may be lossless. Any manipulations done in one domain may have an equivalent counterpart in the other domain. Persons skilled in the art may appreciate that a number of processing techniques may be performed on a signal in the Unified Domain that may prove to be advantageous. For example, a process applied to a signal may be performed faster since the process may only have to be performed once in the Unified Domain, while the process would otherwise have to be performed separately for each sub-channel. Furthermore, Unified Domain manipulations have the advantage of operating on all of the channels at the same time, thus keeping the channels synchronized without the need for additional synchronization processes to be performed.

In accordance with exemplary and non-limiting examples, a processor may be configured to receive a plurality of channels, each comprising a first set and a second set of frequency domain data having a transform resolution. The plurality of channels may be combined into a unified domain representation and complex spectral phase evolution (CSPE) may be performed on the unified domain representation to estimate component frequencies at a resolution or accuracy greater than the fundamental transform resolution. In such examples, the mathematics discussed above may apply uniformly as CSPE turns the plurality of channels into a representation in the Unified domain. For example, instead of a right and left channel, CSPE may render a single matrix form representation including all of the inputted channels.

In other examples, further performing peak selection may be performed comprising identifying one or more oscillator peaks in the unified domain representation and testing the CSPE behavior of at least one point near at least one identified oscillator peak to retain well-behaved peaks. These identified peaks may then be extracted in prioritized fashion. In other examples, singlet representation may be performed to identify amplitude and phase of each identified oscillator peak. In yet other examples, singlet representation may be performed to remove a contribution of each identified oscillator peak from the unified domain representation.

In an example, unified domain CPSE methods may be defined. In an example, a method may include performing a processing step on a signal in the Unified Domain that may include performing a high resolution frequency analysis. The high resolution frequency analysis may be an extension of the 1-dimensional CSPE transformation discussed previously. As in the 1-dimensional case, the phase evolution of the components of a signal in the Unified Domain may be analyzed between an initial sample of N points and a time delayed sample of N points. From this comparison, a fractional multiple may be obtained that is representative of the spatial location where the signal components actually appear. As a result, the correct underlying frequency and estimated spatial location for the signal may be determined. To correct the underlying frequency present in the sampled signal, the information may be utilized to re-assign signal power in the frequency bins of the transform utilized to obtain the high resolution frequency analysis.

In accordance with one or more examples, one process that may be utilized to manipulate a signal in the Unified Domain may be a high resolution frequency analysis and the process may be implemented as a matrix-based version of the Complex Spectral Phase Evolution (CSPE) method. As a result, the transformation may in certain examples, for example, give signal accuracies on the order of 0.01 Hz for stable signals at CD sample rates analyzed in approximately 46 ms windows. In certain other examples, signal accuracies of 0.01 Hz, 0.001 Hz or even finer accuracies may result. The CSPE high resolution analysis may be capable of converting tone-like signal components to line spectra with well-defined frequencies, while the noise-like signal bands do not take on structure. As such, the signal may be substantially segregated into tone-like and noise-like components. Further processing may be utilized to, such as, detect if there is the presence of a transient signal component or an amplitude- or frequency-modulating signal component in a frame of sample data or test for, and aggregate, harmonic groupings of frequencies. Persons skilled in the art may appreciate that the processing may be performed on an entire signal (e.g., an entire audio signal) or portions of a signal. As such, a windowing step may be provided at any point in the process. For example, frames of data may be taken directly from the multi-channel data stream or from the data in the Unified Domain.

In an example, the UD transformation may provide a way to analyze data simultaneously in multiple channels, such as might be present in music for stereo music with two channels or surround sound music with multiple channels. In a similar example, one may consider image and video data to be composed of multiple channels of data, such as in the RGB format with Red, Blue and Green channels. Thus, the multi-channel signal may be represented in the form of a one-dimensional magnitude vector in the frequency domain, multiplied by a vector of matrices taken from the Special Unitary Group, SU (n). Accordingly, a more particular transformation of a multiple channel signal to a signal in the Unified Domain may occur as follows.

In one illustrative example, the input data may be stereo music containing 2 channels of data designated Left and Right, and the result may be a magnitude vector multiplied by a vector of matrices from the Special Unitary Group of dimension 2, SU(2). A transformation process to achieve the above mentioned conversion of stereo music to the resultant magnitude vectors may include a plurality of steps. The first step may include selecting a window of music data and transform it to the frequency domain using a transformation such as the Discrete Fourier Transform (DFT). As a result of performing the step, a representation of the signal in discrete frequency bins may be obtained. In an example, N samples may be selected in the window of data. Consequently N frequency bins may be obtained. Alternatively, there may be variations of the transforms known to those skilled in the art that may alter the number of frequency bins.

The frequency domain transformation may result in 2 channels of (generally) complex frequency information. Thus, each frequency bin may be viewed as a complex vector with 2 elements. These elements may then be multiplied by a complex matrix taken from the group SU (2), resulting in a single magnitude component. This magnitude component may be stored with the matrix as the representation of the stereo music.

In an example, the transformation process may be represented mathematically as follows:

$$\text{left channel: } \vec{S}_L = s_{0L}, s_{1L}, s_{2L}, \ldots$$

$$\text{right channel: } \vec{S}_R = s_{0R}, s_{1R}, s_{2R}, \ldots$$

To convert to the frequency domain, the following mathematical operations may be performed:

$$\vec{F}_L = DFT(\vec{s}_L)$$

$$\vec{F}_R = DFT(\vec{s}_R)$$

The group elements may be represented in a plurality of ways. For example, for the SU(2) matrices for 2 channels of data the representation may take the form as represented below:

$$U = \begin{bmatrix} e^{-i\phi_1} \cos\sigma & e^{-i\phi_2} \sin\sigma \\ -e^{i\phi_2} \sin\sigma & e^{i\phi_1} \cos\sigma \end{bmatrix}$$

In an example, the angles with components of the frequency domain vectors may be identified as follows. Let the $j^{th}$ complex component of $\vec{F}_L$ be designated as $a_j + ib_j = r_{Lj} e^{i\Phi_1}$ and the $j^{th}$ complex component of $\vec{F}_R$ be designated as $c_j + id_j = r_{Rj} e^{i\Phi_2}$. The complex frequency components may then be identified with the elements of the (KS note: this must appear as SU(2) with no gaps or separations or carriage returns inserted) SU(2) matrix for the $j^{th}$ frequency bin by setting $$\cos\sigma = r_{Lj} \Big/ \sqrt{r_{Lj}^2 + r_{Rj}^2}$$

and $$\sin\sigma = r_{Rj} / \sqrt{r_{Lj}^2 + r_{Rj}^2},$$

and the phase variables may be the same $\phi_1$ and $\phi_2$ values. If the SU(2) matrix is multiplied by a 2-vector of the frequency components for the $j^{th}$ frequency bin, then the result may be a single magnitude vector:

$$[U_j]\begin{bmatrix} F_{Lj} \\ F_{Rj} \end{bmatrix} = \begin{bmatrix} \sqrt{r_{Lj}^2 + r_{Rj}^2} \\ 0 \end{bmatrix}$$

The SU (2) matrices may be preferably unitary and may have inverse matrices, such that, all of the information may be contained in the magnitude vector and the U matrix. Thus, a new representation for the two channel data may be provided that may contain all of the information that was present in the original:

$$\sqrt{r_{Lj}^2 + r_{Rj}^2}\,[U_j] = \sqrt{r_{Lj}^2 + r_{Rj}^2}\begin{bmatrix} e^{-i\phi_1}\cos\sigma_j & e^{-i\phi_2}\sin\sigma_j \\ -e^{i\phi_2}\sin\sigma_j & e^{i\phi_1}\cos\sigma_j \end{bmatrix}$$

In one or more examples, once the data is represented in the Unified Domain representation, the previously represented two independent channels of music, that is to say, the right and the left frequencies, may be represented in the Unified Domain as a single magnitude vector multiplied by a complex matrix from SU(2). The transformation may be inverted easily, so it may be possible to change back and forth in a convenient manner.

In the one or more examples discussed above, a majority of the signal processing operations that may be used in processing multi-channel signals may be computed in the Unified Domain. So, in one application, the front end processing may use a calculation of the Complex Spectral Phase Evolution (CSPE). The Unified CSPE may be calculated by converting a window of data to the Unified Domain. The representation for that window may be called $\Lambda_1$. Further, a time-shifted window of data to the Unified Domain may be represented as $\Lambda_2$. The Unified CSPE may then require a calculation of $\Lambda_1 \odot \Lambda_2^*$, where the operator $\odot$ is configured to take the component-wise product (also known as the Schur product or Hadamard product) of the matrices over all of the frequency bins, and the * indicates that the complex conjugate is taken. In order to obtain the remapped frequencies of the CSPE in the Unified Domain, the arguments of the complex entries in the Unified CSPE may be calculated.

In an example, the traditional signal processing functions may be advantageously reformulated so that they may be computed in the Unified Domain. In an example, there may be a mathematical equivalence between the Unified Domain and the usual representations of data in the frequency domain or the time domain. When coupled with the remapping of the frequencies in the Unified CSPE, it may become possible to consider the signal components as having a spatial position and internal phase relationships. This may be done, such that, in the case where the input data is stereo audio with right and left channels, by associating the spatial effect of the stereo audio to operate over a field spanning an angle of approach to the listener. In this view, a signal component that may occur with a given value of $\sigma$ may be viewed as occurring at angle $\sigma$ in the stereo field, with a magnitude given by the magnitude component derived from the Unified Domain representation magnitude values. Furthermore, the internal phase angles of the 2 channels may be preserved in the $\phi_1$ and $\phi_2$ values assigned to that signal component.

In an example, the music on the left and right channels may be composed of two components, with frequencies $f_0$ and $f_1$. When the components may be converted to the Unified Domain and processed with the Unified CSPE, these signals may be associated with their magnitudes, spatial positions, and internal phases so $f_0 \leftrightarrow |f_0|$, $\sigma_0$, $\phi_{01}$ and $\phi_{02}$ and for the second signal, the association is $f_1 \leftrightarrow |f_1|$, $\sigma_1$, $\phi_{11}$ and $\phi_{12}$. Then, determination of the coherency surface may be adapted to have a spatial component. For example, if a signal component such as $f_0$, would have a 1-dimensional masking effect over nearby frequencies that is given by the masking function $G(f_0; f)$, then this masking effect may be extended to the unified domain, the coherency surface function would pick up a spatial component related to the angular separation between the signal components, and one can represent one embodiment of this as a coherency function $H(f_0; f, \sigma) = G(f_0; f) \cdot \cos(\sigma - \sigma_0)$, where the cosine function represents the spatial component. Similarly, a coherency function may be derived for every signal component and a global coherency surface defined over the entire spatial field of the data may be found, for example, by taking the sum of the coherency functions at a given point in the spatial field, or the maximum of the coherency functions at a given point in the spatial field or the average of the coherency functions at a point in the spatial field or any of a number of other selection rules for the coherency functions at a point in the spatial field. Further, other spatial functions than the cosine function may be utilized as well as functions that drop off faster in the spatial direction or functions that fall off slower in the spatial direction.

Figure 9:
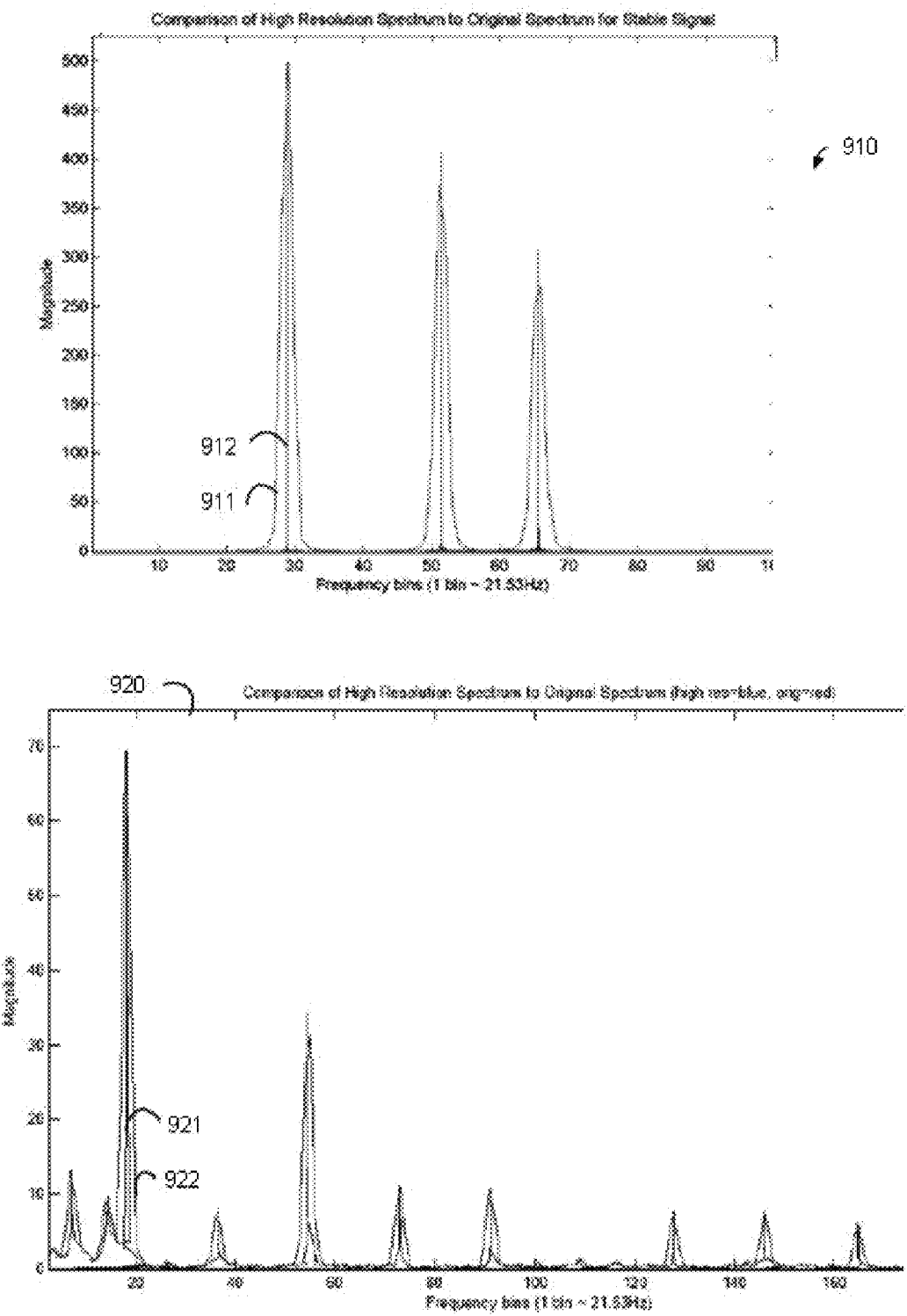
FIG. 9 illustrates a graphical representation of FFT spectrum according to an exemplary and non-limiting embodiment.

In an example, the process of converting to the Unified Domain, calculation of high-resolution Unified CSPE information, and calculation of Coherency surfaces in the Unified Domain, may provide the possibility to jointly consider all of the components that make up a multi-channel signal and process them in a consistent manner. In alternative examples, other refinements and examples of the applicability of the signal processing algorithms may be made. For example, the CSPE super-resolution algorithm may be applied more generally than just to a single signal component. Accordingly, the CSPE algorithm may be used to resolve many signals components provided there is some separation between the signal frequencies. When multiple signals may be present, the super-resolution of the frequencies may be most accurate near spectral frequency bins that may be dominated by an individual signal component, and the regions of the spectrum that are away from the signal centers may be generally remapped to the nearest dominant signal frequency. For example, for a signal composed of three sinusoids the signals do not lie in the center of frequency bins. In this example, the algorithm may be configured to successfully recalculate the true underlying frequencies with good accuracy. FIG. 9 illustrates a graphical representation of this process (see 910). The original FFT spectrum is shown as line 911 and the remapped spectrum is shown as line 912; the remapped spectrum is effectively a line spectrum. For this example, the exact frequencies (in frequency bin numbers) are 28.7965317, 51.3764239, and 65.56498312, while the estimated frequencies are 28.7960955, 51.3771794, and 65.5644420. If these spectra were calculated from music sampled at CD sampling rates of 44100 samples/sec, the fundamental transform resolution of each frequency bin would be approximately 21.53 Hz/bin, so the measured signals are accurate to approximately ±0.001 bins, which is equivalent to ±0.02153 Hz. However, the real-world music data may not be as clean and stable. Thus, the accuracy of the computed high-resolution spectrum may be affected such as by the presence of nearby interfering signals, modulations of the frequencies, and noise-like signals that have a broadband spectrum. In such examples, the high-resolution analysis may give signal accuracy of the order of 0.1 Hz for any signal component that may be relatively stable over the sample window. An example is given for a window of data taken from a track by Norah Jones and the remapped spectrum appears in signal 920, where the original signal is line 922 and the remapped signal is line 921. In an example of an alternate variation of the algorithm, a similar resolution may be provided for a linearly modulating signal component while returning a high-resolution estimate of the initial signal frequency in the window, along with the modulation rate. This may be affected by changing the CSPE to include a multiplication by a complex vector that counteracts the modulation by a measured amount (the pull-back operator). This may be discussed further in the sections on frequency modulation discussed in the supporting description.

The CSPE technique may also be utilized for real signals in addition to complex signals, as real functions may be expressed as the sum of a complex function and its complex conjugate function. For example, for a real sinusoid with period $p=q+\delta$ where p is an integer and $\delta$ is a fractional deviation of magnitude less than 1, i.e. $|\delta|\leq 1$, with amplitude "a" and arbitrary phase, the samples of a real sinusoid may be written as linear combinations of complex sinusoids, such as the following (here $j=\sqrt{-1}$):

$$\vec{s}_{0(n)} = \frac{a}{2}e^{j\frac{2\pi(q+\delta)}{N}n} + \frac{a}{2}e^{-j\frac{2\pi(q+\delta)}{N}n}$$

and the one sample shift would be:

$$\vec{s}_{1(n)} = \frac{a}{2}e^{j\frac{2\pi(q+\delta)}{N}n}e^{j\frac{2\pi(q+\delta)}{N}} + \frac{a}{2}e^{-j\frac{2\pi(q+\delta)}{N}n}e^{-j\frac{2\pi(q+\delta)}{N}}$$

if $$D = e^{j\frac{2\pi(q+\delta)}{N}}$$

is defined, the vectors may be written as:

$$\vec{s}_{0(n)} = \frac{a}{2}D^n + \frac{a}{2}D^{-n}$$

$$\vec{s}_{1(n)} = \frac{a}{2}D^n D + \frac{a}{2}D^{-n}D^{-1}$$

In this example, the DFT of each one of these vectors may then be:

$$F(\vec{s}_0) = F\left(\frac{a}{2}D^n + \frac{a}{2}D^{-n}\right)$$

$$F(\vec{s}_0) = \frac{a}{2}F(D^n) + \frac{a}{2}F(D^{-n})$$

-continued $$F(\vec{s}_1) = F\left(\frac{a}{2}D^n D + \frac{a}{2}D^{-n}D^{-1}\right)$$

$$F(\vec{s}_1) = \frac{a}{2}DF(D^n) + \frac{a}{2}D^{-1}F(D^{-n})$$

The CSPE may be computed using the complex product $F(\vec{s}_0)\odot F^*(\vec{s}_1)$ of the shifted and unshifted transforms, where the product operator $\odot$ may be defined as the complex product taken element-by-element in the vector:

$$F(\vec{s}_0)F^*(\vec{s}_1) = \left[\frac{a}{2}F(D^n) + \frac{a}{2}F(D^{-n})\right] \odot \left[\frac{a}{2}DF(D^n) + \frac{a}{2}D^{-1}F(D^{-n})\right]^*$$

$$= \left(\frac{a}{2}\right)^2 [F(D^n) + F(D^{-n})] \odot [D^*F^*(D^n) + DF^*(D^{-n})]$$

The product may be expanded to obtain the following $$F(\vec{s}_0)F^*(\vec{s}_1) = \left(\frac{a}{2}\right)^2 \begin{bmatrix} D^*F(D^n) \odot F^*(D^n) + \\ DF(D^n) \odot F^*(D^{-n}) + \\ D^*F(D^{-n}) \odot F^*(D^n) + \\ DF(D^{-n}) \odot F^*(D^{-n}) \end{bmatrix}$$

The above equation may be simplified to produce:

$$F(\vec{s}_0)F^*(\vec{s}_1) = \left(\frac{a}{2}\right)^2 \begin{bmatrix} D^*F\|(D^n)\|^2 + \\ DF(D^n) \odot F^*(D^{-n}) + \\ D^*F(D^{-n}) \odot F^*(D^n) + \\ D\|F(D^{-n})\|^2 \end{bmatrix}$$

In an example, the above simplified equation may be viewed as a sum of the CSPE for a "forward-spinning" or "positive-frequency" complex sinusoid and a "backward-spinning" or "negative-frequency" complex sinusoid, plus interaction terms. The first and the last terms in the sum may be the same as previously discussed CSPE calculations, but instead of a single complex sinusoid, there may be a linear combination of two complex sinusoids. Further, the contributions to the CSPE from these two terms may represent highly-concentrated peaks positioned at $q+\delta$ and $-(q+\delta)$, respectively. The interaction terms may have some properties that may decrease the accuracy of the algorithm if not handled properly. As will be shown below, the bias introduced by the interaction terms may be minimized by windowing the data. Additionally, the interaction terms, $\Gamma$, may be simplified as follows:

$$\Gamma=[DF(D^n)\odot F^*(D^{-n})+D^*F(D^{-n})\odot F^*(D^n)]$$

$$\Gamma=2*Re[DF(D^n)\odot F^*(D^{-n})]$$

$F(D^n)$ may be, for example, a peak concentrated at frequency position $q+\delta$, and that $F(D^{-n})$ may be a peak concentrated at frequency position $-(q+\delta)$, and that the product may be taken on an element-by-element basis, (so $\Gamma\approx 0$ for a number of cases).

The data provided in the exemplary scenario discussed above may be analyzed using an analysis window, including but not limited to a Hanning window, a Hamming window, or a rectangular window, or any other standard windowing function. Further, the measured spectrum may be found by convolving the true (that is to say, delta-like) sinusoidal spectrum with the analysis window. For example, if a rectangular window (such as, the boxcar window) is used, the leakage into nearby spectral bins may be significant and may be of sufficient strength to produce significant interaction terms. The interaction terms may cause the magnitude squared terms (that is to say, the terms in $\|\bullet\|^2$ brackets) to interfere. To reduce the chance of significant interaction terms, another analysis window known in the art may be utilized so that the leakage may be confined to the neighborhood of q+δ, and −(q+δ), so the Γ≈0 case is the most common situation. Further, after the CSPE is calculated, the frequencies may be reassigned by extracting the angle information. For the positive frequencies (such that where k>0), it may be determined that:

$$f_{CSPEk} = \frac{-N\angle(F_k(\tilde{s}_0)F_k^*(\tilde{s}_1))}{2\pi}$$

$$= \frac{-N\angle\left(\left(\frac{a}{2}\right)^2 \|F_k(D^n)\|^2 e^{j\frac{2\pi(q+\delta)}{N}}\right)}{2\pi}$$

$$= \frac{-N\left(\frac{2\pi(q+\delta)}{N}\right)}{2\pi}$$

$$f_{CSPEk} = (q+\delta)$$

For the negative frequencies (k<0), the opposite value, $f_{CSPEk} = -(q+\delta)$ may be determined. Consequently, in the case of real signals (such as may be the case when Γ≈0), all of the power in the positive frequencies may be remapped to q+δ, and all of the power in the negative frequencies may be remapped to −(q+δ). Such a result may be substantially independent of the frequency bin and may allow for extremely accurate estimates of frequencies.

In an example, CSPE may be performed for real sinusoids that have been windowed with an analysis window. CPSE may then be generalized, for example, to include the effects of windowing by defining the basic transform to be a windowed transform. For exemplary purpose, data may be windowed before computing the DFT. Further, for the purpose of exemplary discussion, an arbitrary analysis window, A (t), and its sampled version $A_n$ may be defined. The transforms may be performed as has been discussed previously. Further, the analysis window may be pre-multiplied by the function illustrated as below: ⇒ where the W subscript indicates that a windowed transform may be utilized.

Thus, in the presence of windowing, the following may be obtained:

$$F_W(\tilde{s}_0)F_W^*(\tilde{s}_1) = \left(\frac{a}{2}\right)^2 \begin{bmatrix} D^*\|F_W(D^n)\|^2 + \\ 2\text{Re}\{DF_W(D^n) \odot F_W^*(D^{-n})\} + \\ D\|F_W(D^{-n})\|^2 \end{bmatrix}$$

The transform may enable minimizing the leakage into nearby frequency bins and further, reducing the interference terms to be negligible in most cases.

In accordance with some exemplary and non-limiting embodiments, in a unified domain model/super-resolution model for signal processing, an interaction among non-orthogonal AM/FM elements may be determined in a frequency-changing signal. Such determination may be made "tracker aware" so that an interaction tracker may be configured to look at the history of tracklets as they are evolving to make a consistent determination between the AM and FM components.

In an example, a method for performing modulation detection through an advanced fit process may be defined. For the purpose of discussion of the method, an assumption regarding the conventional Fourier based analysis methodology may be made. The assumption may describe that the conventional Fourier based analysis operates in a manner that any oscillator peak may be produced by a stable sinusoid during the time of a single analysis window, with a constant frequency and amplitude. For many applications, however, it may be necessary to detect changes in frequency and/or amplitude within a single analysis window. Such detection may be made by considering in combination or in isolation, one or more of the techniques as may be discussed below.

In an example, an amplitude modulation (AM)/frequency modulation (FM) detection technique using high resolution window (HRW) creation may be defined. The technique may include a singlet transformation process including applying a high resolution, frequency domain version of the analysis window to the time-domain samples to characterize the oscillator peak that may be analyzed. For the purpose of description, the high-resolution frequency domain version of the analysis window may be referred to as an (HRW).

In an example, the singlet transformation process may be used to characterize the oscillator peaks that may not be constant in amplitude and/or frequency within the sample window. In order to do so, an HRW with the corresponding amplitude and/or frequency modulation may be used for analysis. Such an HRW designed for amplitude modulation may hereinafter be referred to as an (AM HRW) for the purpose of description. For example, to analyze an oscillator peak that may be the result of a sinusoid that increased in amplitude during the sample window, it may be compared to an HRW where the analysis window used to create the HRW may be multiplied by the same increasing amplitude prior to conversion to the frequency domain. In a similar example, to analyze an oscillator peak that is modulating in frequency, an HRW where the analysis window is multiplied by a Modulation Creation Operator for the corresponding frequency modulation rate prior to conversion to the frequency domain may be used. Such an HRW may be hereinafter referred to as an (FM HRW) for the purpose of description.

The detection techniques discussed above may be combined to analyze the effects of a sinusoid with both amplitude and frequency modulation. Such an HRW may be hereinafter referred to as an (AM/FM HRW) for the purpose of description.

Figure 10:
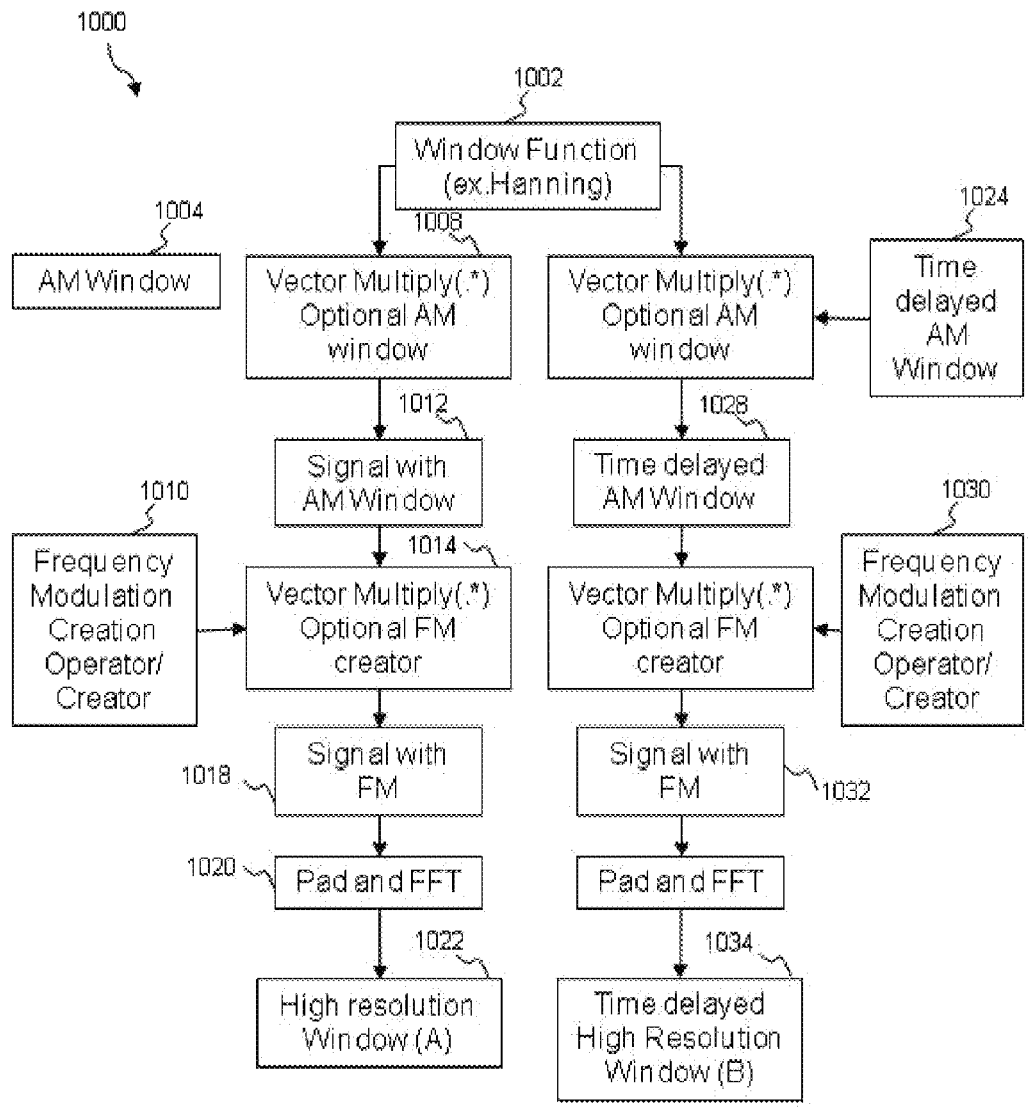
FIG. 10 illustrates an example of a method for creating high-resolution windows for AM/FM detection according to an exemplary and non-limiting embodiment.

FIG. 10 illustrates an example of a method for creating the high-resolution AM/FM windows. The method 1000 includes starting the process of high-resolution window creation with a copy of an original analysis window, such as is illustrated by the Window function 1002. The method 1000 may further include, at 1008, multiplying the analysis window 1002 by the desired amplitude modulation 1004, using such as a Hadamard product, for creating a window for the analysis of amplitude modulation 1012. The method 1000 may further include, at 1014, multiplying the window 1012 by the frequency Modulation Creation Operator 1010 with the appropriate modulation amount to create the window for the analysis of frequency modulation 1018. The Frequency Modulation Creation Operator (FMCO) may be configured to transform a sinusoid that is stable in frequency to one that is modulating in frequency. The method 1000 may further include, at 1020, padding the window 1018 to the desired length. In a preferred example, the desired length may be 16 or 32 times the original length of the sample window. Further, at 1020, an FFT or DFT may also be performed to the transform the analysis to the frequency domain. The transformation may result in a high resolution window (A) 1022, as illustrated in the example of FIG. 10.

The method 1000, may also be performed alternatively by repeating the steps 1008 till 1020 by using time shifted AM window 1024 and/or time shifted FM window 1030, that may be obtained by shifting the AM window 1004 and the FM window 1010 by the appropriate shifting factors for the time delay used when preparing the Sample time delayed high resolution Window (B) 1034 in the pre-processor.

Figure 11:
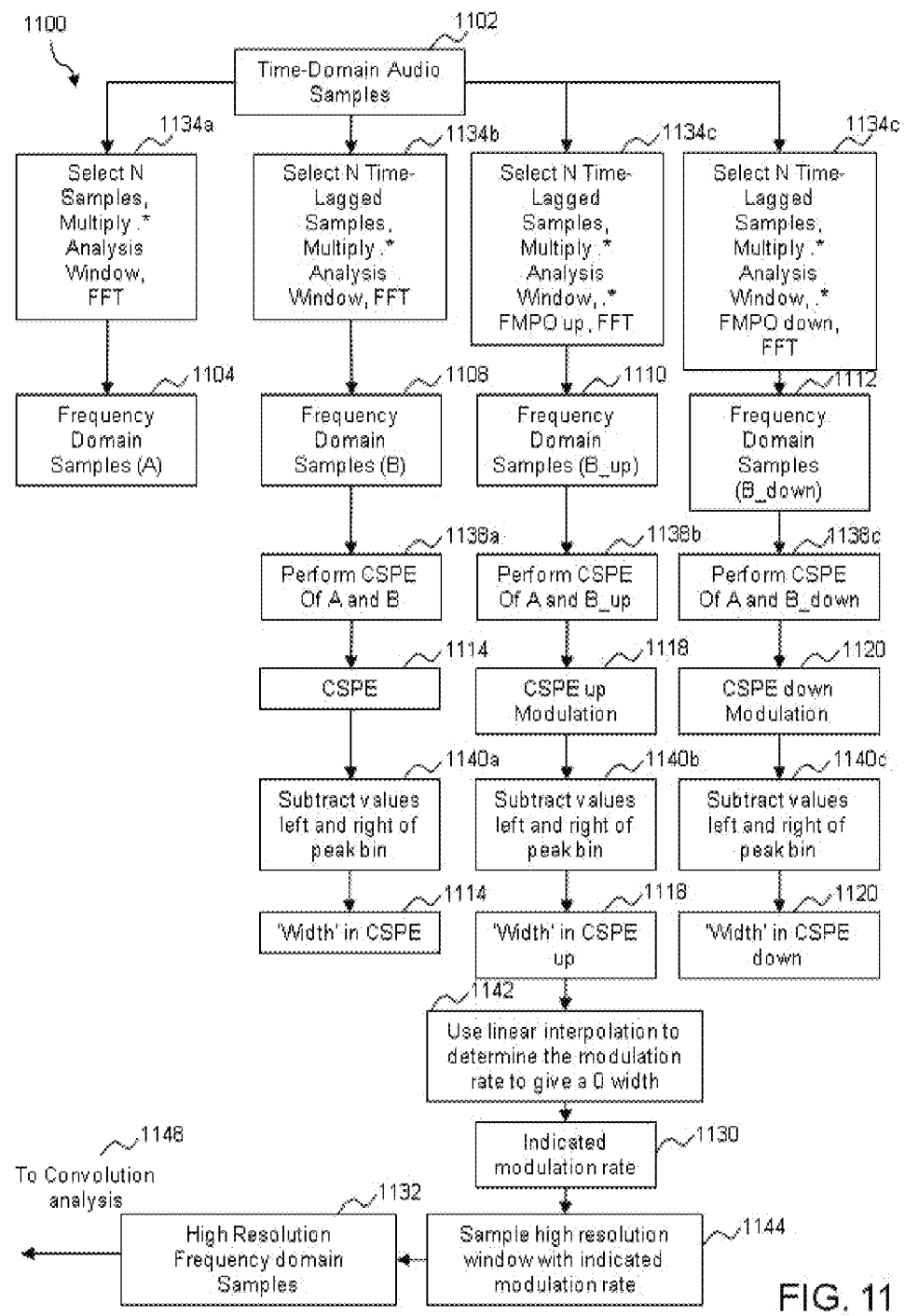
FIG. 11 illustrates an example of a method for frequency modulation detection according to an exemplary and non-limiting embodiment.

In an example of a method for amplitude modulation (AM) detection, amplitude modulation may be detected by using the Singlet Transformation Method to compare various AM HRWs, each of which may have a different AM envelope applied in the time domain, as discussed previously. An AM HRW may be closest in shape in the frequency domain to an oscillator peak created from a sinusoid that has a similar amplitude modulation. Thus, the amplitude modulation of the original signal may be detected by selecting the AM HRW with the lowest residual error FIG. 11 illustrates an example of a method 1100 for frequency modulation detection. The method 1100 includes, at 1134, using the original time-domain audio samples 1102 in the pre-processor to create two additional (B) windows, the frequency domain sample window (B_UP) 1110, and the frequency domain sample window (B_DOWN) 1112. The additional windows may be created by, applying the Frequency Modulation Pullback Operator (FMPO) for a positive modulation to one (B) window, at 1134*c*, and call the window the (B_up) window 1110. This may be accomplished via a Hadamard product. Similarly, the method 1030 allows for the creation of Frequency Modulation Creation Operators. Similarly, the method 1100 may include, at 1134*d*, applying the Frequency Modulation Pullback Operator (FMPO) for a negative modulation to the other (B) window, and call it the (B_down) window 1112. This may also by accomplished via the Hadamard product. The method 1100 may further include, at 1138 (*a-c*), performing three Complex Spectral Phase Evolutions (CSPEs), as discussed in the description for Single Channel Super-Resolution Module, a non-modulation CSPE, at 1138*a*, of the (A) window and the (B) window; an up modulating CSPE, at 1138*b*, of the (A) window and the (B_up) window; and a down modulating CSPE, at 1138*c*, of the (A) window and the (B_down) window. In accordance with certain non-limiting examples, taking the inputs and implementing the methods described herein, a processor may be configured to receive a first set and a second set of frequency domain data, each having a given, or "fundamental," transform resolution, and the processor may further be configured to perform complex spectral phase evolution (CSPE), as further described herein, on the frequency domain data to estimate component frequencies at a resolution at very high accuracy, such that the accuracy may be typically greater than the fundamental transform resolution. As used herein, "transform resolution" may refer to the inherent resolution limit of a transformation method; for example, if a DFT or FFT is calculated on an N-point sample window taken from data that was sampled at Q samples per second, then the DFT or FFT may exhibit N frequency bins, of which half would correspond to positive (or positive-spinning) frequency bins and half would correspond to negative (or negative-spinning) frequency bins (as may be defined by a standard convention known in the art). The highest properly sampled signal that may be detected in this method may include a frequency of Q/2 that may be divided up into N/2 positive frequency bins, resulting in an inherent "transform resolution" of Q/N Hertz per bin. A similar calculation may be done for any of the other transformation techniques to determine the corresponding "transform resolution." In some examples there may further be performed peak selection comprising identifying one or more oscillator peaks in the frequency domain data, testing the CSPE behavior of at least one point near at least one of the identified oscillator peaks to determine well-behaved and/or short-term-stable oscillation peaks and performing an extraction of identified oscillator peaks. In other examples, further the amplitude and the phase of each identified oscillator peaks may be determined and a singlet transformation/singlet representation may be performed to map from a high resolution space to a low resolution space. In other examples, a singlet representation may be performed to remove a contribution of each identified oscillator peak from the frequency domain data.

As used above and herein, the "given," "original" or "fundamental" transform resolution is the resolution of the transform, such as the FFT, that may be used to provide the input data set of frequency domain data—that is, the inherent resolution of the transform used as the fundamental building block of the CSPE. Additional details on the CSPE transformation may be described in the following description.

In an example, performing the CPSE at 1138*a*-1138*c* may result in the generation of three CSPE windows, a CSPE window 1114, a CSPE_Up Modulation window 1118, and a CSPE_down modulation window 1120. Once an oscillator peak may be selected, the 'flatness' of the area around the peak in the CSPE, CSPE_up and CSPE_down may be analyzed. A signal with positive frequency modulation may have a flatter area around the peak in the CSPE_up, a signal with negative frequency modulation may have a flatter area around the peak in the CSPE_down, and a signal with a relatively low amount of frequency modulation may have a flatter area around the peak in the CSPE. For the purpose of description, the 'flatness' may refer to a plot of estimated frequency (or its equivalent measure, the effective rotation in complex space of the transforms for the A and B windows) such that the frequency bins near the oscillator peak map to a nearly constant value. The method 1100 may further include, at 1140 (*a-c*), subtracting the values in the left and right of peak from the CSPE window 1114, the CSPE_up window 1118 and the CSPE_down window 1120, to identify the width in CSPE 1122, the width in CSPE_up 1124 and the width in CSPE_down 1128 respectively, of the frequency modulation. If frequency modulation is detected, the values calculated at 1140, that is to say the values 1120-1124, may be used at 1142 to interpolate the exact amount of frequency modulation. As a result, at 1130, the indicated modulation rate may be obtained. At 1144, the indicated modulation rate 1130 may further be used in conjunction with an FM HRW to analyze and remove the oscillator peak to obtain the high resolution frequency domain samples 1132, which may further be used for convolution analysis 1148.

In an example, a method for FM detection may be elaborated. The complex spectral phase evolution methods may be extended so that they may be applied to signals that are more complicated than the short-time stable sinusoids that were introduced earlier. In this example, a variation on the CSPE may be introduced that may be applied to signals that may be sweeping through a range of frequencies, and may determine with good accuracy the key underlying parameters that may define the sweeping frequency.

An exemplary way to define a linear swept sine signal in the continuous case may be as follows:

$$x(t) = \sin\left(2\pi\left(f_0 t + \frac{\delta}{2}t^2 + \phi_0\right)\right)$$

where $f_0$ may be the root frequency, $\delta/2$ may be the frequency modulation rate and $\phi_0$ may be the initial phase of the signal. In the case where the signal may be discretely sampled, a convenient form of the swept sine signal may be:

$$\vec{x} = \exp\left(i\frac{2\pi}{N}\left\{[0:N-1]f_0 + \frac{\delta}{2}[0:N-1] + \frac{\delta}{2}([0:N-1] \odot [0:N-1])\right\}\right)$$

where [0: N−1] may be defined as to mean a vector of samples labeled 0, 1, 2, ..., N−1, and ([0:N−1]⊙[0:N−1]) may be the Hadamard/Schur product of the sample vector with itself. For the purpose of discussion, the Hadamard, Schur product of a vector with itself may hereinafter be abbreviated as $[0:N-1]^{\wedge 2}$ in the following description. The operator O may be defined to be the Hadamard/Schur product hereinafter. Without deviating from the spirit and scope of this disclosure, the first two terms in the curly braces may be combined as $$\left(f_0 + \frac{\delta}{2}\right)[0:N-1],$$

but it may also be convenient to write it in the uncombined form. The notation above may indicate a complex exponential form of the sinusoid (sometimes called the "analytic signal" by those skilled in the art), but one can easily convert back to the sine or cosine form by taking the real or imaginary part of the complex exponential. In an example, the vector I may represents a (complexified) sample of N points from the swept sine signal, and a subscript may be added to indicate the last sample included in the vector, such that in an example, the notation $\vec{x} \rightarrow \vec{x}_{N-1}$ may be used to represent that this vector of samples ends at sample N−1 (but it is implied that N total samples are included in the vector). Consequently, using this notation, the next possible group of N samples may be represented as depicted below:

$$\vec{x}_N = \exp\left(i\frac{2\pi}{N}\left\{[1:N]f_0 + \frac{\delta}{2}[1:N] + \frac{\delta}{2}([1:N]^{\wedge 2})\right\}\right)$$

In keeping with the spirit and scope of the CSPE methods discussed in the underlying description, the evolution of the signal from one group of N samples to a later group of N samples may be analyzed. In an example, this may be achieved by defining an evolution operator that may advance the signal so as to define $\Gamma_1: \vec{x}_{N-1} \rightarrow \vec{x}_N$ to be a one-sample evolution operator (applying it multiple times may advance the signal by more than one sample):

$$\Gamma_1 = \exp\left(i\frac{2\pi}{N}\{\vec{f}_0 + \delta[1:N]\}\right)$$

whereby $\vec{f}_0$ may represent vector of length N where each entry may be the value $f_0$. Then by combining and refactoring it may be observed that $\vec{\Gamma}_1 \odot \vec{x}_{N-1} = \vec{x}_N$. This may be seen by the following rearrangement of the vector terms in the exponent:

$$\vec{f}_0 + \delta[1:N] + [0:N-1]f_0 + \frac{\delta}{2}[0:N-1] +$$
$$\frac{\delta}{2}([0:N-1]^{\wedge 2}) = [1:N]f_0 + \frac{\delta}{2}[1:N] + \frac{\delta}{2}[1:N] +$$
$$\frac{\delta}{2}[0:N-1] + \frac{\delta}{2}([0:N-1]^{\wedge 2}) = [1:N]f_0 + \frac{\delta}{2}[1:N] +$$
$$\frac{\delta}{2}\{[1:N] + [0:N-1] + [0:N-1]^{\wedge 2}\} = [1:N]f_0 +$$
$$\frac{\delta}{2}[1:N] + \frac{\delta}{2}[1:N]^{\wedge 2}$$

where the last step may follow from the general term: $n+(n-1)+(n-1)^2 = 2n-1+(n^2-2n+1) = n^2$.

Thus it may be observed that $$\Gamma_1 \odot \vec{x}_{N-1} = \exp\left(i\frac{2\pi}{N}\left\{[1:N]f_0 + \frac{\delta}{2}[1:N] + \frac{\delta}{2}[1:N]^{\wedge 2}\right\}\right) = \vec{x}_N$$

In an example, the ability to specify the evolution operator may be important since the basic premise of the CSPE methods may be to compare a time-advanced (or, in some applications, space-advanced) snapshot of a signal with the original snapshot of the signal and then to isolate terms that may reveal the underlying parameters that may be used in a mathematical reconstruction of the signal. As has been previously discussed, the "frequency" $f_0$ may be held at the first instant in the group of samples, and it may be more convenient to reformulate the problem so that the modulation may be considered relative to the instantaneous "frequency" at the center of the window of N samples. The quotes have been placed around "frequency" since it may be more accurate to consider $f_0$ to be the period of the signal, since a sinusoidal signal of the form $$x = \sin\left(\frac{2\pi}{N}[0:N-1]f_0\right)$$

may go through exactly $f_0$ periods in the N samples; however, it may be common to call $f_0$ the frequency and one skilled in the art may be able to determine the precise meaning based on the context of the usage. In this example, the modulation may be sweeping away from the initial frequency $f_0$ and one may view this as setting the initial instantaneous frequency in a group of N samples as being $f_0$. It may be possible to reformulate the modulation problem so that the modulation may be viewed as a modulation about an instantaneous frequency that may occur at the center of a group of N samples. This centered formulation may be convenient and so it may be discussed further.

In an example, the creation of a modulating signal may begin with a stable sinusoid, and Q periods over N samples may be taken such that:

$$\vec{x} = \exp(i2\pi[0:N]Q/N)$$

Further, a (centered) Frequency Modulation Creation Operator (FMCO) may be defined as:

$$FMCO = \exp\left(i\frac{2\pi}{N}\frac{\delta}{2}\left[-\frac{N}{2}:\frac{N}{2}\right]^{\wedge 2}\right)$$

and when the FMCO may be applied to the sampled sinusoid $\vec{x}$, the result may be a modulating signal, $\vec{y}$ (here defined with N+1 points that will be used to study the signal evolution):

$$\vec{y} = \exp\left(i\frac{2\pi}{N}\frac{\delta}{2}\left[-\frac{N}{2}:\frac{N}{2}\right]^2\right) \odot \exp(i2\pi[0:N]Q/N) =$$

$$\exp\left(i\frac{2\pi}{N}\left\{[0:N]Q + \frac{\delta}{2}\left[-\frac{N}{2}:\frac{N}{2}\right]^{\wedge 2}\right\}\right)$$

where y may be a linearly modulating signal, with an instantaneous center frequency corresponding to Q periods in an N point sample window.

In the exemplary embodiment discussed above, the linear frequency modulation may be created in such a way that if δ=1/N, then the signal may exhibit an increase of 1 period in every sequential non-overlapping N-point sample window. Thus, while it may be recognized that the frequency may be increasing in a continuous and linear fashion, the defined equation structure may lead to a signal with Q full oscillations in the first N samples (such that a full oscillation may be defined to be a passage through a full 2π interval), and in the next N samples, the signal may exhibit Q+1 full oscillations, and in the next N samples the signal may exhibit Q+2 full oscillations, and the like.

In an example, if the modulation parameter δ=2/N, then the formulation above may give an increase of 2 periods in every subsequent window of N samples (non-overlapping). In an alternate example, if the windows are overlapped by 50%, it may give an increase of 1 period in each subsequent 50% overlapping window, so if the signal exhibits Q full oscillations over samples 1 to N, then for a 50% overlapping window of samples N/2+1 to N/2+N, the signal may exhibit Q+1 full oscillations and for the next 50% overlapping window of samples N+1 to 2N the signal may exhibit Q+2 full oscillations.

In a similar example, if the modulation parameter may be taken to be δ=P/N, then the signal may exhibit an increase of P periods in every subsequent window of N samples (non-overlapping). In this example, the formulation of the signal frequency may be related to the value of Q (periods) through the usual transformations between frequency and period. The signal may be defined so that the instantaneous frequency at the center of an analysis window may be equal to the frequency that may create Q periods in the window. The modulations may be around that center frequency. In order to develop a method similar to the CSPE for short-time stable sinusoids and extend the method to modulating frequencies, it may be necessary to develop a Frequency Modulation Pullback Operator (FMPO) that may operate on the time-advanced (or in some cases spatially-shifted) data in such a manner that the frequency transform of the resulting signal from the Hadamard/Schur product of the FMPO and the time-advanced signal may be nothing more than a phase rotation from the transform of the first signal.

In an example, the FMPO may be defined as illustrated below:

$$FMPO = \exp\left(\pm i\frac{2\pi}{N}\delta[-N/2:N/2]\right)$$

In this example, the sign of the imaginary unit, i, may be chosen to be positive or negative depending on whether an up pullback operation or a down pullback operation may be desired. The CSPE technique for modulating signals may then become $$CSPE = F * (\vec{y}_{N-1}) \odot F(FMPO \odot \vec{y}_N) =$$

$$e^{i2\pi \cdot \frac{Q+\delta/2}{N}} F * (\vec{y}_{N-1}) \odot F(FMPO \odot \vec{y}_N) = e^{i2\pi \cdot \frac{Q+\delta/2}{N}} \|F(\vec{y}_{N-1})\|^2$$

The derivation of this result may come from the following formulation where the exponent in $(FMPO \odot \vec{y}_N)$ may be considered and the factor $$i\frac{2\pi}{N}$$

may be ignored for the purpose of the derivation:

$$-\delta\left[-\frac{N}{2}:\frac{N}{2}-1\right] + [1:N]Q +$$

$$\frac{\delta}{2}\left[-\frac{N}{2}+1:\frac{N}{2}\right]^{\wedge 2} = [1:N]Q + \frac{\vec{\delta}}{2} + \frac{\delta}{2}\left[-\frac{N}{2}:\frac{N}{2}-1\right]^{\wedge 2} =$$

$$\left(\vec{Q} + \frac{\vec{\delta}}{2}\right) + [0:N-1]Q + \frac{\delta}{2}\left[-\frac{N}{2}:\frac{N}{2}-1\right]^{\wedge 2}$$

where the transformation from the first to the second line above may be seen by considering the general term:

$$-\delta\left(\frac{N}{2}-1\right) + \frac{\delta}{2}\left(\frac{N}{2}\right)^2 = \frac{\delta}{2} + \frac{\delta}{2}\left(\left(\frac{N}{2}\right)^2 - N + 1\right) = \frac{\delta}{2} + \frac{\delta}{2}\left(\frac{N}{2}-1\right)^2$$

In the example above, putting all the elements together may give the result that $$(FMPO \odot \vec{y}_N) = \exp\left(i\frac{2\pi}{N}\left(Q+\frac{\delta}{2}\right)\right)\vec{y}_{N-1}$$

and the result above for the modulating CSPE follows. Consequently, if the angle of the modulating CSPE may be calculated, and further may be normalized by multiplying by N/(2π), the result may be exactly $$Q + \frac{\delta}{2}$$

and this result may be found in any frequency bin if a single modulating signal were present. In practice, other interfering signals may be present, but the result may still hold in the region around the spectral peak associated with the modulating signal. As a result it may be concluded that this calculation may have been rendered a local operation in the frequency domain, and this may make it much more robust. If one skilled in the art were to isolate Q and δ then the modulating signal may be recreated exactly using the modulating signal creation techniques as described within the scope described above.

In an exemplary method of determining the correct value of δ, calculation of the modulating CSPE for a set of modulation rates and from the resulting calculations, extrapolation or interpolation to the correct value of δ may be performed. The extrapolation may be done by measuring the width of the remapped spectral peak after calculating the CSPE and modulated CSPE for a few values of the modulation rate. The correct value of the modulation rate may then be used to produce a spectral peak of near-zero width, and since the width of the spectral peak may vary approximately linearly with the modulation rate, one may use interpolation or extrapolation to estimate the value of the modulation rate that may produce the near-zero width peak. This may have the benefit of allowing the calculation of independent modulation parameters (i.e. δ values) for several different signal components that may be present and may have different modulation rates. A second approach may be to use an iterative scheme to converge upon the optimal modulation rate. In either case, the desired result may be detected by the presence of a delta function-like spectrum that results from taking the power in every frequency bin and re-plotting it at the locally measured value of $$Q + \frac{\delta}{2}.$$

This may help to reduce the spectrum to a delta function when the correct value of δ is used. If a number of different modulating signals may be present, then if a signal associated with a spectral peak $p_k$ may have a modulation rate $\delta_k$, and then if the modulating CSPE may be calculated with δ replaced by $\delta_k$, then the resulting spectrum locally around peak $p_k$ may be like a delta-function. Hence, either through extrapolation/interpolation, or through iteration, it may be possible to isolate the central frequency values (corresponding to Q) or the modulation rates for linearly modulating signals.

In an example, a method for combined AM/FM detection may be defined. The methods for amplitude and frequency modulation detection discussed thus far may be used to detect either frequency modulation or amplitude modulation, but not both. There may be several methods of integrating these techniques into a coherent framework, including various decision trees, with and without mixed AM/FM detection, and tracker-assisted modulation detection. An exemplary decision tree may be discussed in the following description.

In an exemplary signal processing method, frequency modulation and amplitude modulation may be indistinguishable or intermixed. The method may include mapping the modulation into the complex plane, so that radial changes may be considered as amplitude modulation, angular changes may be considered as frequency modulation, and a co-variance matrix may be output into a tracking method. The tracker may then use the information calculated over time to determine which portion of the modulation is better or more effectively characterized as amplitude modulation and which portion is better or more effectively characterized as frequency modulation.

Figure 12:
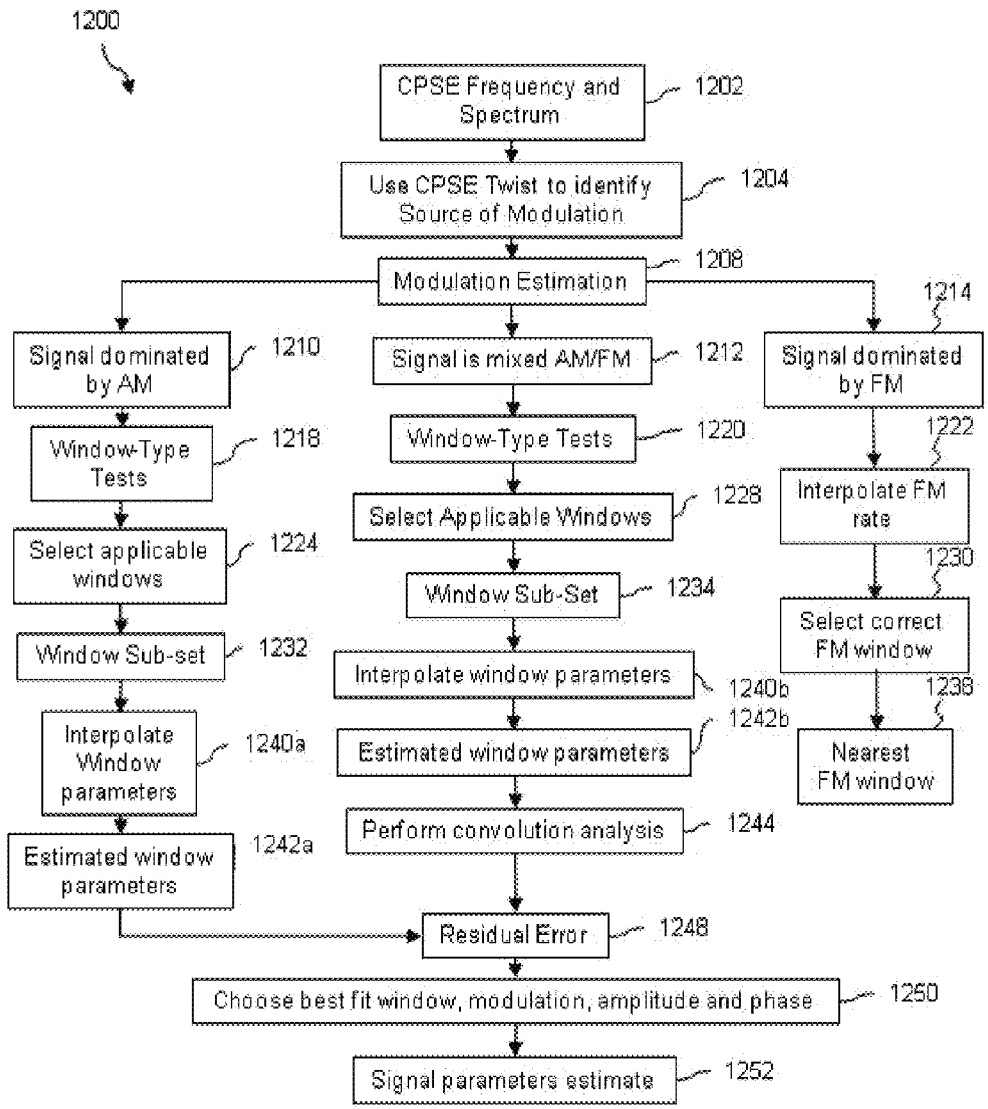
FIG. 12 illustrates a modulation detection decision tree according to an exemplary and non-limiting embodiment.

FIG. 12 illustrates an example of a method using a decision tree 1200 that may be used to combine AM/FM detection. The decision tree method 1200 may include at 1204, using a CPSE twist to identify a source of modulation for a CPSE frequency spectrum 1202. The method 1200 may further include using the modulation estimation 1208 obtained from the identification step 1204 to perform one of the three exemplary processes illustrated in the FIG. 12. In a first example, the modulation estimation 1208 may provide a signal dominated by AM 1210. In a second example, the modulation estimation 1208 may provide a signal with mixed AM/FM 1212, while in a third example, the modulation estimation 1208 may provide a signal dominated by FM 1214. The decision tree method 1200 may then include at 1218 and 1220, performing window type tests on the signal dominated by AM 1210 and the signal with mixed AM/FM 1212 respectively. The method 1200 may also include in an example, at 1222, interpolating an FM rate for the signal dominated by FM 1214. The method 1200 may then include at 1224 and/or 1228 selecting applicable windows from the windows obtained after performing window type tests 1218-1220. In an example, the method may include at 1230 selecting a correct FM window after the interpolation performed at 1222.

The method 1200 may further include, at 1232-1234 obtaining a window sub-set and/or at 1238 obtaining a nearest FM window based on the steps performed at 1224-1230. The method may further include, at 1240, that is to say at 1240a and at 1240b, interpolating window parameters for the window subsets 1232-1234, to obtain at 1242, the estimated window parameters, such as the estimated window parameter 1242a and the estimated window parameter 1242b. The method 1200 may further include, at 1244 performing convolution analysis on the estimated window parameters 1242. Further, the method 1200 may include, at 1248, identifying residual error 1248 for the results of convolution analysis 1244 and/or for the nearest FM window 1238. Based on the error, the method 1200 may include, at 1250, choosing the best fit window, modulation, amplitude and phase and provide the results of selection as the estimated signal parameters 1252. In its simplest form, the method 1200 may be reiterated as including the steps of calculating the fit-error for a non-modulating sinusoid, calculating the fit-error for various AM HRW, calculating the fit-error for the closest available FM HRW, and choosing the HRW and fit parameters that may yield the lowest residual error.

While the above steps may detect modulation effects more effectively than conventional FFT-based analysis, a more sophisticated decision tree may be used that may allow for the detection of both AM and FM simultaneously. In an example, the sophisticated decision tree may include calculating the apparent frequency modulation using any of the one or more FM detection methods discussed previously. The frequency modulation may hereinafter by refer herein to as the 'Indicated Modulation Rate'. The sophisticated decision tree may further include determining if the Indicated Modulation Rate is out of bounds or close to zero. If the Indicated Modulation Rate is out of bounds or close to zero, the modulation may be dominated by amplitude effects. Thus, amplitude modulation windows may be used for an analysis of the modulation rate using any of the plurality of AM detection methods discussed previously.

In an example of the sophisticated decision tree, if the indicated modulation rate is within certain ranges, the signal may be affected by both amplitude and frequency modulation. Thus, the sophisticate decision tree may include selecting a set of AM/FM HRWs. In an example, the amplitude modulation may skew the results of the CSPE flatness calculation. For example, a sinusoid with a positive frequency modulation of 2 periods per window may create an Indicated Modulation Rate of 2.0, but if the same sinusoid is also increasing in amplitude, it may create an Indicated Modulation Rate of 2.18. These effects may be pre-determined, and a calibration table may need to be created.

In accordance with one or more examples, there may be circumstances where amplitude modulation and frequency modulation may be indistinguishable or intermixed. In these cases, knowledge of the behavior of that oscillator in previous sample windows may be used to identify the true modulation. For example, if the oscillator peak belongs with a tracklet of data that may have been falling in frequency, it may be likely that the frequency may continue falling. In some examples, the peak detection process may be aware of the state of the tracker so that it may make such inferences. In other examples, the peak detection process may output ambiguous information that may be finalized by the tracker. Further, in some examples, the peak detector may use the track information to utilize fewer steps in an AM/FM detection decision tree, starting with the most likely AM/FM combinations.

In accordance with one or more examples, the multi-channel super-resolution method discussed previously may have as an output, a set of parameters describing individual oscillator components, and their relationship to each channel. In the set of parameters, each parameter may contain information that may be required to accurately reconstruct the oscillator with the use of such as the Unified Domain Re-synthesis methods. In a preferred example, that information may generally contain frequency, amplitude, Unified Domain sigma, amplitude modulation, frequency modulation, and the phase of the oscillator in each channel as well as any appropriate amplitude or frequency modulation parameters that may apply. The Unified Domain Sigma represents the portion of the signal that may be derived from each channel.

In accordance with exemplary and non-limiting embodiments, AM and FM modulation may be detected in a short duration window to achieve super-resolution for AM and FM characteristics. In other embodiments, one or more frequency modulation pullback operators as described herein may be applied to at least one set of sample data.

In accordance with exemplary and non-limiting embodiments, frequency modulation in a sample window may be detected. A plurality of frequency modulation pullback operators (FMPOs) may then be applied to at least a set of sample data with the results subjected to one or more of an interpolation, a linear interpolation, an extrapolation and an iteration to provide an improved estimate of an actual modulation rate. In some examples, the plurality of FMPOs may include at least two of an "up," a "down" and a "neutral" operation.

In a modification of the CSPE described above, in accordance with certain exemplary embodiments, a sample window, such as a "hamming window" or other standard windowing function or "tapers" may be used but, when dealing with an FM input signal, there may be inserted another vector (the FMPO—frequency modulation pullback operator) that may informally be hereinafter be referred to as a "twist vector". Typically, the FM signal may be moving in frequency as one receives the time-lagged version. In addition, AM signals tend to evolve in time like a rigid rotator; however, unlike the case of the effect of the analysis window used in the standard CSPE, for the AM modulation case the AM window may be a part of the data. Thus, when detecting the rotation of the "rigid rotator" of the AM window, one must allow for the shift in the AM window in the time-lagged version. For the frequency modulation case, application of the FMPO may turn the FM frequency back to something that may evolve like a rigid rotator, from which can be detected the frequency and the angular rotation. One can then derive the FM modulation and the reference "root" or "anchor" point for the frequency modulation representation.

In accordance with other exemplary and non-limiting embodiments, AM and FM modulation may be detected in a short time window to achieve super-resolution for AM and FM time windows. Complex spectral phase evolution (CSPE) may then be performed on the frequency domain data to estimate component frequencies at a resolution and/or an accuracy that may be greater than the fundamental transform resolution.

In an example, the amplitude effect of the AM signal may be different on the first snapshot or window of samples versus the lagged window of samples. Accounting for how the amplitude effect changes may allow derivation of the underlying signal from the CSPE. Conversely, as described above, with FM signals the FMPO may be used to derive the underlying FM behavior. With AM signals, the evolution of the amplitude effect may be considered.

In an example, creating the amplitude modulation windows may include taking a stable signal, applying an amplitude effect, and putting the result into a high-resolution FFT. By subsequently considering a variety of amplitude modulation effects, including but not limited to, AM effects where the amplitude envelope slopes upward, AM effects where the amplitude envelope slopes downward, AM effects where the amplitude envelope starts or stops at an arbitrary point in the data sample, AM effects where the amplitude envelope may have a combination of effects that may include sloping upward or downward or leveling off or transitioning smoothly from one AM envelope state to another, and any combination of these states, one may derive a series of high resolution oscillator peaks from which may be determined which one of the applied effects may fit best to a given component of the frequency spectrum.

In some examples, a plurality of amplitude effects may be pre-computed and multiplied by the analysis window. These amplitude effects may then be converted to the frequency domain via a high-resolution FFT or other transform and may be compared to the spectral peaks detected in the signal to determine the amplitude modulation effect that may be associated with the observed structure of the spectral peak. Examples of these AM effects may include, but are not limited to AM effects where the amplitude envelope slopes upward, AM effects where the amplitude envelope slopes downward, AM effects where the amplitude envelope starts or stops at an arbitrary point in the data sample, AM effects where the amplitude envelope has a combination of effects that include sloping upward or downward or leveling off or transitioning smoothly from one AM envelope state to another, and any combination of these states.

In accordance with another exemplary and non-limiting embodiment, a plurality of amplitude effects, such as commonly known amplitude effects within a library of possible known amplitude effects, may be applied in turn to a reference signal that may then have a high-resolution transform/FFT applied to it. Within a complex spectral phase evolution representation of a signal, an oscillator peak of an underlying signal that was modified by some amplitude effect may be analyzed, in order to determine which of the set of possible amplitude effects, when applied to the underlying signal/stable oscillator, results in the best fit to an actual oscillator peak of the underlying signal. Information known about the context of the signal, such as whether it is speech versus artificial sound, may be used to provide further assistance in the determination of what amplitude effect is likely the best representation of the change in amplitude over time of the underlying signal.

In accordance with exemplary and non-limiting embodiments, transient signal elements (onset and stop) may be treated as AM signals in a super resolution signal processing method. In addition to onset and stop, other transient signal elements including, but not limited to, rising up, rising down, or a generic envelope may be so treated. Mathematically, a sharp noise that occurs over a short time may be considered transient on some scale, where the short time duration of the noise is shorter than the sample window time. A short enough event may tend to have a very sharp envelope, and that envelope itself may be like an AM effect. As a result, in some examples, the present methodology may be configured to handle transient signal elements as manifesting themselves as AM signal effects.

In accordance with one or more examples, the signal component tracker/aggregator/selector/separator 214 as illustrated in FIG. 2, and hereinafter referred to as the signal component tracker 214, may be described. The function of the signal component tracker 214 in accordance with one or more examples may be to group and extract oscillator peaks for subsequent re-synthesis or output into one of the output formats.

Figure 13:
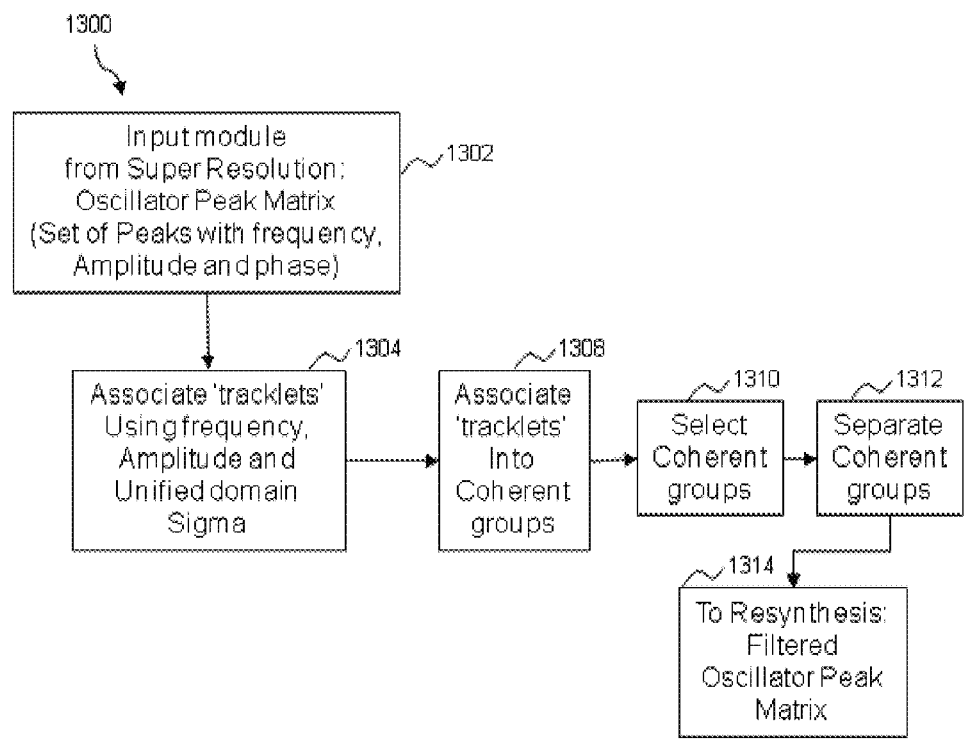
FIG. 13 illustrates an example of a method performed by a signal component tracker according to an exemplary and non-limiting embodiment.

FIG. 13 illustrates an example of a method 1300 performed by the signal component tracker. The signal component tracker may include an input module that may be configured to receive sets of signal oscillator peaks constructed by either the Single Channel Super-Resolution module or the Unified Domain Super-Resolution Module. Signal oscillator peaks may be given structure and organization by tracking methods. The oscillator peaks may be organized into sets of oscillator peaks, where each member of a set may be determined to be caused by the same oscillator ("Tracklets"). The method 1300 may include, at 1304, using the input provided by the input module 1302 to associate 'tracklets' using an association criteria that may include frequency, magnitude, Unified Domain Sigma, and other attributes to identify peaks from the same oscillator. The method 1300 may further include, at 1308, associating the 'tracklets' using their harmonic relationships to identify sets of tracklets created by the same source to group these tracklets into one or more "Coherent Groups". The grouping of tracklets may be performed using any of a plurality of tracking algorithms known in the art. Further, the method 1300 may include, at 1310, selecting the coherent groups and at 1312, separating the coherent groups to provide a filtered oscillator peak matrix 1314 for re-synthesis.

In an example, the tracking algorithms known in the art may include a Multi-Hypothesis Tracking (MHT) method. The method may include preserving multiple possible data associations until data is received that may confirm a correct association. In some other examples, the tracking algorithm may use other well-known algorithms to associate tracklet to oscillator peak, such as Greedy, Munkres, or JVC. In an algorithm, a Kalman Filter may be applied to predict the motion of a tracklet in several dimensions including, but not limited to, frequency and amplitude. Further, well-known grouping algorithms may also be applied to the problem of identifying tracklets emanating from the same source, such as Union Find. For example, a Track Fingerprinting algorithm may be used, which works by identifying individual signal sources using the source's harmonic patterns.

Thus, in accordance with an exemplary and non-limiting embodiment, a signal processing method may include super-resolution analysis and grouping of signals into frequency groups of tracklets, which form representations of the time evolution of oscillators, and aggregating the data into coherent groups of tracklets via a grouping algorithm to identify coherent groups of frequencies within a signal. The grouping into tracklets may be performed using a tracking algorithm such as Kalman Filter, greedy association or any other such algorithm as known to those skilled in the art, to identify short term stable oscillators that may come and go as a signal source evolves through time. The data may be further divided into coherent groups of tracklets using combinations of well-known track grouping algorithms, such as, without limitation, union find.

In some examples, the analysis may be used to aggregate signal elements into tracklets.

In some examples, partitioning may be used to aggregate signal elements into coherent groups.

In some examples AM and FM affects may be detected and/or corrected using the measured evolution of frequency and amplitude of oscillator peaks contained in a tracklet.

In some examples, the evolution of frequency and amplitude in a tracklet or a coherent group may be used to identify speech or non-speech. For example, speech tends to curve through frequency over time, whereas non-speech is often flat in frequency as it evolves in time.

In some examples, a human may be presented with an interface to view oscillator peaks, tracklets and coherent harmonic groups.

In some examples, a human may assist the system in determining which oscillator peaks, tracklets and harmonic groups may be output or accentuated.

In some examples, the system may learn from a human's choices about which oscillator peaks, tracklets and harmonic groups should be kept.

In some examples, the system may learn vocal patterns of an individual speaker or signal source. These patterns may include harmonic separation, rates of change of frequency and/or amplitude, or aggregations of any other data that may be contained in the oscillator peak.

In some examples, the oscillator peak detection, tracking and grouping process may be used for audio signals.

In some examples, the oscillator peak detection, tracking and grouping process may be used for any signal, including, but not limited to RADAR, SONAR, LIDAR, and sound/audio, video, and vibration sensors.

In some examples, the tracklets may be used to form coherent groups. That process of forming coherent groups is called "partitioning" in the tracking. For example, in sound sources, each tracklet may represent a harmonic. A tracklet may typically move through frequency, time and direction of arrival (that is, related to the sigma of the unified domain) and may vary in amplitude along the tracklet. These shapes represent AM or FM effects that are detected. "Grouping" as used herein may refer to attempts to find the harmonics amongst tracklets that may be moving together and may be from one coherent source. When viewed visually, as described below, sweeping curving lines in a time-frequency representation of a sound signal may be typically indicative of speech, while flat horizontal lines may be often indicative of artificial noises, such as car alarm sounds. As a result, naturally occurring versus artificial sounds can be separated by, for example, shape and type in the partitioning. Separation can also be based on any other parameters that may be calculated in the analysis process. As a result, an automated algorithm may be employed to eliminate artificial sounds or enhance artificial sounds as desired for a given application. In accordance with exemplary and non-limiting embodiments, a user interface may be provided for viewing a signal as a plurality of potentially coherent tracklets in order to edit the visual representation to identify signals as belonging to a desired tracklet or coherent group and scoring an element of the signal based on feedback from the editing of the visual element. In other embodiments, a sound signal, such as based on speech from an individual may be introduced for identifying parameters that may facilitate grouping of tracklets that correspond to signals produced by the individual. In this way, one may perform learning on the patterns of a speaker such that there is derived a characteristic feature set for that speaker. In another embodiment, speech originated by an individual may be identified based on "fingerprinting" of a source based on unified domain parameters that are characteristic of the known signature or "fingerprint" of the source/individual. In other embodiments, the source signal may be any of the other types of signals discussed within the scope of this disclosure.

In addition to well-known tracking algorithms, the tracker may employ new algorithms to improve output quality. For example, a Phase prediction algorithm may be used to predict the likelihood that two peaks emanate from the same sound source. In an example, peak correction may be performed using Phase Prediction.

Figure 14:
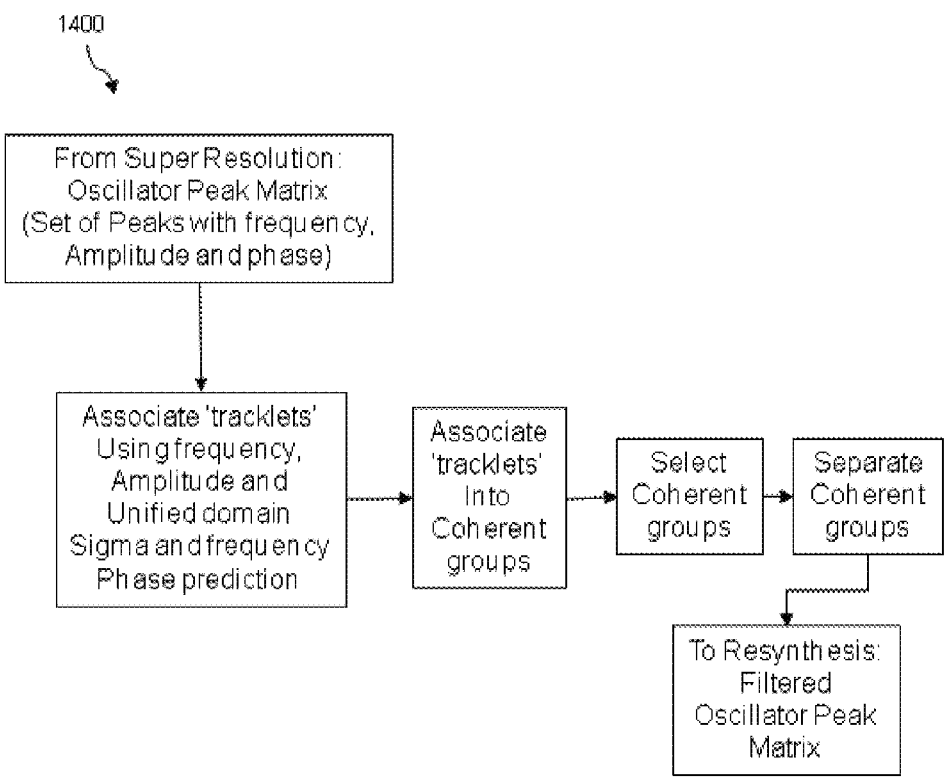
FIG. 14 illustrates an example of a method performed by the signal component tracker that may use frequency and phase prediction according to an exemplary and non-limiting embodiment.

FIG. 14 illustrates an example a method 1400 performed by the signal component tracker 214 that may use phase prediction. The method 1400 may use phase prediction as a criteria for associating 'tracklets' in addition to the association criteria discussed on in FIG. 13. In some examples, the output of frequency-phase prediction may cause the tracker to re-calculate the parameters associated with an oscillator peak. In some examples, peak correction may be performed using proximity. For example, the tracker may calculate that two oscillator peaks are interfering, and may use the track state information to correct that interference. The oscillator peaks may then be selected for providing an output.

In an example, the methods of peak selection may include, but are not limited to, evaluating the peak using parameters, such as Unified Domain Sigma, Frequency, and Amplitude, evaluating the tracklet to which the peak belongs using parameters, such as Unified Domain Sigma, Frequency, and Amplitude, evaluating the coherent group to which the peak may belong using parameters, such as Unified Domain Sigma, Frequency, and Amplitude, evaluating whether the coherent group to which the peak may belong matches a desired speaker using harmonic "fingerprinting," using frequency-phase prediction to identify whether the tracklet appears to be a 'direct-path' source, and may discount peak's parameters that may fail to pass the peak prediction tests when evaluating a tracklet's or a coherent group's parameters, or estimating a distance by combining the Unified Domain Sigma with the phase information.

As previously discussed, a tracklet may be defined as a grouping of oscillator peaks that may be determined to emanate from one source harmonic. In an example, a tracklet formation process may be performed on the basis of an input comprising a set of oscillator peaks extracted from a single sample window. Tracklets may then be formed using many different well-known track association methods and algorithms. The algorithms may involve a method that may predict a tracklet forward, a method that may compute a cost of association between a tracklet and a new piece of data (in this case, an oscillator peak), and a method that may choose an optimal set of assignments. By way of example, the tracklet prediction algorithm may include, but are not limited to, linear prediction, and Kalman Filter prediction. In some examples, the cost estimation algorithms may include, but are not limited to, statistical distance calculation, such as a Mahalanobis Distance, and simple distance calculations, such as difference in frequency and amplitude. Further, in an example, assignment algorithms may include, but are not limited, to Greedy Association, Munkres Association, and JVC association.

The output of the tracklet formation process may include a set of oscillator peaks that have been formed into tracklets.

As previously discussed, in some examples it may be desirable to form coherent groups. A coherent group may be a set of tracklets that may have been determined to be produced by the same sound source.

In accordance with exemplary and non-limiting embodiments, a signal processing method may include super-resolution analysis, assigning signal elements into frequency tracklets from snapshots in time (wherein the snapshots in time may indicate using a sample window of data starting at an initial time and ending at a final time, multiplying it by an analysis window, and converting it to the frequency domain), that is to say, organizing the data into tracklets by a tracking algorithm to identify frequency tracklets within a signal, and using at least one of the frequency, angle of arrival, amplitude, and slope of the amplitude of a track in order to assist in grouping tracklets into coherent groups.

As previously discussed, in some examples it may be desirable to form coherent groups. A coherent group may be a set of tracklets that have been determined to be produced by the same sound source. In an example, coherent groups may be formed by a process that may receive a set of tracklets as input. The set of tracklets may then be partitioned into disjoint sets. There are several well-known algorithms for partitioning the sets of tracklets into disjoint sets. For example, the Union Find algorithm may be employed. For most of the algorithms, a cost function may need to be calculated to compute the likelihood that two tracklets are from the same source. These cost functions may use any of the features stored in a Singlet representation of an oscillator peak including, but not limited to, frequency, amplitude, Unified Domain Sigma, and phase. These cost functions may rely on knowledge of the harmonic structure of a speaker. As a result of performing the coherent group formation process, as an output, a set of tracklets that have been formed into coherent groups may be generated.

In accordance with an exemplary and non-limiting embodiment, a unified domain directional estimate may be used with the outputted set of tracklets to identify a tracklet of interest.

In some embodiments it may be desirable to predict the evolution of phase as an oscillator evolves through time and frequency. Knowledge of predicted phase may be used in several stages of processing, including, but not limited to the activities discussed in the above description, including scoring the likelihood that a peak should be associated with a particular tracklet, detection and/or repair of results from interfering signals, detection and/or repair of dropped out or missed signals, detection of direct-path versus non-direct-path signals, compression algorithms, and association of tracklets into coherent groups.

In an example, the basic model of the signal may be taken as the projection into the real numbers of the general complex form $s(t)=r(t)e^{i\Theta(t)}$. Further, it may be assumed for the example that over a short period of time the amplitude term may remain constant, that is to say, $r(t)=r_0$, then the rate of change of the signal may be related to the rate of change of θ and this may then be related to the instantaneous frequency. This may give $$\frac{ds}{dt} = ir_0 \frac{d\theta}{dt} e^{i\theta(t)}$$

and since the rate of change of θ may include the instantaneous frequency, this may give a way to relate the frequency and phase of a signal that may be evolving in time. In practice, the parameters may be estimated based on the measured data, and the high-resolution analysis may make it possible to make accurate estimates of the instantaneous frequencies, and hence accurate predictions of future frequency and phase values.

The algorithm for frequency phase prediction may start with the differential equation relating phase and instantaneous frequency, $$\frac{d\theta}{dt} = f(t)$$

and over a sufficiently short window of time, f(t) may be approximated as a constant plus linear term (and for one skilled in the art the expansion can be continued easily to higher order terms), giving $f(t) = f_0 + at$.

The example may further include estimating the frequencies from the data, and this may be done using the super-resolution analysis from the CSPE family of transforms. In an alternate example, the frequency estimate for a given sample data window, say the $i^{th}$ window, may be assumed to be most accurate at the center of the window—which may hereinafter be referred to as $f_i$. The best position for the frequency estimate may be obtained by a variety of other methods, including but not limited to, checking zero crossing rate, looking at residual error after fitting with the frequency estimate and the like. The super-resolution frequency estimate for the $j^{th}$ window may be given by $f_j$ and it may be assumed to be most accurate at the middle of sample data window j (or again positioned by a variety of other methods). Thus the super-resolution frequency estimates and the related times where the estimates are positioned may be obtained. If the differential equation may be solved assuming boundary conditions that may be consistent with the frequency estimates, the first order approximation may include $$a = \frac{f_j - f_i}{2T}$$

where T may be the time between the two frequency estimates (and in a preferred embodiment may be taken to be the time shift between the two sample data windows). The net result may be that one may derive the phase as a function of time, giving $$\theta(t) = 2\pi \left( f_i t + \frac{f_j - f_i}{2T} t^2 \right) + \theta_0$$

where $\theta_0$ may be the initial phase of the signal. The approach presented here may be shown to be highly accurate when used with the super-resolution frequency estimates.

In some examples, the phase of a tracklet may be predicted to a different time. The difference between that prediction and a new oscillator peak's measured phase may be used to score the likelihood that the new peak should be incorporated into the tracklet.

In some examples, if two tracklets may be determined to be interfering, the predicted frequency and phase of each tracklet may be used to repair the interfering regions so that the combined signal power may be reassigned to the interfering tracklets.

In some examples, if a tracklet may be determined to be missing data in a given frame, an estimated oscillator peak may be inserted using a predicted frequency, amplitude, phase, modulation type, direction of arrival, and any other characteristic that may be included in the tracked oscillator peaks.

In some examples, a difference between a tracklet's predicted phase and actual phase may be used to determine whether it traveled to the sensor in a direct path or via an indirect path.

In accordance with another exemplary and non-limiting embodiment, the frequency/phase of signal representations may be predicted based on super-resolution, unified domain model of coherent signal elements within a signal, and a signal element may then be processed based on the prediction. For example a prediction of every other frame may be used, allowing skipping of the processing of the predicted frame. As a result, for example, it may only be necessary to process frames 1, 3, 5, 7 in order to predict frames 2, 4, 6 and 8. In this example, a prediction of frame 2 may be performed and further an estimate of what frame 2 turned out to be may be done, thus providing a measurement of accuracy. In this way, it may be determined, for example, how closely did two spectral peaks so created line up. If the alignment is above a certain tolerance, frame 2 may be recalculated to make sure that it may be within an acceptable and predetermined range of error. If the alignment is within the accepted tolerance, then no further prediction may be required.

As described above, in accordance with exemplary and non-limiting embodiments, one may predict the frequency/phase of signal representations based on a super-resolution, unified domain model of coherent signal elements within a signal. The resulting models may be accurate enough to allow for the prediction of the evolution of signal elements through frequency, amplitude, phase, and time. As a result, if some data may be missing, it may be possible to keep the signal element tracks/tracklets going across gaps. In the instance of tracklet intersection, predicted values may be utilized to determine the behavior and direction of the underlying tracklets. In one embodiments, predictive interpolation of gaps in signals may be performed both forward and backward to determine a consistent estimate of the missing or obscured data. In one embodiment this may be implemented on a cell phone network to ameliorate the effects of dropped packets.

In other examples, the frequency and/or phase of signal representations may be predicted based on a super-resolution, unified domain model of coherent signal elements within a signal and grouping a signal element with other elements based on the prediction. The measurements of the signal are typically accurate enough to allow for prediction forward in time in a manner that is more accurate than random. Put simply, it may be predicted that a tracklet goes somewhere, and then when an observation regarding such a tracklet with those properties is made, it may be derived that the observed phenomenon is in fact associated with a signal element encountered before.

In accordance with another exemplary and non-limiting embodiment, the frequency/phase of signal representations may be predicted based on super-resolution, unified domain model of coherent signal elements within a signal, and a signal element may then be processed based on the prediction. For example a prediction of every other frame may be used, allowing skipping of processing of the predicted frame. As a result, for example, it may only be necessary to process frames 1, 3, 5, 7 in order to predict frames 2, 4, 6 and 8. In this example, a prediction of frame 2 may be done and a quick estimate of what frame 2 turned out to be may also be performed, thus providing a measurement of accuracy. In this way, one may determine, for example, how closely did two spectral peaks so created may line up. If the alignment may be above a certain tolerance, frame 2 may be recalculated to make sure that it may be within an acceptable and predetermined range of error. On the other hand, if the alignment may be within the accepted tolerance, then no further prediction may be required.

In some examples, the frequency/phase of signal representations may be predicted based on super-resolution, unified domain model of coherent signal elements within a signal and may be used to provide data to complete an incomplete signal representation based on the prediction.

In some embodiments, frequency/phase of signal representations based on super-resolution, unified domain model of coherent signal elements within a signal may be predicted and used to process a signal element based on the prediction, wherein processing the signal element may include using the prediction to facilitate compression of a representation of the signal. As above, by not having to process every frame, the information retained in the mathematical representation can be represented with far fewer bits than the original data (that is to say it may be naturally compressed).

The oscillator peak detection stage may use information from the current state of the tracking and/or grouping stages to guide its processing decisions. Techniques may further include reduction of interference by track aware fitting and prioritization of oscillator peak selection, as described below.

In an exemplary technique, reduction of interference through track-aware fitting may be implemented. When two oscillator peaks are on nearly the same frequency, they may interfere, and be indistinguishable. If two tracklets are detected to be on a trajectory that will intersect in frequency in a given frame, one may use predicted frequencies and amplitudes to create two oscillator peaks where the system may only detect a single peak that is the sum of both oscillators.

In another exemplary technique prioritization of oscillator peak selection may be done. Due to computational resource limitations, or a desire to optimize performance or battery life or a number of other features, the system may fit fewer oscillator peaks than it detects. The system may use the tracklet and/or group state information to pick the oscillator peaks to fit. For example, in sound processing, if a speaker of interest may show a consistent harmonic separation, the system may first attempt to find oscillator peaks that may fit the existing pattern. Similarly, psycho-acoustic measures of the importance of signal components may be used to prioritize which oscillator peaks should be processed.

In another exemplary technique extraction of desired signals from noisy environments or enhancement of desired signals in noisy environments—the tracking and grouping algorithms may be used, along with any of the measured parameters of the fitted data, to determine which tracklets or coherent groups should be extracted from the noise, or enhanced over the noise.

In accordance with an exemplary and non-limiting embodiment, an ambiguity measure or certainty measure may be assigned to the tracklets by the tracker. This ambiguity measure may be used in a Kalman filter, a Bayesian decision process, a scoring function or a similar process whereby the certainty/ambiguity measure is used to determine which tracklets or coherent groups should be extracted or enhanced. In yet other embodiments, the intersection of a plurality of tracklets may be identified with prediction of tracklet direction used to assist in the handling of intersection points. For example, in sound processing, when tracklets actually cross, one merged sound at one frequency may be observed. In this example, the merged sound may be taken at an intersection point and may be assigned to each of the tracks so that they may be self-consistent.

In an example, the output may include a subset of the peaks that were received on input. In some cases, these may be modified, such as in the case of frequency phase prediction correction.

A range of techniques may be used to identify relevant oscillator peaks and tracklets. In an example, a processor may receive a plurality of oscillator peaks and may select one or more of the plurality of oscillator peaks for re-synthesis.

In an alternate example, oscillator peaks may be scored to determine which are desired for output. Oscillator peaks may be scored using at least one of time, frequency, phase, amplitude, and unified domain direction of arrival.

In an alternate example, tracklets may be scored to determine which are desired for output. Tracklets may be scored using at least one of time, frequency, phase, amplitude, unified domain direction of arrival, change in any of those characteristics, and predictability of change in any one of those characteristics.

In an alternate example, coherent groups of tracklets may be scored to determine which are desired for output. Coherent groups may be scored using at least one of time, frequency, phase, amplitude, unified domain direction of arrival, and change in any of those characteristics, and predictability of change in any one of those characteristics, and conformance to a known harmonic structure, such as a person's known harmonic frequency patterns.

In an alternate example, a peak, tracklet, or coherent groups score may be used to assign it for output, or eliminate it from output.

In an alternate example, a peak, tracklet, or coherent group's score may be used to modify its amplitude in output, thereby reducing or amplifying its impact.

In an alternate example, a peak, tracklet, or coherent groups score may be communicated to another system, such as a speech recognizer, to aid it in its estimation process.

In an alternate example, original signal may be combined with reconstructed signal for output. Either the original or reconstructed signal may be diminished or amplified before combination.

In an alternate example, elements such as background noise, other interfering signals, or any other signal with undesirable characteristics may be rejected or diminished.

In an alternate example, elements such as background noise, secondary or other interfering signals may be revealed by removing a primary signal that may be obscuring the background.

In some examples the signal channel re-synthesis module 220, as illustrated in FIG. 2 may be used in accordance with one or more examples to create a frequency domain representation of the targeted oscillator peaks in a single output channel. In an example, the selected oscillator peaks may be converted back to frequency or time-domain signal using single channel re-synthesis. For some applications, such oscillator peaks may be the output of the system.

The input to single channel re-synthesis module 220 may be a set of oscillator peaks containing the parameters that may be used to create frequency domain representations of those oscillator peaks in a single channel. In one or more examples, the oscillator peaks may generally contain any of the parameters, including but not limited to, frequency, amplitude and phase. Further, the parameters of the analysis window used with Sample Window (A) and Sample Window (B) may be those determined in the single channel pre-processor.

In some examples, the single channel re-synthesis module 220 may be configured to perform a method to use each oscillator peak received at the input to calculate a frequency domain data projection. The method may include creating a normalized frequency domain representation of the oscillator by sampling the high resolution frequency domain version of the analysis window used to taper Sample Window (A) and Sample Window (B) in the Single Channel Pre-Processor. Multiply the normalized frequency domain representation of this oscillator by the oscillator peak's amplitude and phase. The method may further include, summing the spectrum created previously, once the frequency domain data corresponding to the oscillator peaks has been calculated. In an example, if time-domain data may be required, an inverse-FFT (iFFT) may be performed that may convert the frequency output to the time domain.

In some examples, some amount of background signal may be required to provide desirable characteristics in the output. An advantage of the methods used herein is that the phase of the output signal may be preserved with high accuracy. As a result, the phase of the samples in the original signal may match the phase in the extracted and re-synthesized signal. In some circumstances, addition of the background signal may yield a result that has desired characteristics. This may be achieved by a variety of techniques, including mixing back in the original signal or an attenuated or amplified version of the original signal. In some examples, it may be desirable to use the singlet representation of the original signal, such as a singlet representation in a compressed form, so that the original signal may be reconstituted before remixing with the extracted signal.

Based on the method performed by the single channel re-synthesis module 220, a set of frequency domain or time-domain data that accurately represents the portions of the original signal corresponding to the selected set of oscillator peaks may be obtained as the output from the single channel re-synthesis module 220.

In some examples the multi-channel re-synthesis module 222, as illustrated in FIG. 2 may be used in accordance with one or more examples to create a frequency domain representation of the targeted peaks in a multi-channel output. The multi-channel re-synthesis module 222 may be configured to convert selected oscillator peaks back to frequency or time-domain signals. In some examples, such oscillator peaks may be the output of the system.

The multi-channel re-synthesis module 222 may be configured to receive as an input, a set of oscillator peaks containing the parameters used to create frequency domain representations of those oscillator peaks in multiple channels, and the parameters of the analysis window used with Sample Window (A) and Sample Window (B) in the multi-channel pre-processor 210. In an example, the oscillator peaks may contain: frequency, amplitude, Unified Domain Sigma, and the phase of the oscillator peak in each channel.

The multi-channel re-synthesis module 222 may be configured to perform a method for each oscillator peak to calculate its frequency domain data projection for each channel. The method may include calculating the amplitude for that channel for that peak using the Unified Domain Sigma and the input amplitude. The method may further include creating a normalized frequency domain representation of the oscillator by sampling the high resolution frequency domain version of the analysis window used with Sample Window (A) and Sample Window (B) in the Single Channel Pre-Processor. Multiply the normalized frequency domain representation of this oscillator by the amplitude calculated in step 1 and the oscillator peak's phase for that channel, as received in the input. The method may further include summing the spectrum created in the previous step once the frequency domain data corresponding to the oscillator peaks has been calculated. In an example, the frequency domain for channel X may be the sum of all the calculated frequency domain spectrum for channel X for all oscillator peaks. If time-domain data may be required, an inverse-FFT (iFFT) may be performed to convert the frequency output to the time domain.

In an example, a re-synthesized signal may be built in a signal processing model, using a convolutional model and using distinct methods to build each of a plurality of signal elements or characteristics, including stable frequency signals, FM peaks, and AM peaks. Oscillator peak parameters, including frequency, amplitude, frequency modulation and amplitude modulation may be re-calculated to predict the parameters that may exist in a different window position (such as slightly later in time) or window length as follows:

In an example a different window length may be chosen for resynthesis than may have been used for oscillator peak detection. This may enable the system to use a more optimal window length for re-synthesis than may have been used for oscillator peak detection.

In an example, the length of the sample window may be adjusted as necessary. Under certain condition, it may be optimal to use a sample window of a different length. This may be done because the parameters of the detected oscillator peaks may be adjusted for comparison. For example, during periods of intense frequency modulation it may be advantageous to sample more frequently.

In some examples, frames may be shifted within re-synthesis. For example, a first snapshot of a signal may be taken using for example, from 0 to 1024 data points. A next might start with data point 512 and continue to data point 1536, shifting one-half of the window length. If changes on a smaller scale may be desired, shifting by fewer data points may be desired (such as shifting by 256), then shift again, in which case each signal element is covered more closely. At re-synthesis, just the middle segments may be used (256 to 768 and 512 to 1024) and predicting forward within a frame may be done to make smaller frames. For example, if while processing a video input signal and sending video from wide screen format to old fashioned television, operation may be changed on the fly so that the center of the TV image may be reproduced and the edges may be eliminated without decreasing quality and without being required to undertake complicated manipulation of the frames.

Based on the method performed by the multi-channel re-synthesis module 222, a window of data in the frequency or time domain that may accurately represent the portions of the frequency domain from the original signal corresponding to the selected peaks may be obtained as the output from the multi-channel re-synthesis module 222.

The signal separation (SS) technology described herein may be applied to any system that may send or capture signals through a collection mechanism (such as including a microphone, a camera, radio receiver, a video camera, a transducer, or other receiver) for either transmission, storage, analysis or manipulation. The signal may subsequently be (but not limited to): transmitted between receivers (e.g. RF transmission); delivered in an audio format, such as for transmission of a voice call, delivered in an image or video format such as transmission of a photo or video, depicted in a text-format such as converted from speech to text, or interpreted and rendered as an image such as a radar display or ultrasound.

In some embodiments, SS technology may be introduced into one or more processes and/or systems that involve digital signal processing. Digital signal processing is generally defined as the mathematical manipulation of an informational signal to modify or improve it, and may be characterized by the representation of discrete time, discrete frequency, or other discrete domain signals by a sequence of numbers or symbols and the processing of these signals. Sample digital signal processing fields where SS technology may deliver benefit may include but are not limited to, audio processing and compression, speech processing and recognition, RF transmission, biometric analysis, sonar and radar, sensor array, ultrasonic testing, spectral estimation, statistical analysis, digital image, digital and cellular communications, control systems, biomedical, medical imaging, and seismic data. Digital signal processing may be applied to measure, filter and/or compress continuous real-world analog signals. The process may typically begin by converting the signal from an analog to a digital form, by sampling and then digitizing it using an analog-to-digital converter (ADC), which may turn the analog signal into a digital stream of numbers. Typically, after analysis and transmission, the required output signal may be another analog output signal, which requires a digital-to-analog converter (DAC).

In some embodiments, the SS technology may be implemented on, but not limited to, one or more of the following: general purpose computers and GPUs; specialized single and multi-core processors (such as Digital Signal Processors); purpose-built hardware such as application-specific integrated circuit (ASICs); field-programmable gate arrays (FPGAs); digital signal controllers; and stream processors. In addition, the SS technology described herein may be implemented as firmware, embedded software, a software platform, a standalone software application, and/or a network or cloud-based application/service. Such implementations may be applied, but not limited to: computers; cellular phones or smart phones; tablets; or other communications; audio, video, sensor, radar, sonar or medical-imaging devices or systems; or any other system or device whereby digital signal processing may improve performance or general usefulness.

In some embodiments, the signal separation technology described herein may be utilized in Radar-based object detection and tracking systems that rely on radio waves as a method to determine the range, altitude, direction, speed or other characteristics of objects. The radar systems may incorporate a process of transmitting pulses of radio waves (or microwaves), which are reflected off any object in their path, and subsequently return a portion of the wave's energy to a receiver. Some exemplary uses of radar may include, but are not limited to: general imaging, air defense and anti-missile systems, air traffic control, marine systems to locate terrain, vessels and other marine-based points of interest, aircraft anti-collision systems, ocean surveillance systems, outer space surveillance and rendezvous systems, meteorological tracking and monitoring, altimetry and flight control systems, guided missile target locating systems, terrain mapping, detection and location systems, oil and gas discovery and drilling systems, and ground-penetrating radar for geological observations.

In some embodiments, the SS technology may be applied to the radar systems to mitigate "noise", "interference", and/or "clutter" at any point within the process and thereby enhancing the quality of the final data delivered to the end use application. The SS technology may be introduced independent of any other correction algorithms and systems or in conjunction with one or more of such systems, such as: pulse-doppler, moving target indication, automatic gain control ("AGC"), 3D mapping imaging applications, and/or horizontal, vertical, linear and circular polarization. Reflected signals decline rapidly as distance increases, so noise introduces a radar range limitation, and the lower the power of the desired signal, the more difficult it is to discern it from the noise. Radar systems must be configured to overcome unwanted signals, that is to say both passive signals and active signals, while focusing on the actual targets of interest. Overcoming unwanted signals may define a radar system's signal-to-noise ratio ("SNR"), comparing the level of a desired target signal to the level of background noise or interference.

In an exemplary embodiment, introduction of SS technology may increase a radar system's SNR that may result in delivering improvements in isolating actual targets from the surrounding noise signals, interference and clutter. In an example, noise and interference may be caused by any of the factors including, internal source of random variations in the signal, which may be generated by all electronic components; random variations superimposed on the desired echo signal received in the radar receiver; and/or external sources, such as thermal radiation of the background surrounding the target of interest. In addition, clutter may be caused due to radio frequency echoes returned from targets which are uninteresting to the radar operators. Such targets may include natural objects (such as rain, birds); atmospheric turbulence and other atmospheric effects (such as ionosphere reflections); man-made objects (such as buildings); and/or even radar countermeasures such as chaff. Some clutter may also be caused by a long radar waveguide between the radar transceiver and the antenna. The SS methods and techniques described herein may serve to effectively mitigate interference from the above and other interfering signals. The SS technology may be applied to all forms of radar signals, equipment and imaging software and hardware, regardless of frequency bands, scan types, display processors and systems utilized, and/or end uses and links. The technology may also be applied to other systems that make use of other parts of the electromagnetic spectrum. One example of such a system may be "LIDAR", which uses visible light from lasers rather than radio waves. In addition, the technology may be applied to other radiofrequency-based (RF) systems, such as a scalable multifunction RF system which enables RF functionality (e.g. radar, communications, and electronic warfare) to be extended, identified, separated, concealed or otherwise manipulated in the performance of its functions.

In accordance with an exemplary and non-limiting embodiment a source separated signal generated using any process or combination of the previously described techniques herein may generate outputs presented as: (i) an audio file; and/or (ii) audio signal components; and/or (iii) speech feature vectors, all of which alone or in combination can serve as the inputs to a speech recognition engine or biometric voice identification system. In some embodiments, the signal separation technology described herein may be utilized in speech recognition systems which may be used to such as, translate spoken words into text, control automated systems through voice translation, or convert spoken words into other outputs other than voice through an automated process. Introduction of SS to improve speech and voice recognition may be applied independently of any other algorithms and systems used to improve recognition, or in conjunction with one or more of such systems. Additionally, SS may be applied such as to original voice source signals that may have been converted to digital signals and reconverted to analog signals prior to once again being converted to digital to be processed for speech recognition, or, to the audio signal once it may have been converted to digital format immediately prior to the speech recognition process.

Speech recognition may be referred to as "automatic speech recognition" ("ASR"), "computer speech recognition", and/or "speech to text". These systems may use training, such as in the case of "Speaker Dependent" systems or not use training by a speaker (referred to as "Speaker Independent" systems). Voice recognition generally refers to finding the identity of who is speaking, in contrast to what they are saying. Recognizing the speaker may simplify the task of translating speech in speaker dependent systems or it may be used to authenticate or verify the identity of a speaker as part of a security process. In some embodiments, applying SS to speech recognition may include conversion of analog voice signal into digital audio and then into recognized speech. In an example, the conversion may be performed through a process that may include, transforming the digital audio into a better acoustic representation, applying rules so the speech recognizer knows what phonemes to expect, and determining which phonemes are spoken, and converting the phonemes into words. The digital audio format may vary in terms of number of channels (such as mono vs. stereo), bitrate, and/or other characteristics.

Speech recognition may also include extracting feature vectors from speech waveforms. The extraction may be achieved by first transforming the digital audio into the "frequency domain" using a windowed Fast-Fourier Transform (FFT), with a resulting output similar to what a spectrograph produces. In this domain, the frequency components of a sound for a given sample rate may be used to generate a graph of the amplitudes of frequency components for that sample. A feature vector may be computed from a window of speech signals in every short time interval, and an utterance may be represented as a sequence of these feature vectors.

In some embodiments, an automated speech recognizer engine may consist of a database of thousands of such graphs correlated to different types of sounds produced by the human voice, and the graph generated at that sample may be matched against the database, producing a number that describes the sound. The most likely word sequence for the given speech feature vectors is found using two types of knowledge sources, that is to say, acoustic knowledge and linguistic knowledge. Speech recognition engines may use a mathematical technique called "Hidden Markov Models" (HMMs) for the acoustic features of speech sound and the stochastic language model may be used to represent linguistic knowledge. In some examples, interferers such as loud background noise or other ambient environmental sounds may often lead to misinterpretation of the source, resulting in the recognizer to determine a different vector than it would have if the user were in a quiet room with a high-quality microphone. Traditionally, background noise and variability problems have been addressed using statistical models to figure out which phoneme is spoken; however, with strong interference the results are generally poor. In an embodiment of applying SS technique to speech recognition process, introduction of SS in the initial steps of the recognition process, whereby the feature vectors are extracted from speech waveforms may greatly increase the robustness of determining the phonemes and utterances with a much higher confidence than other approaches. Application of SS may greatly mitigate the impact of interferers like ambient noise when extracting the feature vectors from the digital audio signal. SS processed signals may offer higher accuracy for voice recognition/identification and may be introduced into any existing voice recognition or voice security system, using either onboard processing (as with cell phone, tablet and other personal device security features) or linked to a network or cloud for controlled access devices or areas (such as restricted access facilities, buildings, vaults or other secured locations). For voice/speaker recognition, similar processes may be used to extract feature vectors of the speaker of interest; however, these vectors may be compared and contrasted to a model/library of utterances originally created by the speaker, and a similarity score may be generated. The SS technology may be introduced to voice recognition to enhance the robustness of the scoring by mitigating interference such as background noise or competing conversations by delivering improved feature vectors through any of the methods including but not limited to application to the original voice source signals that have been converted to digital signals and reconverted to analog signals prior to once again being converted to digital to be processed for speech recognition, or, application to the audio signal once it has been converted to digital immediately prior to the voice recognition process. SS methods and systems described herein may be implemented as hardware or software on any PC, cell phone, tablet, or other system using voice/speech recognition, as a stand-alone processing technique or an add-on to existing software program.

In accordance with exemplary and non-limiting embodiments, a representation of signal elements may be developed in a model of a signal. The signal may be decomposed and grouped into tracks and/or tracklets corresponding to individual speakers, and the decomposed signal transformed into feature vectors adapted for use in a speech recognition engine. In such embodiments, one might develop and introduce a bias toward a specific speaker (e.g. the owner of a phone), so as to automatically pull out their speech and enhance it over all other sounds in the environment.

In another embodiment, a representation of signal elements which may be referred to as speech features or speech vectors may be developed in a source signal separation model of a signal. The signal may then be decomposed into speech feature vectors corresponding to individual speakers, and the decomposed representation used as an input to a speech recognition engine or biometric voice identification system.

In accordance with exemplary and non-limiting embodiments, a system comprises a sound gathering device, such as a microphone, with a nearby processor for engaging in cooperative/distributed computing of source signal separation. In some embodiments, the algorithm is scalable to be less processing-intensive so it can be used on cellular phones, smartphones, tablets or other mobile devices. In some embodiments, some of the processing may be conducted on the mobile device and then be distributed or transmitted to a remote processor or server with results then delivered back to the mobile device.

In some embodiments SS techniques may be used for hearing aid applications. A hearing aid is any medical device that helps amplify and filter sounds to enable those with hearing impairments/hearing loss to comprehend sound. Hearing aids consist of microphones (directional or omnidirectional) that may convert sound to an electrical signal, which may then be processed by a digital signal processor to enhance targeted sounds and minimize unwanted background noise. The resulting targeted sounds are then amplified and rebroadcast via speakers in the patient's ear canal. Patient controls may be used for volume, noise reduction, and different environmental settings. Microphones, DSPs and controls for the device may be located on or within the hearing aid itself or in external control devices or cell phones.

In some embodiments, the methods for source signal separation described herein may be embodied in any design hearing aid device for the purposes of, but not limited to, amplifying targeted sounds, focusing on a single person speaking or sound source, focusing on limited region, such as a conversation at a table in a crowded restaurant while turning off/minimizing other sounds in the restaurant, and/or minimizing or eliminating background or other ambient noises that the user may choose not to hear and/or interfere with his/her comprehension of a desired conversation or sound source. These SS methods may be employed across any hearing assistance device including but not limited to behind-the-ear aids, in-the-canal hearing aids, open canal aids, closed canal aids, air conduction hearing aids, bone conduction/bone anchored aids, eyeglass based aids, external device-linked aids, cell phone based aids, PDA based aids, iPad/Tablet based aids, PC based aids and cochlear implants. The SS techniques may also be applied in hearing assistance devices includes both FDA-Regulated hearing aids and over-the counter non-prescription sound amplification devices.

In some embodiments, the SS methods described herein may also be linked to cell phone, television, radio, PC, Cloud, tablet and other hearing-assistance linked devices. One exemplary embodiment may be linkage to a television to enable the user to comprehend the broadcast while minimizing or turning off other background or ambient noises that may impair a user's ability to comprehend the broadcast. Likewise a similar embodiment of this application may include the amplification of a cell phone transmission processed to minimize or eliminate ambient or background noises both at the site where the user is receiving the call as well as the unwanted background noises transmitted by the caller on the other end of the line.

In some embodiments, the SS methods described herein may be intended to work with any microphone (stereo or mono, directional or omni-directional) or microphone array located on or incorporated into any hearing assistance device, or located off the hearing assistance processing device and transmitted to that device via wireless, infra-red (IR), Bluetooth, wired or other transmission methods. An exemplary embodiment may be a cell phone or tablet linked hearing aid where sound may be recorded on these devices and them transmitted to the ear for broadcast. Likewise, microphones for recording targeted sound sources may be located on the users eyeglasses, embedded into clothing or jewelry, worn around the user's neck, embedded in buttons, hats or other clothing or fashion accessories. Microphone designs, including but not limited to the above examples, may transmit targeted sounds to a processing device, where the SS methods and system described herein may be configured to process those sounds. The algorithm processing may take place on an independent DSP or in the device's CPU through embedded firmware. The deployment of these processing platforms may be on the device itself, an external control unit, a tablet, PC, PDA, cell phone or transmission through a cloud or transmission back to a central server over a cellular or wireless network. Signals recorded on bilateral hearing aids or array microphone systems may be transmitted across devices or to an external processing unit, including but not limited to those described above, for real time or near-real time processing.

In some embodiments, signals processed with the SS techniques described herein may then be re-synthesized into an output signal to be played back through a speaker in or near the users' ear, or through an neural or bone stimulation device for direct sensoneural processing. Speaker based devices for rebroadcast include open canal and closed canal systems, headphones, telephonic devices, cell phones, Bluetooth and other speaker based devices. Re-synthesized signals may be captured on the same device (such as a behind the ear hearing aid) or transmitted to the output speaker devices from an external processing unit (such as a tablet, cell phone, PC or other portable processor) and may be a single reprocessed input or the combination of many simultaneously recorded and mixed inputs from multiple recording devices. Hearing assistance technologies making use of SS processing may feature clinical programmed parameters or user controlled parameters to adjust device processing to a specific environment. An exemplary embodiment of clinician parameters would be distance based SS and background noise reduction setting that may be programmed at the time of the initial fitting or subsequently adjusted via telephonic or PC/web interface reprogramming. An exemplary embodiment of user based controls may include onboard device dials, external control units, or PC/cellphone/Tablet based applications that may allow the user to control the mix of targeted speech to background noise, the level of targeted speech amplification, the use of real-time or near-real-time transmission, distance and vector based controls to govern the area or direction in when they would like to gather targeted sound sources, the ability to tap into TV, cell phones, radios, voice control systems or other PC based devices for direct interface. Users may also have the ability to set the device for various modes, such as restaurants or close conversations, or control the lead-in time for playback such that they may determine tradeoffs between delayed lead-ins for targeted speech vis-a-vis intelligibility or naturalness of rebroadcast sounds.

In accordance with exemplary and non-limiting embodiments, a system comprises a sound gather device, such as a microphone, or a sound transmitting device for communication (e.g., using Bluetooth or other transmission protocol), with a nearby processor for engaging in cooperative/distributed computing of source signal separation. In some embodiments, the algorithm is scalable to be less processing-intensive so it can be used on hearing aids. In some embodiments, some processing may be distributed to remote server by the processor with results forwarded to the hearing aid.

Figure 15:
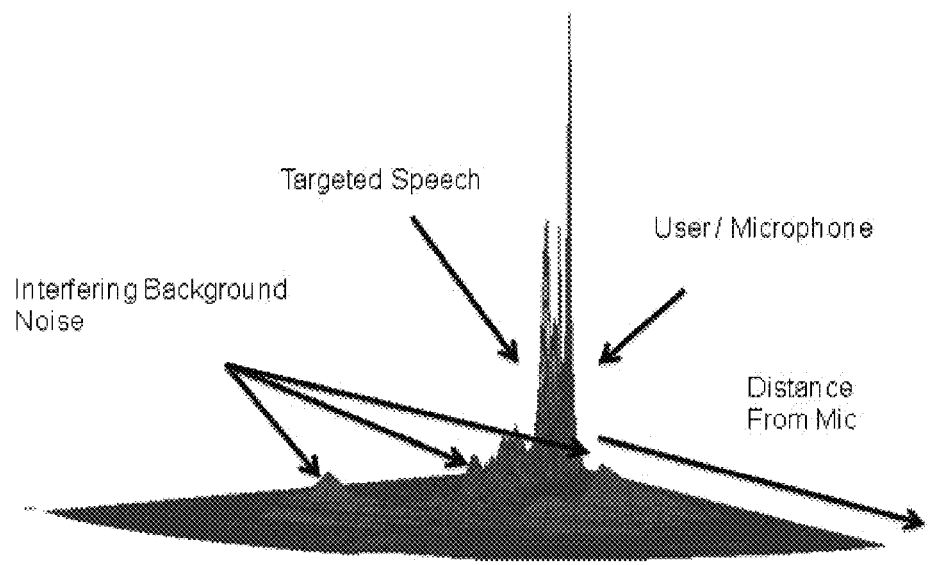
FIG. 15 is an illustration of a computer generated interface for tablet or cell phone control according to an exemplary and non-limiting embodiment.

In one variation, a cell phone can send data to a server that can perform more processing. In some instances, as when a hearing aid really needs more processing power and it can't transmit to a remote server, it may transmit to a nearby device such as a phone in your pocket. The phone may act like a local super booster or external processing system. In such an instance, the hearing aid could transition to a defined mode and use extra computing power to offload processing to the cell phone and achieve improved capabilities. In one example, controls may be placed on an actual cell phone or computing tablet such that, for example, a person sitting in a restaurant can put the cell phone down on the table and can tap a screen or move a slider control to tailor processing and source signal separation in the directions of the people sitting at the table. In response, an algorithm operates to help enhance table-mates conversation. FIG. 15 illustrates an exemplary and non-limiting representation of such a computer generated interface for tablet or cell phone control.

In another embodiment, ambient noise or unwanted background noise may be removed from an input source signal to produce a deconstructed source signal which then may be re-combined with the ambient or background noise at a lower noise level, and outputting the combined signal. In some embodiments, the user may dynamically or statically alter the noise level of the ambient noise re-introduced.

In some embodiments, the SS techniques described herein may be used in telephony applications. For mobile phone calls on cellular networks, the audio is captured through an embedded microphone and is subsequently converted from an analog to a digital signal (typically referred to as an "A to D" conversion). The resulting digital signal is then transmitted through the cellular network in a compressed or non-compressed form to an end terminus whereby it is delivered as audio output. Anywhere along the transmission process or at the endpoint of delivery, the digital signal is converted back to an analog signal. Typically, audio captured by a phone (such as a cellular phone, a speakerphone, a VoIP phone and the like) for sending may contain ambient noise or other interferences which will not inhibit the conversion nor transmission of the audio file, but may impact the general quality of the output file to the intended receiver. For example, the microphone in a mobile phone may pick up the voice of the speaker, but may also be capturing the noise of other conversations occurring near the caller of interest, which may be converted and transmitted to the receiver of the call. When the audio is converted and delivered to the receiver, the listener may find it difficult to understand the speaker with the interfering noise also delivered. Generally certain algorithms such as noise and echo cancellation are applied at the point of capture (such as in the mobile phone), where the signal may be converted for transmission, however, the applied algorithms traditionally only mitigate some of the noise/interfering effects and the receiving party may still receive interfering environmental noises which may impede the perceptibility of the sender.

The methods for source signal separation described herein may be introduced into any telephony application for the purposes of, but not limited to, amplifying targeted sounds and/or focusing on the cell phone or telephone user or the person of interest speaking on a conference call while minimizing or eliminating background or other ambient noises that a receiving party would prefer not to hear and/or have transmitted, as such unwanted transmissions would interfere with the user's comprehension of the calling party, speaker of interest and/or conversation.

These SS methods may be introduced and applied during any point of the source signal capture, conversion, transmission and/or delivery/output to the receiver in a telephony application. The SS methods may be integrated to be always applied during a call, or may be introduced with a control mechanism that may enable the sender or receiver to request the introduction of the SS methods to provide mitigation of interferers during a call. SS systems and methods may be incorporated as firmware, embedded software, a stand-alone software application or platform, or an additional software function or feature, which may be implemented from the point of collection, transmission or delivery (such as a cell phone or network) to be used alone or in conjunction with other algorithms for noise reduction, call clarity and/or other performance benefits.

In some embodiments, the SS applications may be used in car voice control systems that may face challenges in processing elements of a targeted audio command mixed with any of the following or similar interfering sound sources: road noise, external environmental noise, radio noise, HVAC noise, unintended cabin noise and accompanying passenger noises. The SS methods described herein may be used in conjunction with in-car voice response systems to extract and amplify targeted commands from unwanted or interfering background noise for accurate voice response system processing, automotive controls and vehicle security. The SS methods described herein may interact with a voice command system through the use of speech or extracted speech features that may be processed by the voice response system. The processing system may be contained on-board in a car-based-PC or transmitted to a central processing server outside of the vehicle. An exemplary embodiment of the voice response commands controlled by such a system may include but are not limited to in-car navigation, auto system controls such as HVAC, windows, radio, seat function, wipers, automatic door locks and controls, sunroof controls and third party integrated device controls such as cell phone integration and iPod, tablet, mp3, audio and entertainment device controls. The SS system may also be linked to cellphones; Bluetooth and other headset systems to process such as both send and receive signals that may be passing through the vehicles central audio processing system. An additional deployment of the SS methods may be onboard voice biometrics for vehicle controls and security. Speech features captured by the SS systems and methods described herein may enable the extraction of precise speech features unique to each individual user. Representative deployments of this control feature may include but are not limited to driver/user assigned vehicle locks and alarm controls, driver engine start and turn-off controls (initiated onboard or through an external control device such as a cell phone), driver and/or specific user controls of navigation systems and non-essential vehicle control systems.

The SS systems described herein may be enabled by a single microphone (stereo or mono, directional or omnidirectional) or an array of microphones built into the cabin or through linkage to an external systems such as a Bluetooth headset or other hands free cellphone control device. The system may be deployed and programmed by the user such that the voice control system may only accept prompts for the driver's seat, both the driver and passenger seats, or an individual with a designated biometric signature. Separate controls may also be added such that individuals in the rear seats may control rear HVAC systems or rear entertainment systems. In some embodiments, drive or additional party voice biometric controls may be programmed through use of the system or through a download user voice biometric profile from another device using the SS methods described herein.

In some embodiments, the SS methods described herein may be deployed in a series of medical imaging applications that make use of static imaging or time-series imaging signal analysis including but not limited to the following: Ultrasound, MRI, CT Scans, PET Scans, X-Rays, SPECT, Gamma Camera Imaging, Nuclear Imaging, Photoacoustic Imaging, Breast Thermography, and Optical Coherence Tomography. The application of the SS methods described herein may enable improved resolution of targeted images and the reduction of noise generated by the imaging equipment in the above mentioned and other medical imaging systems. An exemplary embodiment of the SS methods and systems described herein may include applications in medical ultrasound systems to enhanced resolution and reduce the noise generated by overlapping elements in the ultrasound probe. SS algorithms may be incorporated into freestanding ultrasound systems, pc-based systems, tablet systems, smart phone apps, PDAs, and handheld systems. The SS algorithms may be incorporated as firmware that may run off the devices internal CPUs, software, or apps loaded on to the devices, or as DSPs or other chips incorporated into the control box or onto the ultrasound probe itself. The SS methods and systems for improved ultrasound may be incorporated pre- or post-summation of the data collected by the individual elements in the probe. The SS methods and systems described herein may be used pre and/ or post beam formation so as to be compatible with adjustments in beam angles and signal intensity to compensate for differences in targeted anatomy.

In some embodiments, the SS methods and systems described herein may be used with any form of ultrasound (such as sonography or echosonography) imaging software or add-on imaging analysis programs including but not limited to 2D ultrasound, 3D ultrasound, 4D ultrasound, tissue doppler, flow doppler tissue strain analysis, elasticity analysis and other applications. The SS software may be applied across all clinical practices including both diagnostic and surgical applications. Embodiments of SS enhanced ultrasound image may include ultrasound assisted biopsies, ultrasound assisted catheter placement, echo cardiology, cardiology and cardiac surgery applications, orthopedic and orthopedic surgical applications, sonography and other obstetrics and gynecology applications, including both imaging and surgical, urological applications, gastrointestinal applications, soft tissue applications, head, neck and cranial applications. The core ultrasound applications described herein may also be used with both ultrasound hardware and imaging software programs for veterinary and industrial applications including but not limited to ultrasonic analysis of composite materials, structures, and geological surveys.

In some embodiments, the SS techniques may be used for applications related to Sound Navigation And Ranging (Sonar), as well as for hydro acoustics applications. Sonar uses sound propagation to navigate, communicate with and/or detect objects on or under the surface of the water. There may be two types of sonar based applications that may include, applications based on a passive sonar technology that may "listen" for sounds generated by target objects; and applications based on an active sonar technology that may emit pulses of sounds and listen for echoes. Sonar may be used as a means of acoustic location and of measurement of the echo characteristics of "targets" in the water, and may be used in applications including, but not limited to, submarine navigation, guidance for torpedoes and mines, underwater survey and mapping, echo sounding, pipeline inspection, wave measurement, and determining the course, range, trajectory and speed of a target of interest (such as using the Target Motion Analysis).

In some embodiments, the SS methods and systems described herein may be used to enhance the signal quality with any form of active sonar which may use a sound transmitter and a receiver, which may be operated in monostatic, bistatic or multistatic configurations and the acoustic frequencies may vary from very low (infrasonic) to extremely high (ultrasonic). The sonar may utilize a pulse of sound generally created electronically using a signal generator, power amplifier and electro-acoustic transducer/array at constant frequency or a "chirp" of changing frequency (enabling pulse compression upon reception). The SS may also be incorporated in conjunction with a beam former that may be used to concentrate the acoustic power into a beam, which may be swept to cover the required search angles. Occasionally, the acoustic pulse may be created by other means, such as by chemically using explosives, or by using air guns or by using plasma sound sources.

In some embodiments, the SS methods and systems described herein may be used to enhance the signal quality with any form of passive sonar, which may typically "listen" without transmitting any pulses and has a wide variety of techniques for identifying the source of a detected sound, generally by comparing the detected sound against large sonic databases. Through use of passive sonar, if the target radiated noise level is high enough it allows the target to be identified. However, in some examples, operation may be affected by variations in sound speed determined by the water's bulk modulus, mass density, temperature, dissolved impurities (usually salinity), and even water pressure.

In one or more embodiments described herein, the SS methods described herein may be applied to all forms of active and passive sonar systems to address sound variations as well as mitigate noise, interference, and/or scatter at any point within the process of analysis once sound or echo has been received, and thereby enhancing the quality of the final data delivered to the end use application. It may be introduced in the software or hardware components of the receiving, transmission or display systems independent of any other correction algorithms and systems or in conjunction with one or more of such systems, such as beam forming and narrow beam transmissions. In some examples, sources of noise that interfere with the desired target echo or signature may range from waves and shipping to turbulence and marine life. Additionally, the motion of the receiver through the water may also cause speed-dependent low frequency noise. When active sonar is used, scattering may occur from small objects in the sea as well as from the bottom and surface. In addition to active and passive sonar, the SS technology may be applied to deliver benefit to other sonar-based systems including, but not limited to, synthetic aperture sonar and parametric and non-linear sonar. The SS methods and systems described herein may also be introduced to hydro acoustic systems, including underwater acoustic communication that may be used to send and receive messages below water. There may be several ways of employing such communication but the most common may include using hydrophones. Underwater communication may be difficult due to numerous factors, which can be addressed by SS, including but not limited to: multi-path propagation; time variations of the channel; small available bandwidth; and strong signal attenuation.

In some embodiments, the SS systems and methods described herein may be used in microphone dependent systems. Much like cell phones and other telephony systems, headsets, speakerphones and general microphone based systems (used either alone or in conjunction with cellular or other telephony networks) may have the unintended effects of receiving, processing and transmitting the device user as well as unintended background noise and ambient noise present at the time of transmission/recording. Current systems may not be capable of isolating the targeted users from other ambient or interfering noises that may overpower the speaker and may make it difficult for the receiver/user to comprehend the intended transmission/recording. Representative examples of this problem may include: the transmission of airplane noise through flight control systems, the broadcast of PA announcements at the airport through a cell phone headset, room noise broadcast through a conference call speaker system, auto and outdoor noises broadcast through a "drive-thru" ordering system, or even crowd noise broadcast over a coach's headset.

The SS systems and methods described herein may be incorporated into such microphone dependent devices for the purpose of improving the quality/intelligibility of the user relative to unwanted/unintended ambient/background noises captured by the microphone in the transmitting/recording device. The SS methodology may be optimized for each device so that it may only transmit sound sources emanating from a specific speaker, or defined limited area/radius, such as the proximal device user and turning off far field noises. This may be achieved by using SS methods and systems to extract and selectively transmit/record sounds from the targeted speaker and not the unintended background noises.

An exemplary embodiment of such a system may include the addition of the SS systems and methods described herein to a Bluetooth headset. The SS technology may be added to the headset as a dedicated DSP or firmware added to an existing processor. It may be capable of processing the signals captured by the devices' microphone (directional or omni-directional), extracting the targeted sound source from the unintended noise, before the resulting signal may be transmitted or recorded. This may assure that the recording device or transmitting systems may only record the extracted sound source, hence increasing the quality and intelligibility of that sound source. This new step in the processing chain may be used as a stand-alone feature or may be used in combination with other audio processing and enhancement algorithms. Another exemplary embodiment of the SS systems and methods described herein may be used in microphone-based recordings. Targeted sound sources may be extracted and recorded on one channel, while background noises may be recorded on a separate channel. Each channel may then be remixed for optimal/desired sound effects and quality.

In accordance with exemplary and non-limiting embodiments, a system comprises a sound gathering device, such as a microphone, or a sound transmitting device for communication (e.g., using Bluetooth or another communications protocol), with a nearby processor for engaging in cooperative/distributed computing of source signal separation. In some embodiments, some processing may be distributed to remote server by the processor with results returned and transmitted through the communication system.

In another embodiment, ambient noise or background noise distinct from the targeted input signal may be removed from an input source signal to produce a deconstructed source signal which may then be re-combined with the ambient or background noise at a lower or reduced presentation level and outputting the combined signal. In some embodiments, the user may dynamically or statically alter the presentation level of the reintroduced ambient noise.

In some embodiments, the SS systems and methods described herein may be used in voice controlled television and other interactive device based applications. The growth of voice recognition and voice driven command systems for TV, video games, entertainment systems and other interactive devices has been limited by the challenges of interfering noises, unintended speakers interrupting commands, and background noise impacting command recognition and response. The SS methods described herein may be embedded in any such entertainment device for the purpose of assuring accurate voice recognition and response. Additionally, such devices may be linked or utilize a network-dependent solution for speech and voice recognition similar to those described {in the section detailed earlier} to which SS methods described herein may be applied. An exemplary embodiment of the SS systems and methods described herein may include be the use of SS in voice response/voice controls for television function. SS may enable the system to focus on a specific speaker (s) that may be preprogrammed in the system or an unknown speaker talking into a remote control or other similar device. The speakers' voice commands may be configured to control all device features and those of related devices including but not limited to cable TV boxes, DVR systems, satellite systems, DVD players, integrated sound systems, PCs, video game systems/consoles, internet connectivity, cloud connectivity, video conference systems, VOIP/internet phone systems, and other similar devices. In some examples, the TV voice response controls may be driven by any microphone or speaker/microphone combination systems including but not limited to television embedded microphone/speakers, dedicated remote control microphone/speakers, external microphone/speaker systems, cell phones, tablets, PCs, video game systems and headsets. In such examples, the control features may use directional/omni-directional microphones and or may make use of IR, bluetooth, wifi, RF or wired linkages to the system. Such a system may permit two-way interaction, both accepting and responding to voice driven queries, and it may also serve as the interface for video conferencing, web conferencing, VOIP, and web based conference calls. The SS methods and systems for Voice Controlled TV described herein may or may not re-synthesize the received speech. In noisy environments, received speech may be processed as speech features or speech vectors based on the SS mathematical models described herein for purposes of driving a speech recognition engine or voice response system. With re-synthesized speech, varying levels of background noise may be reincorporated. The system may be trained to respond to a targeted voice or voices. In some embodiments, speaker recognition training may be generated through device use or the citation of speech at the time of device initialization.

In some embodiments, the SS methods and systems described herein may be used in electrical power supply monitoring related applications. The electrical power supply emits a continuous low-level noise, which e.g., averages roughly 50 Hz in some applications. Fluctuations in power demand may cause slight variations in this noise level. For example, increased electrical demand may lower the noise level, while reduced demand level may have the opposite effect. Fluctuations in power demand may give the power grid the capability of providing a unique time/date signature that may be correlated with any recording. The SS systems and methods described herein may be used to monitor the electric grid to create a highly accurate time series signature of the system. This signature may be derived from any recording device (audio or video) or source signal type (analog or digital). The low level audio signal may be consistent across the system and the signal analysis may take place at generation station, specific machine or any other location. The SS systems and methods described herein may be configured to extract the signal impact of electrical supply from any live feed or recording to provide a highly accurate time series signature of the electrical grid. This signature may be monitored real-time, near real-time or subsequently analyzed. An exemplary embodiment of this system may use SS to predict impending brown-outs, power spikes, power failures or disruptions in power supply. This may occur at a grid-wide level, at an individual site, or on an individual device by analyzing changes in the low-level noise vs. historic standards/predictors. A recording device may record the ambient noise at any of the above locations, machines or devices and then SS methods would separate the targeted electrical noise from other noises. The SS methods and systems may be configured to generate a reading of the power noise and send a warning of an impending event if the noise level poses any concerns. The warning may appear on the device itself or be sent through a network, wireless or through the cloud to any monitoring device, PC, tablet, cell phone or any other device.

Another exemplary embodiment of this system may be related to forensic audio analysis. This embodiment may include identification and validation of the date and time during which a recording was created. The SS methods and systems described herein may be used to extract the electrical system noise from a recording and generate a highly accurate mathematical representation of that signal. That signal may be correlated to known recordings from the electrical grid to determine the exact time and date at which the recording was created. Such authentication and/or validation may be necessary for verifying recordings to be admitted into evidence and to assure that such recording have not been adulterated. The analysis may be conducted on any type of recording (such as audio or video, digital or analog), file format, or duration of recording.

Fit User Interface allows a user to view and interact with the tracking, grouping, and peak selection for resynthesis stages of processing. User interface may be used "offline" to view and modify stored data, or "online" to command the processing components and interact with the data in real time. It may be used to analyze data, and modify component parameters. It may detect optimal component parameters from user interaction. For example, given a user's selection of data for resynthesis, the Fit User Interface may calculate processing parameters for detecting similar data.

In accordance with an exemplary and non-limiting embodiment, a user interface is provided for viewing a signal as: tracks; a plurality of potentially coherent tracklets and/or coherent groups for editing the visual representation to at least one of add, remove or group signal data with the tracks, tracklets and/or coherent groups.

In another embodiment, the user interface may be utilized to view a signal as: tracks; a plurality of potentially coherent tracklets; and/or coherent groups wherein a user can click on a track, tracklet; and/or coherent group and to be presented the data associated with that track, tracklet and/or coherent group. In another embodiment, the user interface may be utilized for viewing a signal as a track; plurality of potentially coherent tracklets; and/or coherent groups wherein a user can search and find a track and/or tracklet within the interface based on input comprising characteristic data about that track, tracklet, and/or group. In another embodiment, a user may change the scoring function on the fly to modify what data is associated into tracks, groups, and/or tracklets.

Figure 16:
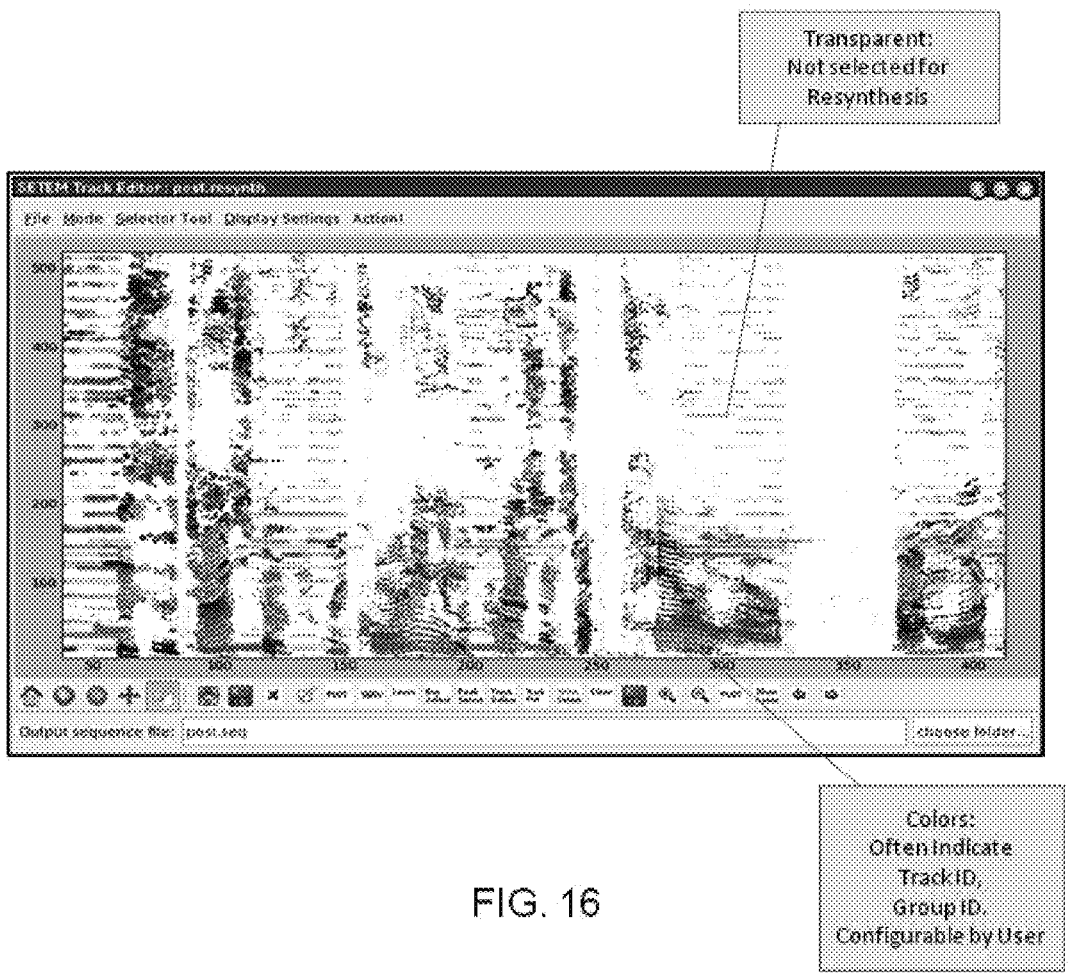
FIG. 16 is an illustration of a track editor according to an exemplary and non-limiting embodiment.

With reference to FIG. 16, there is illustrated an exemplary embodiment of a track editor as may be practiced in accordance with the embodiments and description above. As illustrated, the track editor displays a plurality of tracklets composed of oscillator peaks. In various exemplary and non-limiting embodiments, oscillator peaks may be colored according to track-id. In yet other embodiments, oscillator peaks may be colored according to coherent group-id. In other embodiments, oscillator peaks may be colored or set transparent according to whether or not they are selected for resynthesis. In other embodiments, oscillator peaks may be colored according to any other oscillator peak parameter. In other embodiments, oscillator peaks may be scaled according to amplitude, amplitude with respect to background power, or with equal size.

Figure 17:
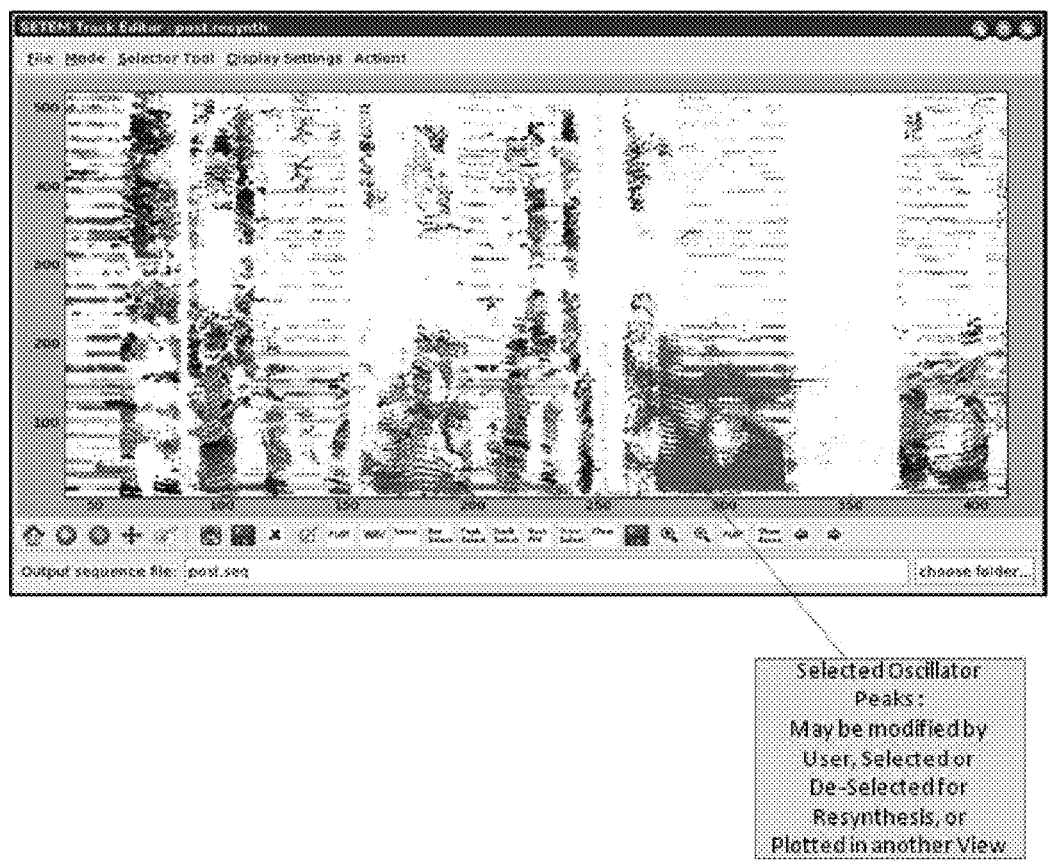
FIG. 17 is an illustration of a track editor sub-selection according to an exemplary and non-limiting embodiment.

With reference to FIG. 17, there is illustrated an exemplary and non-limiting embodiment of a track editor GUI. In accordance with exemplary and non-limiting embodiments, a user may select data displayed in the track editor GUI in order to perform an action on the selected data. In one embodiment, data may be selected by area such as via drawing with a box or a lasso. In other embodiments, a user may select data by tracklet such as by clicking on any peak in a tracklet. In other embodiments, a user may select data by coherent group such as by clicking on any peak in a coherent group. In yet another embodiment, a user may select data by oscillator peak such as by clicking on any peak.

Once selected, a user may select an action to be performed on the data. For example, a user may plot the data in another view wherein there is visually rendered oscillator peak statistics, direction of arrival, time-domain audio, spectrogram data and the like. In some embodiments, a user may Instruct the system whether or not to include select peaks for resynthesis such as via a "Turn on/Turn off" option.

Figure 18:
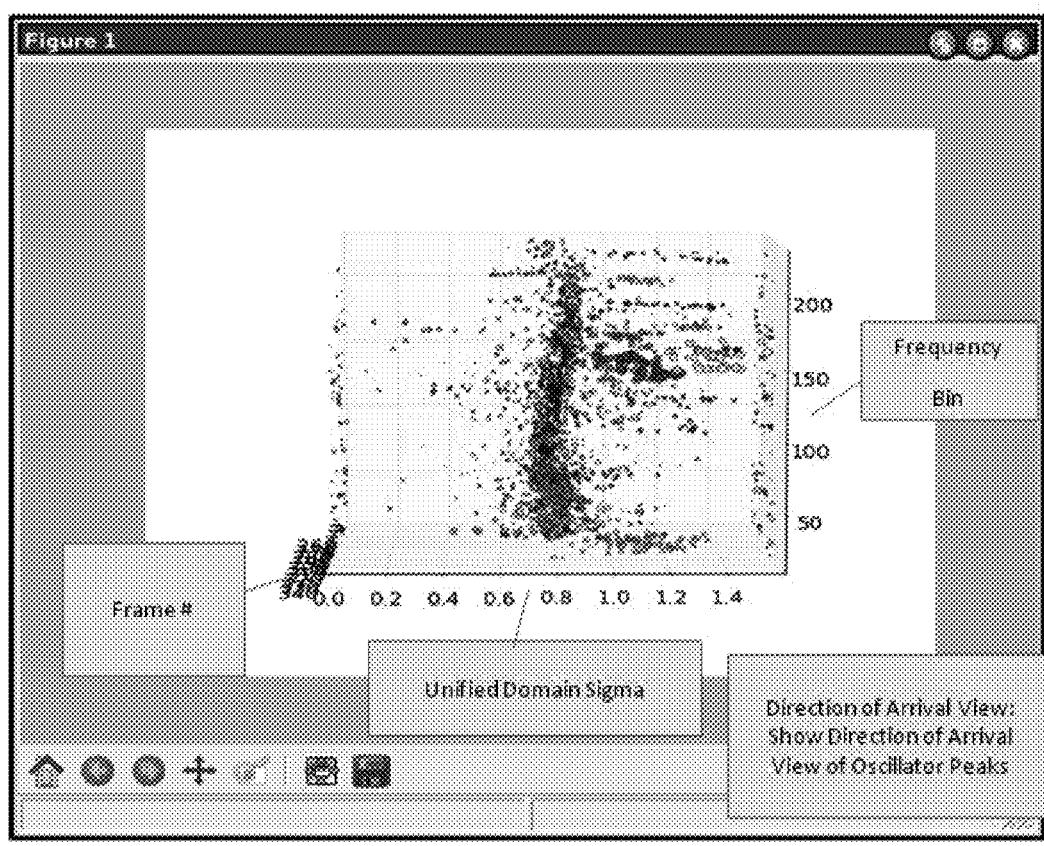
FIG. 18 is an illustration of track editor data visualizer according to an exemplary and non-limiting embodiment.

With reference to FIG. 18, there is illustrated an exemplary embodiment of a data visualizer for displaying user selected data as described above.

The SS methods and systems in accordance with various embodiments may be implemented in software, hardware, firmware, or any combination thereof. The processes may preferably be implemented in one or more computer programs executing on a variety of computer-equipped devices (such as personal computers, mobile phones, imaging devices, hearing aids, interactive voice response systems, conference call systems, audio recording devices, in-vehicle voice activation systems, dictation systems, and communications systems). Such devices may include, among other things, a computer processor (such as general and special purpose microprocessors), and a storage medium readable by the processor and input and output devices. Each computer program may be a set of instructions (program code) in a code module resident in the random access memory of the device. Until required by the computer processor, the set of instructions may in some cases be stored in another computer memory (such as in semiconductor memory devices, hard disk drives, or removable memory devices such as optical disks, external hard drives, memory cards, or flash drives) or stored on another computing device and downloaded via the Internet or other network.

Having thus described several illustrative embodiments, it may be appreciated that various alterations, modifications, and improvements will readily occur to those skilled in the art. Such alterations, modifications, and improvements may be intended to form a part of this disclosure, and may be intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions.

While only a few embodiments have been shown and described, it will be obvious to those skilled in the art that many changes and modifications may be made thereunto without departing from the spirit and scope as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. Various embodiments described herein may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of the program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SAAS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference.

We claim:

1. A method of processing a signal, comprising:
   taking a signal formed from a plurality of source signal emitters and expressed in an original domain;
   decomposing the signal into a mathematical representation of a plurality of constituent elements in an alternate domain;
   analyzing the plurality of constituent elements to associate at least a subset of the constituent elements with at least one of the plurality of source signal emitters;
   separating at least a subset of the constituent elements based on the association; and
   reconstituting at least a subset of constituent elements to produce an output signal in at least one of the original domain, the alternate domain and another domain.

2. The method of claim 1 wherein analyzing further comprises using direction-of-arrival estimates within a unified domain representation.

3. The method of claim 1 wherein the analyzing the plurality of the constituent elements further comprises using complex spectral phase evolution of at least a subset of the constituent elements.

4. The method of claim 1 wherein separating the constituent elements further comprises associating at least a subset of constituent elements with a tracklet.

5. The method of claim 4 wherein separating the constituent elements further comprises grouping tracklets that emanate from a single source.

6. A method of processing a time domain signal, comprising:
   receiving an input signal comprising a time domain signal stream and creating a first windowed data set and a second windowed data set from the signal stream, wherein an initiation of the second windowed data set time lags an initiation of the first windowed data set;
   converting the first windowed data set and the second windowed data set to a frequency domain and storing the resulting data as frequency domain data having a fundamental transform resolution;
   performing complex spectral phase evolution (CSPE) on the frequency domain data to estimate component frequencies of the first and second windowed data sets at a resolution greater than the fundamental transform resolution;
   using the component frequencies estimated in the CSPE, sampling a set of frequency-domain high resolution windows to select a frequency-domain high resolution window that fits at least one of the amplitude, phase, amplitude modulation and frequency modulation of a component of an underlying signal wherein the component comprises at least one oscillator peak;
   using a tracking algorithm to identify at least one tracklet comprised of one or more oscillator peaks that emanate from a single oscillator source within the underlying signal;
   grouping tracklets that emanate from single sources; and
   providing an output signal.

7. The method of claim 6 wherein the input signal comprises an analog voice signal.

8. The method of claim 6 wherein the signal is reconstructed to reproduce a conversation of one or more selected speakers.

9. The method of claim 6 wherein the input signal is received at a hearing aid and the output is delivered ultimately to an ear.

10. The method of claim 6 wherein the set of frequency-domain high resolution windows is pre-computed and stored.

11. The method of claim 6 wherein the set of frequency-domain high resolution windows is computed in one of near real time and real time.

12. The method of claim 11 wherein the set of frequency-domain high resolution windows is calculated from a functional representation.

13. The method of claim 6 further comprising providing a unified domain representation of the data from the CSPE to enable use of direction-of-arrival estimates in the unified domain to assist in fitting to a constituent component of the signal.

14. The method of claim 6, further comprising adding at least a portion of constituent elements not associated with a desired signal source to provide a modified level of background noise along with a preserved portion of the original input signal, including when the preserved portion is enhanced or increased in amplitude.

15. The method of claim 14 wherein the preserved portion is increased in amplitude.

16. A method of processing a time domain signal, comprising:
   receiving a time domain signal stream and creating a first windowed data set and a second windowed data set from the signal stream, wherein an initiation of the second windowed data set time lags an initiation of the first windowed data set;
   converting the first windowed data set and the second windowed data set to a frequency domain and storing the resulting data as frequency domain data having a fundamental transform resolution;
   performing complex spectral phase evolution (CSPE) on the frequency domain data to estimate component frequencies of first and second window at a resolution greater than the fundamental transform resolution;
   using the component frequencies estimated in the CSPE, sampling a set of stored high resolution frequency-domain windows in a singlet transformation process to select a high resolution frequency-domain window that fits at least one of the amplitude, phase, amplitude modulation and frequency modulation of the underlying signal oscillator;
   storing the parameters required for at least one of FM creation and AM creation in the frequency domain, wherein the parameters for FM creation include amplitude, phase, reference frequency, and modulation rate and the parameters for AM creation include amplitude, phase, frequency, and amplitude envelope information; and recreating the frequency spectrum for at least one of an FM-modulating oscillator peak and an AM-modulating oscillator peak, such frequency spectrum including any transient effects where the oscillator may turn on or off at some point within the data sample window.

17. The method of claim 16 further comprising combining a recreated frequency spectrum for at least one of an FM-modulating oscillator peak and an AM-modulating oscillator peak with a frequency spectrum for another oscillator peak.

18. The method of claim 16 further comprising, including in the frequency spectrum representation of an oscillator peak signal spreading information to represent the signal element to a desired degree of accuracy.

19. The method of claim 16 further comprising, selecting analysis windows for the frequency spectrum representation appropriate to account for smearing through at least one of the zero frequency bin and the highest frequency bin.

20. The method of claim 16 further comprising including in the frequency spectrum of an oscillator peak signal spreading information to account for at least one of a continuous wrapping effect and a plurality of wrapping effects.

\* \* \* \* \*